United States Patent
Simard

(10) Patent No.: US 10,166,244 B2
(45) Date of Patent: *Jan. 1, 2019

(54) TARGETING NC$_{CA-ATP}$ CHANNEL FOR ORGAN PROTECTION FOLLOWING ISCHEMIC EPISODE

(71) Applicants: University of Maryland, Baltimore, Baltimore, MD (US); The United States of America as Represented by the Department of Veterans Affairs, Washington, DC (US)

(72) Inventor: J. Marc Simard, Baltimore, MD (US)

(73) Assignees: University of Maryland, Baltimore, Baltimore, MD (US); The United States of America as Represented by the Department of Veteran Affairs, Washington, DC (US)

( * ) Notice: Subject to any disclaimer, the term of this patent is extended or adjusted under 35 U.S.C. 154(b) by 43 days.

This patent is subject to a terminal disclaimer.

(21) Appl. No.: 15/369,056

(22) Filed: Dec. 5, 2016

(65) Prior Publication Data

US 2017/0296555 A1 Oct. 19, 2017

Related U.S. Application Data

(63) Continuation of application No. 12/522,444, filed as application No. PCT/US2008/050922 on Jan. 11, 2008, now Pat. No. 9,511,075.

(60) Provisional application No. 61/012,613, filed on Dec. 10, 2007, provisional application No. 60/952,396, filed on Jul. 27, 2007, provisional application No. 60/923,378, filed on Apr. 13, 2007, provisional application No. 60/880,119, filed on Jan. 12, 2007.

(51) Int. Cl.
| | |
|---|---|
| A61K 31/57 | (2006.01) |
| G01N 33/68 | (2006.01) |
| A61K 31/427 | (2006.01) |
| A61K 31/565 | (2006.01) |
| A61K 38/00 | (2006.01) |

(52) U.S. Cl.
CPC ......... *A61K 31/57* (2013.01); *G01N 33/6872* (2013.01); *A61K 31/427* (2013.01); *A61K 31/565* (2013.01); *A61K 38/00* (2013.01)

(58) Field of Classification Search
None
See application file for complete search history.

(56) References Cited

U.S. PATENT DOCUMENTS

| | | |
|---|---|---|
| 5,047,429 A | 9/1991 | Nye |
| 5,166,162 A | 11/1992 | Masereel et al. |
| 5,215,985 A | 6/1993 | Murphy et al. |
| 5,236,932 A | 8/1993 | Greenfield et al. |
| 5,281,599 A | 1/1994 | Murphy et al. |
| 5,451,580 A | 9/1995 | Murphy et al. |
| 5,545,656 A | 8/1996 | Loose et al. |
| 5,677,344 A | 10/1997 | Greenfield et al. |
| 5,811,393 A | 9/1998 | Klagsbrun et al. |
| 5,849,796 A | 12/1998 | Gericke et al. |
| 5,916,871 A | 6/1999 | Johnson |
| 5,929,082 A | 7/1999 | Chambers et al. |
| 5,962,645 A | 10/1999 | Keay et al. |
| 6,043,224 A | 3/2000 | Lee et al. |
| 6,056,977 A | 5/2000 | Bhagwat et al. |
| 6,100,047 A | 8/2000 | Wilkison et al. |
| 6,156,522 A | 12/2000 | Keay et al. |
| 6,180,671 B1 | 1/2001 | Freedman et al. |
| 6,184,248 B1 | 2/2001 | Lee et al. |
| 6,187,756 B1 | 2/2001 | Lee et al. |
| 6,232,289 B1 | 5/2001 | Keay et al. |
| 6,242,200 B1 | 6/2001 | Wilkison et al. |
| 6,365,577 B1 | 4/2002 | Iversen |
| 6,372,743 B1 | 4/2002 | Darrow et al. |
| 6,376,197 B1 | 4/2002 | Keay et al. |
| 6,469,055 B2 | 10/2002 | Lee et al. |
| 6,492,130 B1 | 12/2002 | Wilkison et al. |
| 6,492,339 B1 | 12/2002 | Sleevi et al. |
| 6,511,989 B2 | 1/2003 | Heitsch et al. |
| 6,569,633 B1 | 5/2003 | Wilkison et al. |
| 6,569,845 B1 | 5/2003 | Futamura et al. |
| 6,596,751 B2 | 7/2003 | Fujita et al. |
| 6,610,746 B2 | 8/2003 | Fryburg et al. |
| 6,613,785 B2 | 9/2003 | Bril et al. |
| 6,679,859 B1 | 1/2004 | Keipert et al. |
| 7,285,574 B2 | 10/2007 | Simard et al. |
| 7,877,048 B2 | 1/2011 | Kitagawa |
| 8,318,810 B2 | 11/2012 | Simard et al. |
| 9,511,075 B2 * | 12/2016 | Simard .................. A61K 31/57 |

(Continued)

FOREIGN PATENT DOCUMENTS

| | | |
|---|---|---|
| AU | 2003222020 A1 | 10/2003 |
| EP | 0338415 A3 | 3/1991 |

(Continued)

OTHER PUBLICATIONS

Nieuwenhuijs et al., "Hepatic ischemia-reperfusion injury: roles of Ca2+ and other intracellular mediators of impaired bile flow and hepatocyte damage"; Digestive Diseases and Sciences, Jun. 2006, vol. 51(6); 1087-102.

(Continued)

*Primary Examiner* — Joanne Hama
*Assistant Examiner* — Fozia Hamud
(74) *Attorney, Agent, or Firm* — Norton Rose Fulbright US LLP

(57) ABSTRACT

The present invention concerns protection of an organ or tissue outside of the central nervous system following an ischemic episode. In particular aspects, the invention concerns organ preservation for transplantation, angina pectoris, kidney reperfusion injury, and so forth. In specific embodiments, the organ is subjected to an inhibitor of an NC$_{Ca-ATP}$ channel that is regulated by SUR1. Exemplary inhibitors include sulfonylurea compounds, such as glibenclamide, for example.

19 Claims, 17 Drawing Sheets

Specification includes a Sequence Listing.

(56) References Cited

U.S. PATENT DOCUMENTS

| | | | |
|---|---|---|---|
| 2001/0003751 | A1 | 6/2001 | Terashita et al. |
| 2001/0016586 | A1 | 8/2001 | Guitard et al. |
| 2002/0013268 | A1 | 1/2002 | Fryburg et al. |
| 2002/0016443 | A1 | 2/2002 | Keay et al. |
| 2002/0016643 | A1 | 2/2002 | Sakata |
| 2002/0037928 | A1 | 3/2002 | Jaen et al. |
| 2002/0065315 | A1 | 5/2002 | Jensen et al. |
| 2002/0081306 | A1 | 6/2002 | Elliott et al. |
| 2002/0094977 | A1 | 7/2002 | Robl et al. |
| 2002/0166443 | A1 | 11/2002 | Haerr et al. |
| 2003/0215889 | A1 | 11/2003 | Simard et al. |
| 2003/0216294 | A1 | 11/2003 | Fryburg et al. |
| 2005/0009733 | A1 | 1/2005 | Stephenson et al. |
| 2005/0054659 | A1 | 3/2005 | Ellsworth et al. |
| 2006/0100183 | A1 | 5/2006 | Simard |
| 2006/0276411 | A1 | 12/2006 | Simard et al. |
| 2007/0203239 | A1 | 8/2007 | Gehenne et al. |
| 2009/0130083 | A1 | 5/2009 | Simard et al. |
| 2010/0092469 | A1 | 4/2010 | Simard et al. |
| 2010/0311639 | A1 | 12/2010 | Simard |
| 2011/0263478 | A1 | 10/2011 | Simard |
| 2012/0237449 | A1 | 9/2012 | Simard et al. |

FOREIGN PATENT DOCUMENTS

| | | |
|---|---|---|
| EP | 0467709 A3 | 7/1992 |
| EP | 1782815 A1 | 5/2007 |
| ES | P200401628 | 6/2004 |
| JP | H09208562 A | 8/1997 |
| JP | 2004-516236 A | 6/2004 |
| JP | 2009/208562 A | 9/2009 |
| WO | 1997/41857 A1 | 11/1997 |
| WO | 2001/010430 A2 | 2/2001 |
| WO | 2001/54771 | 8/2001 |
| WO | 2002/070499 A2 | 9/2002 |
| WO | 03057843 A2 | 7/2003 |
| WO | 03075933 | 9/2003 |
| WO | 2003/079987 A2 | 10/2003 |
| WO | 03079987 | 10/2003 |
| WO | 2004038655 A2 | 5/2004 |
| WO | 2005/041877 A2 | 5/2005 |
| WO | 2006/000608 A1 | 1/2006 |
| WO | 2006/034048 A2 | 3/2006 |
| WO | 2006/036278 A2 | 4/2006 |
| WO | 2007/011595 A2 | 1/2007 |
| WO | 2007011926 A2 | 1/2007 |
| WO | 2006/036278 A8 | 5/2007 |
| WO | 2007058902 | 5/2007 |
| WO | 2008/098160 A1 | 8/2008 |
| WO | 2009/002832 A2 | 12/2008 |
| WO | 2008/089103 A8 | 10/2009 |

OTHER PUBLICATIONS

Pompermayer et al.; "The ATP-sensitive potassium channel blocker glibenclamide prevents renal ischemia/reperfusion injury in rats"; Kidney International, May 2005, vol. 67(5); 1785-96.
Simard et al., "Newly expressed SUR1-regulated NCCa-ATP channel mediates cerebral edema after ischemic stroke"; Nature Medicine, Apr. 2006, vol. 12(4), 433-440.
International Search Report dated Sep. 10, 2008 (published Nov. 11, 2008) during the prosecution of International Application No. PCT/US2008/50922.
Written Opinion dated Sep. 10, 2008 during the prosecution of International Application No. PCT/US2008/50922.
International Preliminary Report on Patentability, dated Jul. 14, 2009 re International Application No. PCT/US2008/50922.
Kim, H.J., et al.; "Anthocyanins from soybean seed coat inhibit the expression of TNF-alpha-induced genes associated with ischemia/reperfusion in endothelial cell by NF-kappaB-dependent pathway and reduce rat myocardial damages incurred by ischemia and reperfusion in vivo"; FEBS Letters 580, Jan. 20, 2006; pp. 1391-1397.

European Search Report, dated Feb. 19, 2010 (published Feb. 19, 2010) during the prosecution of International Application No. PCT/US2008/050922.
Khan Hussein Hamed, et al.; "Comparison of Therapeutic Effects by K+ Channel Opener Minoxidil and Blocker Glyburide on Cerebral Ischemia Produced by MCAO and Levo-thyroxine in Rats"; Journal of China Pharmaceutical University; Jan. 2000; vol. 31(4); pp. 289-293.
Ahmad et al., "Mouse cortical collecting duct cells show nonselective cation channel activity and express a gene related to the cGMP-gated rod photoreceptor channel," Proc. Natl. Acad. Sci. USA, 89: 10262-10266, 1992.
Angel et al., "The binding site for [3H]glibenclamide in the rat cerebral cortex does not recognize K-channel agonists or antagonists other than sulphonylureas," Fundam. Clin. Pharmacol, 5(2): 107-15, 1991 (abstract only).
Armijo, "Advances in the physiopathology of epilegtogenesis: molecular aspects," Rev. Neurol., 34(5): 409-29, 2002 (abstract only).
Ballerini, "Glial cells express multiple ATP binding cassette proteins which are involved in ATP release," Neuroreport, 13(14): 1789-92, 2002 (abstract only).
Baudelet et al., "Evidence for a Neuroprotective Effect of Pyrid-3-yl-sulphonyl-urea in Photochemically Induced Focal Ischaemia in Rats: Magnetic Resonance Imaging Evaluation," J. Pharm. Pharmacol., 51: 967-970, 1999.
Bevan et al, "Voltage Gasted Ionic Channels in Rat Cultured Astrocytes, Reactive Astrocytes and an Astrocyte-oligodendrocyte Progenitor Cell, " J. Physiol vol. 82, 1987, pp. 327-335.
Champigny et al., "A voltage, calcium, and ATP sensitive non selective cation channel in human colonic tumor cells," Biochem. Biophys. Res. Commun., 176: 1196-1203, 1991.
Chen et al., "Cell Swelling and a Nonselective Cation Channel Regulated by Internal Ca2+ and ATP in Native Reactive Astrocytes from Adult Rat Brain," J. Neurosci, 21(17): 6512-6521, 2001.
Davies, "Insulin secretagogues," Curr. Med. Res. Opin. 18 Suppl., 1: ss22-30, 2002 (abstract only).
Gopalakrishnan et al., "Pharmacological characterization of a 1,4-dihydropyridine analogue, 9-(3,4-dichlorophenyl)-3,3,6,6-tetramethyl-3,4,6,7,9,10-hexahydro-1,8(2H,5H)-acridinedione (A-184209) as a novelK(ATP) channel inhibitor," Br. J. Pharmacol., 138(2): 393-99, 2003 (abstract only).
Gray et al., "Non-selective cation channel on pancreatic duct cells," Biochem. Biophys. Acta, 1029:33-42, 1990.
Gribble et al., "Differential selectivity of insulin secretagogues. Mechanisms, clinical implications, and drug Interactions," J. Diabetes Complications, 17(2 Suppl): 11-5, 2003 (abstract only).
Gribble et al., "Tissue Specificity of Sulfonylureas: Studies on Cloned Cardiac and B-Cells K-ATP Channels," Diabetes, 47: 1412-1418, 1998.
Hambrock et al., "Four novel splice variants of sulfonylurea receptor 1," Am. J. Physiol. Cell Physiol., 283: C587-C598, 2002.
Hernandez-Sanchez et al., "Mice transgenically overexpressing sulfonylurea receptor 1 in forebrain resist seizure Induction and excitotoxic neuron death," PNAS, 98(6): 3549-3554, 2001.
Jarvis et al., "Purinergic Mechanisms in the Nervous System Function and Disease States," Psychopharmacology: The Fourth Generation of Progress, (Kupfer, David J. et al., Lippincott 2000), found at www.acnp.org/g4/GN401000063/CH.html.
Kimelberg et al., "Astrocytic swelling in traumatic-hypoxic brain injury. Beneficial effects of an inhibitor of anion exchange transport and glutamate uptake in glial cells," Mol. Chem. Neuropathol., 11(1): 1-31, 1989 (abstract only).
Koch et al., "Mechanism of shrinkage activation of nonselective cation channels in M-1 mouse cortical collecting duct cells," J. Membr. Biol., 177(3): 231-42, 2000 (abstract only).
Koch et al., "Osmotic shrinkage activates nonselective cation (NSC) channels in various cell types," J. Membr. Biol., 168(2): 131-39, 1999 (abstract only).
Lauritzen et al., "The potassium channel opener (-)-cromakalim prevents glutamate-induced cell death in hippocampal neurons," J. Neurochem., 69(4): 1570-79, 1997 (abstract only).

(56) References Cited

OTHER PUBLICATIONS

Lee et al., "Direct demonstration of sulphonylurea-sensitive KATP channels on nerve terminals of the rat motor cortex," Br. J. Pharmacol., 115(3): 385-87, 1995 (abstract only).
Lee et al., "The high-affinity sulphonylurea receptor regulates KATP channels in nerve terminals of the rat motor cortex," J. Neurochem., 66(6): 2562-71, 1996 (abstract only).
Lee et al, "Upregulation of Phospolipase D in Astrocytes in Response to Transient Forebrain Ischemia," GLIA vol. 30, 2000, pp. 311-317.
Liu et al., "Tenidap, a novel anti-inflammatory agent, is an opener of the inwardly rectifying K+ channel hKir2.3," Eur. J. Pharmacol., 435(2-3): 153-60, 2002 (abstract only).
Mest et al., "Glucose-induced insulin secretion is potentiated by a new imidazoline compound," Naunyn Schmledebergs Arch. Pharmacol., 364(1): 47-52, 2001.
Ono et al., "ATP and calcium modulation of nonselective cation channels in IMCD cells," Am. J. Physiol., 267: F558-F565, 1994.
Perillan et al., "Inward Rectifier K+ Channel Kir2.3 (IRK3) in Reactive Astrocytes from Adult Rat Brain," GLIA, 31: 181-192, 2000.
Perillan et al., "K+ Inward Rectifier Currents in Reactive Astrocytes from Adult Rat Brain," GLIA, 27: 213:225, 1999.
Perillan et al., "Transforming Growth Factor-B1 Regulates Kir2.3 Inward Rectifier K+ Channels via Phospholipase C and Protein Kinase C-d in Reactive Astrocytes from Adult Rat Brain," J. Biol. Chem., 277: 1974-1980, 2002.
Popp et al., "A Calcium and ATP Sensitive Nonselective Cation Channel in the Antiluminal Membrane of Rat Cerebral Capillary Endothelial Cells," Biochimica et Biophysica Acta vol. 1108, 1992, pp. 59-66.
Proks et al., "Sulfonylurea stimulation of insulin secretion," Diabetes, 51(Suppl. 3): S368-76, 2002.
Rae et al., "A non-selective Cation Channel in Rabbit Corneal Endothelium Activated by Internal Calcium and Inhibited by Internal ATP," Exp. Eye. Res., 50: 373-384, 1990.
Schroder et al., "AMPA receptor-mediated modulation of inward rectifier K+ channels in astrocytes of couse hippocampus," Mol. Cell Neurosci., 19(3): 447-8, 2002 (abstract only).
Schubert et al., "Cascading glia reactions: a common pathomechanism and its differentiated control by cyclic nucleotide signaling," Ann. N.Y. Acad. Sci., 903: 24-33, 2000 (abstract only).
Sturgess et al., "Calcium and ATP regulate the activity of a nonselective cation channel in a rat insulinoma cell line," Pflugers Arch., 409: 607-615, 1987.
Verkhratsky et al., "Ion channels in glial cells," Brain Res. Rev., 32: 380-412, 2000.
Auger, G. et al; Purification and Partial Characterization of a Hepatocyte Antiproliferative Glycopeptide, Journal of Cellular Biochemistry, (1989) vol. 40, pp. 439-451.
Keay, S., et al.; Bladder Epithelial Cells from Patients with Interstitial Cystitis Produce an Inhibitor of Heparin-Binding Epidermal Growth Factor-Like Growth Factor Production, The Journal of Urology (Dec. 2000) vol. 164, pp. 2112-2118.
Keay, S., et al.; Changes in human bladder epithelial cell gene expression asscoiated with interstitial cystitis or antiproliferative factor treatment, Physiol. Genomics (2003) vol. 14, pp. 107-115.
Keay, S., et al.; Current and future directions in diagnostic markers in interstitial cystitis, Intern'l J. of Urology (2003) vol. 10, pp. S27-230.
Keay, S., et al.; Decreased In Vitro Proliferation of Bladder Epithelial Cells from Patients with Interstitial Cystitis, The Journal of Urology (2003) vol. 61, pp. 1278-1284.
Elliott, Byron D., et al; "Comparative Placental Transport of Oral Hypoglycemic Agents in Humans: A Model of Human Placental Drug Transfer"; Am. J. Obstet. Gynecol., Sep. 1994, vol. 171, No. 3, pp. 653-660.
Elliott, Byron D., et al; "Insignificant Transfer of Glyburide Occurs Across the Human Placenta"; Oct. 1991; Am. J. Obstet. Gynecol., vol. 165, No. 4, Part 1, pp. 807-812.

Koren, Gideon; "Glyburide and Fetal Safety; Transplacental Pharmacokinetic Considerations"; Reproductive Toxicology, 2001, vol. 15, pp. 227-229.
Tosun, Cigdem, et al; "The Protective Effect of Glibenclamide in a Model of Hemorrhagic Encephalopathy of Prematurity"; Brain Sciences, 2013, vol. 3, pp. 215-238.
Mizognchi et al., "Inhibition of Carbonic Anydrases Enhanced the Recovery from Acute Experimental colitis by Controlling Epithelial Registration", Abstract In: Elsevier Health Journals, p. 821, 2003.
Kawaguchi et al., "A case of hemorrhagic colitis associated with flufenamic acid aluminium", Japanese Journal of National Medical Services, 47(12):999-1003, 1993.
Gunal et al., "Estradiol Treatment Ameliorates Acetic Acid-Induced Gastric and Colonic Injuries in Rats", Inflammation, 27(6):351-359, 2003.
Jin et al., "Altered gene expression and increased bursting activity of colonic smooth muscle ATP-sensitive K+ channels in experimental colitis", Am. J. Physiol. Gastrointest. Liver Physiol., 287:G274-G285, 2004.
Daneshmand et al., "Chronic lithium administration ameliorates 2,4,6-trinitrobenzene sulfonic acid-induced colitis in rats; potential role for adenosine triphosphate sensitive potassium channels", Gastroenterology and Hepatology, 26:1174-1181, 2011.
Fagan et al., "Targets for vascular protection after acute ischemic stroke"; Stroke. Sep. 2004;35(9):2220-5. Epub Jul. 29, 2004.
Gürsoy-Özdemir et al., "Role of Endothelial Nitric Oxide Generation and Peroxynitrite Formation in Reperfusion Injury After Focal Cerebral Ischemia"; Stroke. 2000;31:1974.
Manley et al., "Aquaporin-4 deletion in mice reduces brain edema after acute water intoxication and ischemic stroke"; Nature Medicine 6, 159-163 (2000).
Morris et al., "Extension of the Therapeutic Window for Recombinant Tissue Plasminogen Activator With Argatroban in a Rat Model of Embolic Stroke"; Stroke. 2001;32:2635-2640.
Nilius et al., "Transient Receptor Potential Cation Channels in Disease"; Physiol. Rev. 87: 165-217, 2007.
Pisano et al., "Undersulfated, low-molecular-weight glycol-split heparin as an antiangiogenic VEGF antagonist"; Glycobiology 2005 15(2):1C-6C.
Rosenberg et al., "TIMP-2 reduces proteolytic opening of blood-brain barrier by type IV collagenase" Brain Res—Apr. 3, 1992; 576(2): 203-7.
Ullrich et al., "Comparison of functional properties of the Ca2+-activated cation channels TRPM4 and TRPM5 from mice"; Cell Calcium. Mar. 2005; 37(3):267-78.
Grand, T., et al; "9-Phenanthrol Inhibits Human TRPM4 But Not TRPM5 Cationic Channels"; British Journal of Pharmacology; 2008, vol. 153, vol. 1697-1705.
Matsuo, Michinori, et al; "Different Binding Properties and Affinities for ATP and ADP Among Sulfonylurea Receptor Subtypes, SUR1, SUR2A, and SUR2B"; The Journal of Biological Chemistry; Sep. 15, 2000; vol. 275, No. 37, pp. 28757-28763.
Nilius, Bernd, et al; "Intracellular Nucleotides and Polyamines Inhibit the Ca2+-Activated Cation Channel TRPM4b"; Pfulgers Arch—Eur. J. Physiol., 2004, vol. 448; pp. 70-75.
Babenko; Audrey P., et al; "Pharmaco-topology of Sulfonylurea Receptors"; The Journal of Biological Chemistry (Accelerated Publication); vol. 275, No. 2, Jan. 14, 2000, pp. 717-720.
Earley, Scott, et al; "Protein Kinase C Regulates Vascular Myogenic Tone Through Activation of TRPM4"; American Physiological Society; Feb. 9, 2007; vol. 292; pp. H2613-H2622.
Woo, Seung Kyoon, et al; "The Sulfonylurea Receptor 1 (Sur1)-Transcient Receptor Potential Melastatin 4 (Trpm4) Channel"; The Journal of Biological Chemistry, Feb. 1, 2013, vol. 288, No. 5, pp. 3655-3667.
Pfeiffer et al., "Controlled extension of oral antidiabetic therapy on former insulin dependent diabetics by means of the combined i.v.. Glibenclamide-glucose-response test", Diabetologia, 8:41-47, 1972.
Wise, "New clinical guidelines for stroke published", BMJ, 320:823, 2000.
Bereczki et al., "Mannitol for acute stroke (Review)", Cochrane Database of Systematic Reviews, Issue 3, p. 1-20, 2009.

(56) References Cited

OTHER PUBLICATIONS

Chen et al., "Fenamates protect neurons against ischemic and exitotoxic injury in chick embryo retina", Neuroscience Letters, 242(3):163-166, 1998.
Riddle, "Editorial: sulfonylureas differ in effects on ischemic preconditioning—is it time to retire glyburide?", The Journal of Clincial Endocrinology & Metabolism, 2003, 88(2):528-530.
Gurke et al., "Mechanisms of ischemic preconditionin in skeletal muscle", Journal of Surgical Research, 2000, 94:18-27.
Greenwood et al., "Comparison of the effects of fenamates on Ca-activated chloride and potassium currents in rabbit portal vein smooth muscle cells" Biritish Journal of Pharmacology, 116:2939-2948, 1995.
Schmidt et al., "Endocrine and metabolic consequences of spinal injuries", Chapter 18, Sprinal Coard Medicine; Principles and Practices, pp. 221-235, 2002.
Launary et al., "TRPM4 Regulates Calcium Oscillations After T Cell Activation", Science, 306(5700):1374-1377, 2004.
Definition of "infusion" from www.merriam-webster.com, printed on Apr. 10, 2013, 1 pages as printed.
Heurteaux et al., "Alpha-Linolenic Acid and Riluzole Treatment Confer Cerebral Protection and Improce Survival After Focal Brain Ischemia", Neuroscience, 137:241-251, 2006.
Simard et al., "Comparative effects of glibenclamide and riluzole in a rat model of severe cervical spinal cord injury", Experimental Neurology, 233:566-574, 2012.
Demion et al., "TRPM4, a Ca2+-activated nonselective cation channel in mouse sino-atrial nod cells", Cardiovasuclar Research, 73:531-538, 2007.
Khansari, "An investigation of the neuroprotective properties of fenamate NSAIDs, against experimental models of schemic stroke", Dissertation Abstracts International, 68:11B, 197 pages, 2007.
Khansari and Halliwell, "Evidence for neuroprotection by the fenamate NSAID, mefenamic acid", Neurochemistry International, 55:683-688, 2009.
Klose et al., "Fenamates as TRP channel blockers: mefenamic acid selectively blocks TrPM3", British Journal of Pharmacology, 162:1757-1769, 2011.
Pirollo and Chang, "Targeted Delivery of Small Interfering RNA: Approaching Effetive Cancer Therapies", Cancer Res., 68(5):1247-1250, 2008.
Hausmann, "Post-traumatic inflammation following spinal cord injury", Spinal Cord, 41:369-378, 2003.
Woodcock, "The role of markers of inflammation in traumatic brain injury", Frontiers in Neurology, 4:1-18, 2013.
Hugelshofer, "Neuroinflammation after Subarachnoid Hemorrhage: The Role of Microglia", UniversitatsSpital Zurich Institut fur Neuropathologie & Klinik fur Neurochirurgie, p. 1-18, 2013.
Hallevi, "Inflammatory response to intraventricular hemorrage: Time course, magnitude and effect of t-PA," Journal of the Nurological Science, 315:93-95, 2012.
Kunte et al., "Sulfonylureas Improve Outcome in Patients With Type 2 Diabetes and Acute Ischemic Stroke", Stroke, 38(9):2526-2530, 2007.
Liang et al., Neurosurg Focus, 22(5):E2, pp. 1-16, 2007.
Gavin, "Management of Diabetes Mellitus During Surgery", West J M. 151:525-529, 1989.
Vestergaard et al., "Relative fracture risk in patients with diabetes melitus, and the impact of insulin and oral antidiabetic medication on relative fracture risk", Diabetologia, 48:1292-1299, 2005.
Inder and Volpe, "Mechanisms of Perinatal Brain Injury", 5 Semin, Neonatol. 3, 2000.
Wright et al., Evidence from Multicenter Networks on the Current Use and Effectiveness of Antenantal Corticosteroids in Low Birth Weight Infants, Am. J Obstet. Gynecol., 173:263, 1995.
Egarter et al., "Antibiotic Treatment in Preterm Premature Rupture of Membranes and Neonatal Morbidity: A Metaanalysis", Am. J. Obstet. Gynecol., 174:589, 1996.

Huss et al., "Differentiation of canine bone marrow cells with hemopoietic characteristics from an adherent stromal cell precursor", Proc natl. Acad. Sci USA, 92:748-752, 1995.
Lee et al., "In vitro antitumor activity of cromakalim in human brain tumor cells," Pharmacology, 49:69-74, 1994.
Salvail, Dany, et al., "Direct modulation of tracheal C1—channel activity by 5,6- and 11, 12-EET," Amer. Physio. Soc. (1998) pp. L432-L441.
Sharma, R.V., et al., "Isolation and characterization of plasma membranes from bovine carotid arteries." Amer. Physio. Soci. (1996) pp. C65-C75.
Eben-Brunnen, J., et al., "Lentil Lectin Enriched Microsomes from the Plasma Membrane of the Human B-Lymphocyte well Line H2LCL Carry a Heavy Load of Type-1 Porin", Biol. Chem., vol. 379, (1998) pp. 1419-1426.
Garcia, Ann Maria, et al., "Channel-mediated monovalent cation fluxes in isolated sarcoplasmic reticulum vesicles," J. Gen. Physiol., vol. 83, (Jun. 1984) pp. 819-839.
Nelson, N., et al., "Reconstitution of purified acetylcholine receptors with functional ion channels in planar lipid bilayers", Proc. Natl. Acad. Sci., Sci. USA, vol. 77, No. 5 (May 1990) pp. 3057-3061.
Suarez-Isla, B., et al, "Single calcium channels in native sarcoplasmic reticulum membranes from skeletal muscle." Proc. Nat'l. Acad. Sci., USA, vol. 83, (Oct. 1986) pp. 7741-7745.
Schindler, H. et al., "Functional acetylcholine receptor from Torpedo marmorata in planar membranes," Proc. Nat'l. Acad. Sci. USA, vol. 77, No. 5, (May 1980) pp. 3052-3056.
Garty, H. et al, "A simple and sensitive procedure for measuring isotope fluxes through ion-specific channels in heterogenous populations of membrane vesicles," The Jol. of Bio. Chem., vol. 256, No. 21 (1983) pp. 13094-13099.
Ren, et. al. "Altered mRNA Expression of ATP-Sensitive and Inward Rectifier Potassium Channel Subunits in Streptozotocin-Induced Diabetics Rat Herat and Aorta", J. Pharmacol Sci., 2003, vol. 93, pp. 478-483.
Proks ey al., "Inhibition of recombinant K(ATP) channels by the antidiabetic agents midaglizole, LY397364 and LY389382", Eur. J. Pharmacol.; 2002; 11-9, vol. 452(1).
Phillips, "The challenge of gene therapy and DNA delivery", Journal of Pharmacy and Pharmacology; 2001; 1169-1174; vol. 53(9).
Weith et al., "Stroke", 2001; 2029-3032; vol. 32.
Gribble et al., "The interaction of nucleotides with the tolbutamide block of cloned ATP-sensitive K+ channel currents expressed in Xenopus oocytes: a reinterpretation", J Physiol.; 1997; 35-45; vol. 504(Pt 1).
Plangger, "Effect of Torasemide on Intracranial Pressure, Mean Systemic Arterial Pressure, and Cerebral Perfusion Pressure in Experimental Brain Edema of the Rat", Acta Neurochir Suppl (Wien), 1994; 519-20; vol. 60.
Loffler-Walz et al., "Interaction of the diuretics torasemide and U-37883A with the K(ATP) channel in rat isolated aorta", Naunyn Schmiedebergs Arch Pharmacol.; 1998; 230-7; vol. 358(2).
Gribble, "Sulphonylurea action revisited: the post-cloning era", Diabetologia, 2003; 875-91. vol. 46(7).
Kempski, "Cerebral Edema", Semin Nephol; 2001; 303-307; vol. 21 (3); abstract only.
Unterberg, et al., "Edema and Brain Trauma", Neuroscience, 2004; 1021-1029; vol. 129.
Kaal, et al., "The Management of Brain Edema in Brain Tumors", Cuff. Opin. Oncol.; 2004; 593-600; vol. 16.
Eriksson, "Preparation of liver microsomes with high recovery of endoplasmic reticulum and a low grade of contamination", Biochim Biophys Acta; 1978; 155-64; vol. 508(1).
Mersel et al., "Plasma membrane isolated from astrocytes in primary cultures. Its acceptor oxidoreductase properties", Biochim Biophys Acta; 1984; 144-54; vol. 778(1).
Heinemann et al., "Frontiers in Bioscience 3, d483-493", May 1, 1998, printed out from the bioscience.org website as pp. 1-24.
Benos, "Methods to study CFTR protein in vitro", Journal of Cystic Fibrosis; 2004; 79-83; vol. 3.

(56) References Cited

OTHER PUBLICATIONS

Dubyak, "Ion homeostasis, channels, and transporters: an update on cellular mechanisms", Adv Physiol Educ; 2004; 143-154, vol. 28.
Hambrock et al., Mg2+ and ATP dependence of K(ATP) channel modulator binding to the recombinant sulphonylurea receptor, SUR2B, Br J Pharmacol. Oct. 1998;125(3):577-83.
Heinemann et al., Isolation and structural analysis of microsomal membrane proteins, Front Biosci. May 1, 1998;3: d483-93.
Simard, et al., "Brain Oedema in Focal Ischaemia: Molecular Pathophysiology and Theoretical Implications," Lancet Neurol. Mar. 2007;6(3):258-68.
Tank, D., et al., "Isolated-patch recording from liposomes containing functionally reconstituted chloride channels from Torpedo electroplax", Proc Natl Acad Sci U S A. Dec. 1982;79(24):7749-53.
Vidal, et al., "Making sense of antisense", Eur J Cancer. Dec. 2005;41(18):2812-8. Epub Nov. 9, 2005.
Haider et al., "Identification of the PIP2-binding site on Kir62 by molecular modelling and functional analysis," EMBO J. Aug. 22, 2007;26(16):3749-59. Epub Aug. 2, 2007.
Simard et al., "Endothelial sulfonylurea receptor 1-regulated NC Ca-ATP channels mediate progressive hemorrhagic necrosis following spinal cord injury," J Clin Invest. Aug. 2007;117(8):2105-13.
White, R. P., et al., "Cerebral Arterial Contractions Induced by Human and Bovine Thrombin", Stroke, vol. 11, No. 4, Jul. 1, 1980, pp. 363-368, XP55024008, ISSN: 0039-2499.
White, R. P., et al., "Comparison of Piroxicam, Meclofenamate, Ibuprofen, Aspirin, and Prostcyclin Efficacy in a Chronic Model of Cerebral Vasospasm", Neurosurgery, Williams & Wilkens, Baltimore, MD, vol. 12, No. 1, Jan. 1, 1983, pp. 40-46, XP000614038, ISSN 0148-396X.
Maeda, Yoshihisa, et al. "Endothelial Dysfunction and Altered Bradykinin Response Due to Oxidative Stress Induced by Serum Deprivation in the Bovine Cerebral Artery", European Journal of Pharmacology, Elsevier Science, NL, vol. 491, No. 1, Apr. 26, 2004, pp. 53-60, XP008150602, ISSN 0014-2999.
Yang, Shao-Hua, "17-beta Estradiol Can Reduce Secondary Ischemic Damage and Mortality of Subarachnoid Hemorrhage", Journal of Cerebral Blood FOLW and Metabolism, 2001, pp. 174-181, XP055024012.
Lin, et al., "17b-Estradiol Inhibits Endothelin-1 Production and Attenuates Cerebral Vasospasm After Expreimental Subarachnoid Hemorrhage", Experimental Biology and Medicine, Jun. 1, 2006, pp. 1054-1057, XP55024011, URL: http://ebm.rsmjoumals.com/content/231/6/1054.full.pdf#page=1&view=FitH [retrieved Apr. 5, 2012].
Kawanabe, Yoshifumi, et al., "Effects of the Ca++-permeable Nonselective Cation Channel Blocker LOE 908 on Subarachnoid Hemorrhage-induced Vasospasm in the Basilar Artery in Rabbits", Experimental Biology and Medicine, Mar. 2003, XP008150600.
Crépel, et al., "Glibenclamide depresses the slowly inactivating outward current (ID) in Hippocampal Neurons," Canadian Journal of Physiology and Pahrmacology, 70(2):306-307, 1992.
Gribble and Ashcroft, "Sulfonylurea Sensitivity of Adenosine Triposphate-sensitive Potassium Channels from b Cells and Extrapancreatic Tissues," Metabolism, 49(10Supp2):3-6, 2000.
Grijalva et al., "Efficacy and Safety of 4-aminopyridine in Patients with Long-term Spinal Cord Injury: A Randomized, Double-blind, Placebo-controlled trial," Pharmaccotherapy, 23(7):823-834, 2003.
Hozumi, et al., "Biochemical and Immunocytochemical Changes in Glial Fibrillary Acidic Protein After Stab Wounds," Brain Research, 524:64-71, 1990.
Liu, et al., "Suppression of Hippocampus Fos Expression and Activator Protein-1 (AP-1) Activity During Focal Cerebral Ischemia Using Antisense Strategy," Stroke, 26(1):182, 1995.
Wickelgren, "Animal Studies Raise Hopes for Spinal Cord Repair," Science, 297:178-181, 2002.
Yokoshiki, et al., "Antisense Oligodeoxynucleotides of Sulfonlurea Recepters Inhibit ATP-sensitive K+ Channels in Cultured Neonatal Rat Ventricular Cells," Pflugers Arcch—Eur J Physiol, 437:400-408, 1999.

Maybauer, D.M., et al, "The ATP-sensitive Potassium-channel Inhibitor Glibenclamide Improves Outcome in an Ovine Model of Hemorragic Shock," Shock, vol. 22(4), 2004, pp. 387-391.
Simard, J. M., et al.; "Glibenclamide Reduces Inflammation, Vasogenic Edema, and Caspase-3 Activation After Subarachnoid Hemorrhage"; Journal of Cerebral Blood Flow & Metabolism (2008), 29(2) pp. 317-330.
Simard, J. M., et al.; "Sulfonylurea Receptor 1 in the Germinal Matrix of Premature Infants"; Pediatr Res.; Dec. 2008; 34(6), pp. 648-652.
Wang, H., et al., "Targeting Ischemic Stroke with a Novel Opener of ATP-Sensitive Potassium Channels in the Brain", Molecular Pharmacology, vol. 66(5), 2004, pp. 1160-1168.
Koltz, Michael T., et al; "Tandem Insults of Prenatal Ischemia Plus Postnatal Raised Intrathoracic Pressure in a Novel Rat Model of Encephalopathy of Prematurity"; J. Neurosurg. Pediatrics, Dec. 2011, vol. 8, pp. 628-639.
Kraemer, Jennifer, et al; "Perfusion Studies of Glyburide Transfer Across the Human Placenta: Implications for Fetal Safety"; American Journal of Obstetrics and Gynecology, 2006, vol. 195, pp. 270-274.
Rashid, H., et al; Interstitial cystitis antiproliferative factor (APF) as a cell-cycle modulator, BMC Urology (2004) 4:3, pp. 1-5.
Zhang C. et al; Comparison of APF Activity and Epithelial Growth Factor Levels in Urine from Chinese, African-American, and White American Patients with Intestitial Cystitis, Urology (2003) vol. 61, pp. 897-901.
Parson, C.L., et al., "Role of Toxic Urine in Interstitial Cystitis", Journal of Urology (1990) vol. 143, p. 373A.
Beier-Holgersen, R., "The in vitro cytotoxicity of urine from patients with interstitial cystitis", Journal of Urology (Jan. 1994), vol. 151, pp. 206-207.
Nishimura, M., et al., "Cerebral ATM-Sensitive Potassium Channels During Acute Reduction of Carotid Blood Flow", American Heart Assoc., (1995), vol. 25, 1069-1074.
Simard, J., et. al., "Molecular pathophysiology of brains edema in focal ischemia—a focused review" (Apr. 8, 2006) pp. 1-483.
Hambrock, A., et al., "Mg2+ and ATP dependence of KATP Channel Modulator Binding to the Recombinant Sulphonylurea Receptor, SUR2B", British Journal of Pharm. 91998), vol. 125, pp. 577-583.
Torsemide Tablets Package Insert, pp. 1-2.
Torsemide advanced consumer drug information, pp. 1-10. http://www.drugs.com/MMX/Torsemide.html. (May 2006).
Zhu, Q. et al., "Modulation by Nucleotides of Binding Sites for [3H]Glibenclamide in Rat Aorta and Cardiac Ventricular Membranes", J. of Cardivascular Pharm., (2001), vol. 37, pp. 522-531.
Walaas et al., PCPP-260, A Purkinje Cell-Specific Cyclic AMP-Regulated Membrane Phosphoprotein of Mr 260,000, J Neurosci. Apr. 1986;6(4):954-61.
Favre, I., et al., "Reconstitution of Native and Cloned Channels into Planar Bilayers", Methods in Enzymology, (1999) vol. 294, pp. 287-304.
Simard, J. M., et al., "Newly Expressed SUR1-regulated NCca-ATP Channel Mediates Cerebral Edema after Ischemic Stroke", Nature Medicine (Apr. 2006) vol. 12, No. 4, pp. 433-440.
Jamme, I., et al., "Focal cerebral ischaemia induces a decrease in activity and a shift in ouabain affinity of Na +, K +—ATPase isoforms without modifications in mRNA and protein expression", Brain Research (1999) vol. 810, pp. 132-142.
Chen, M., et al., "Glial and Other Non-Neuronal Cell Specification and Differentiation IV", Society for Neuroscience, (2000) vol. 26, pp. 791.1.
Rosenberg, "Ischemic brain edema." Prog Cardiovasc Dis. Nov.-Dec. 1999; vol. 42(3):209-16.
Apo-Glibenclamide Data Sheet, Medsafe (New Zealand Medicines and Medical Devices Safety Authority), published Jun. 16, 1999, 6 pages; online http://www.medsafe.govt.nz/Profs/DataSheet/a/Apoglibenclamidetab.htm.
Slikker et al., "Session IV: Models of Neurotoxicity and Neuroprotection, Questions for Dr. Banik", Ann NY Acad Sci; 2003; 993; 159-160.

(56) References Cited

OTHER PUBLICATIONS

Sribnick et al., "Estrogen as a Neuroprotective Agent in the Treatment of Spinal Cord Injury", Ann. N.Y. Acad. Sci., vol. 993;. 2003;125-133.
Weih et al., "Sulfonylurea Drugs Do Not Influence Initial Stroke Severity and In-Hospital Outcome in Stroke Patients With Diabetes", Stroke. 2001; vol. 32(9):2029-2032.
Yong et al., "In vitro Antitumor Activity of Cromakalim in Human Brain Tumor Cells," Pharmacology 1994; vol. 49:69-74.
Yune et al., "Systemic Administration of 17?-Estradiol Reduces Apoptotic Cell Death and Improves Functional Recovery following Traumatic Spinal Cord Injury in Rats", Journal of Neurotrauma. Mar. 1, 2004, 21(3): 293-306.
Gagliardino, J.J. et al.; Inhibitory effect of sulfonylureas on protein phosphatase activity in rat pancreatic islets; Acta Diabetol (1997) 34:6-9; Springer-Verlang 1997.
Medline Plus® Merriam Webster Medical Dictionary, main entry: par.en.ter.al, online <http://www2.merriam-webster.com/cgi-bin/mwmednlm>; 2005; 1 page.
Rothstein et al, "Neuroprotective strategies in a model of chronic glutamate-mediated motor neuron toxicity," J Neurochem. Aug. 1995;65(2):643-51.
Sang et al., "ATP sensitive potassium channels are involved in the protective effect of ischemic preconditioning on spinal cord in rabbits"; Chinese Pharmacological Bulletin, 2003, Issue 12, 1362-1365.
Aguilar-Bryan et al., "Cloning of the beta cell high-affinity sulfonylurea receptor: a regulator of insulin secretion," Science, 268: 423-426, 1995.
Bareyre et al., "Inflammation, degeneration and regeneration in the injured spinal cord: insights from DNA microarrays," Trends Neurosci., 26(10): 555-563, 2003.
Bartholdi et al., "Expression of pro-inflammatory cytokine and chemokine mRNA upon experimental spinal cord injury in mouse: an in situ hybridization study," Eur. J. Neurosci., 9(7): 1422-1438, 1997.
Csanady et al., "Ca(2+)- and voltage-dependent gating of Ca(2+)- and ATP-sensitive cationic channels in brain capillary endothelium," Biophys. J., 85: 313-327, 2003.
Chen, et al., "Functional Coupling between Sulfonylurea Receptor Type 1 and a Nonselective Cation Channel in Reactive Astrocytes from Adult Rat Brain," J. Neurosci., 23: 8568-8577, 2003.
Copin et al., "70-kDa heat shock protein expression in cultured rat astrocytes after hypoxia: regulatory effect of almitrine," Neurochem. Res., 20(1): 11-15, 1995.
Currie et al., "Benign focal ischemic preconditioning induces neuronal Hsp70 and prolonged astrogliosis with expression of Hsp27," Brain Res., 863(1-2): 169-181, 2000.
Fujita et al., "Molecular aspects of ATP-sensitive K+ channels in the cardiovascular system and K+ channel openers," Pharmacol. Ther., 85: 39-53, 2000.
Inagaki et al., "A family of sulfonylurea receptors determines the pharmacological properties of ATP-sensitive K+ channels," Neuron, 16: 1011-1017, 1996.
Isomoto et al., "A novel sulfonylurea receptor forms with BIR (Kir6.2) a smooth muscle type ATP-sensitive K+ channel," J. Biol. Chem., 271: 24321-24324, 1996.
Kakimura et al., "Microglial activation and amyloid-beta clearance induced by exogenous heat-shock proteins," FASEB J., 16(6): 601-603, 2002.

Lee et al., "Differential neuroprotection from human heat shock protein 70 overexpression in in vitro and in vivo models of ischemia and ischemia-like conditions," Exp. Neurol., 170(1): 129-139, 2001.
Matz et al., "Heme-oxygenase-1 induction in glia throughout rat brain following experimental subarachnoid hemorrhage," Brain Res., 713(1-2): 211-222.
Mautes et al., "Co-induction of HSP70 and heme oxygenase-1 in macrophages and glia after spinal cord contusion in the rat," Brain Res., 883(2): 233-237, 2000.
Mautes et al., "Sustained induction of heme oxygenase-1 in the traumatized spinal cord," Exp. Neurol., 166(2): 254-265, 2000.
Nichols et al., "Adenosine diphosphate as an intracellular regulator of insulin secretion," Science, 272: 1785-1787, 1996.
Papadopoulos et al., "Over-expression of HSP-70 protects astrocytes from combined oxygen-glucose deprivation," Neuroreport, 7(2): 429-432, 1996.
Regan et al., "Herne oxygenase-1 induction protects murine cortical astrocytes from hemoglobin toxicity," Neurosci. Lett, 282(1-2): 1-4, 2000.
Shyng et al., "Regulation of KATP channel activity by diazoxide and MgADP. Distinct functions of the two nucleotide binding folds of the sulfonylurea receptor," J. Gen. Physiol., 110: 643-654, 1997.
Song et al., "GeneChip analysis after acute spinal cord injury in rat," J. Neurochem., 79(4): 804-815, 2001.
Xu et al., "HSP70 protects murine astrocytes from glucose deprivation injury," Neurosci. Lett., 224(1): 9-12, 1997.
Chen et al., "A Calcium-Activated Nonspecific Cation Channel in Reactive Astrocytes from Adult Rat Brain," Society for Neuroscience Abstracts, vol. 26, No. 1-2, Abstract No. 791.1, 2000 [abstract].
Simard, et al., "Regulation by Sulfanylurea Receptor Type 1 of a Non-selective Cation Channel Involved in Cytotoxic Edema of Reactive Astrocytes," J. Neurosurg. Anesthesiol., 16(1): 98-9, 2004.
Suarez-Isla, B., et al. "Single-Channel Recordings from Purified Acetylcholine Receptors Reconstitute in Bilayers Formed at the Tip of Patch Pipets, " American Chemical Society (1983) pp. 2319-2323.
Ansel el al., "Pharmaceutical Dosage Forms and Drug Delivery Systems" Lippincott Williams & Wilkins, 1999, pp. 48-53.
European Office Action, issued in European Application No. 08 771 576.9, dated Aug. 8, 2011.
International Preliminary Report on Patentability, dated Jan. 7, 2010 (published Jan. 7, 2010) during the prosecution of International Application No. PCT/US2008/067640.
International Preliminary Report on Patentability, dated Mar. 31, 2011, during prosection of International Application No. PCT/US2009/057111.
International Search Report, dated Jan. 2, 2009 (published Jan. 2, 2009) during the prosecution of International Application No. PCT/US2008/067640.
Japanese Office Action, issued in Japanese Patent Application No. 2007-532321, dated Apr. 22, 2011.
Japanese Office Action, issued in Japanese Patent Application No. 2007-532507, dated Jun. 20, 2011.
Lindblad and Melander, "Sulphonylurea dose-response relationships: relation to clinical practice", Diabetes, Obesity and Metabolism, 2000, No. 2, pp. 25-31, Blackwell Science Ltd.
Office Action dated Mar. 7, 2018 during prosecution of U.S. Appl. No. 15/179,696.
Restriction Requirement dated Aug. 28, 2017 during prosecution of U.S. Appl. No. 15/179,696.
Simard et al., "Drugs acting on SUR1 to treat CNS ischemia and trauma", Current Opinion in Pharmacology, 8:42-49, 2008.

* cited by examiner

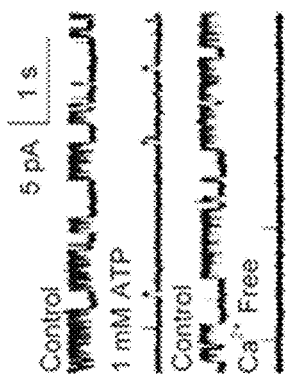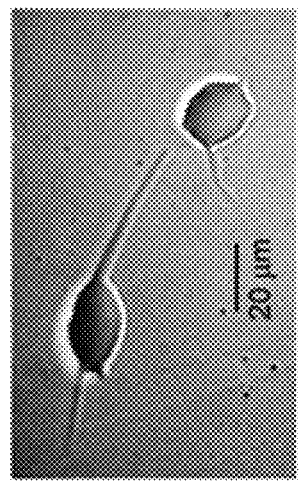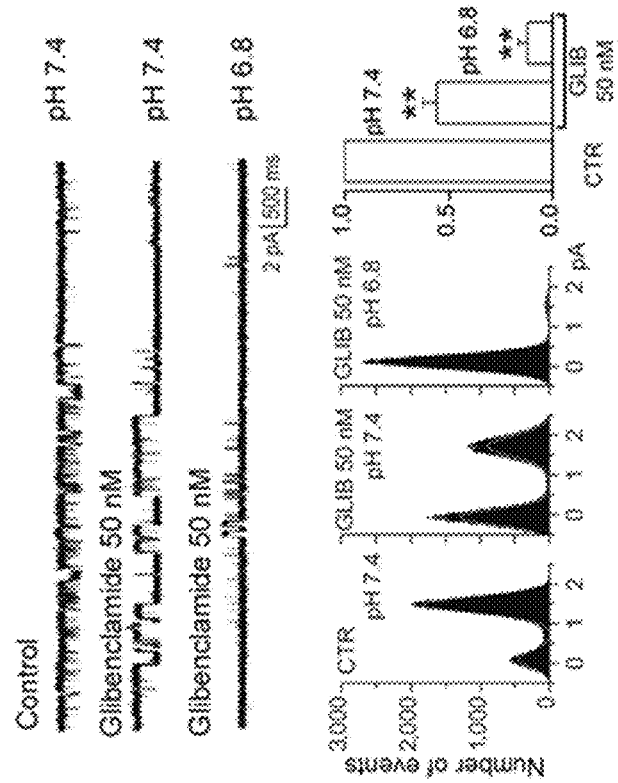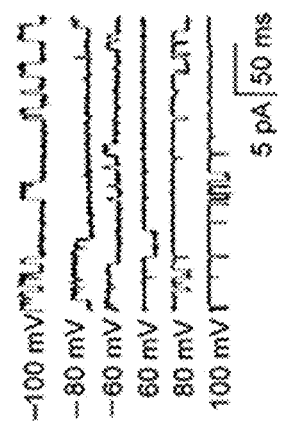

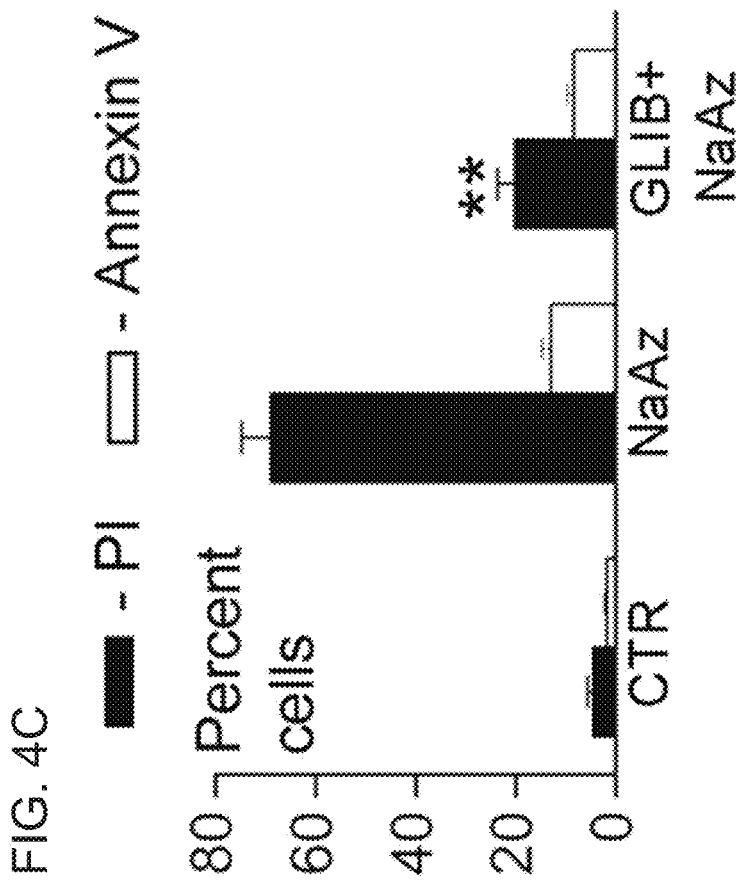
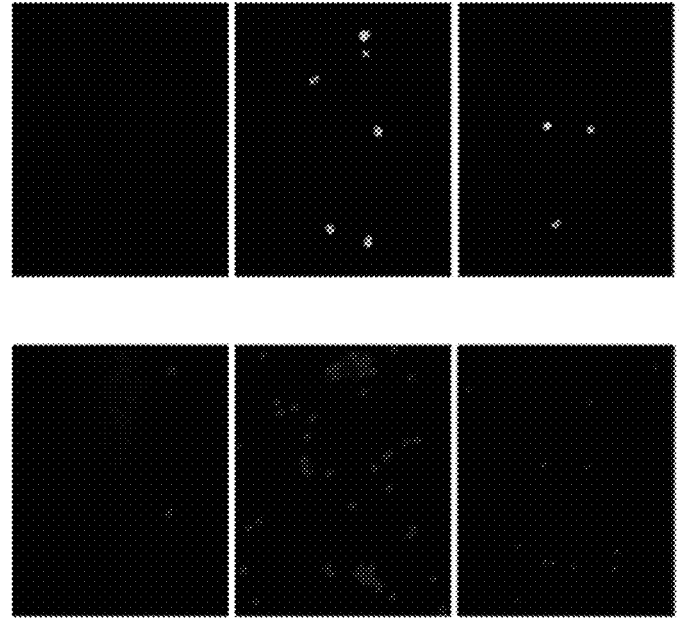
FIG. 4A  FIG. 4B  FIG. 4C

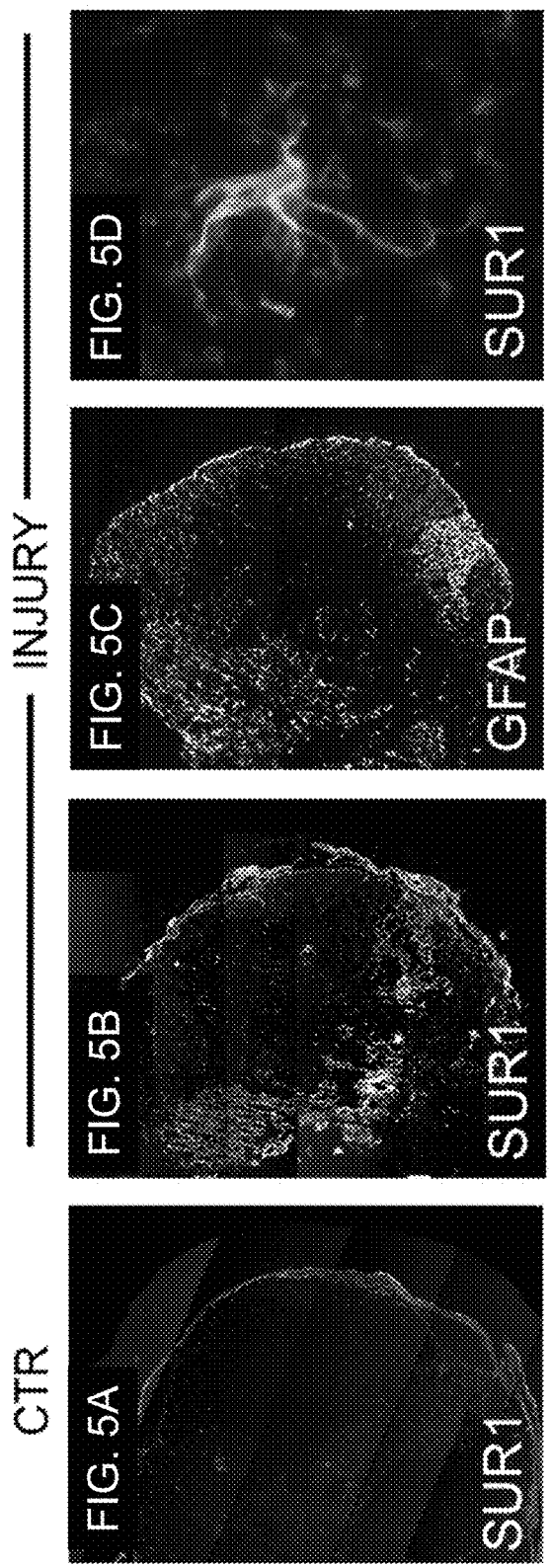

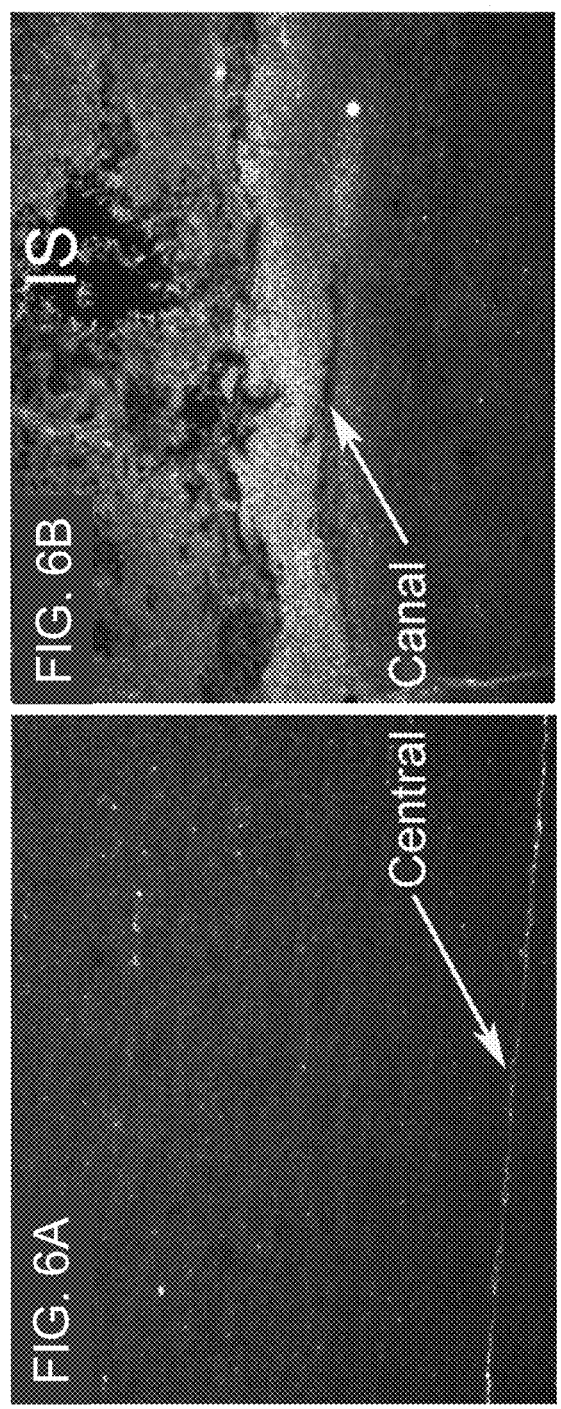

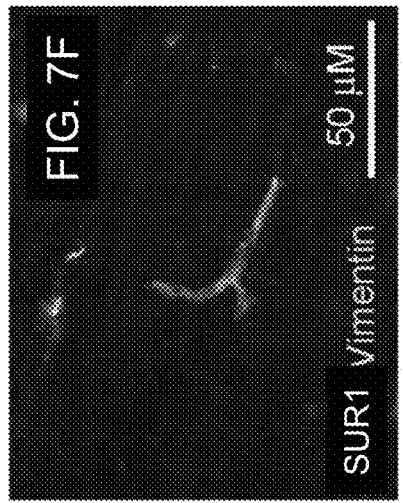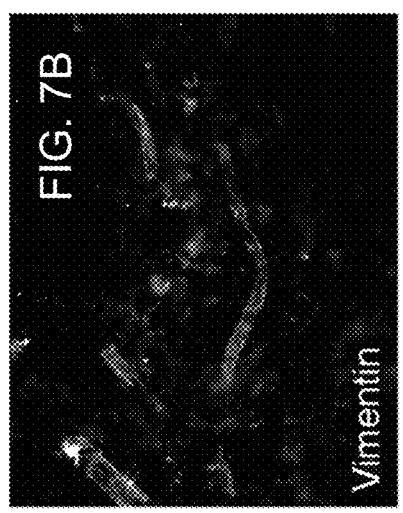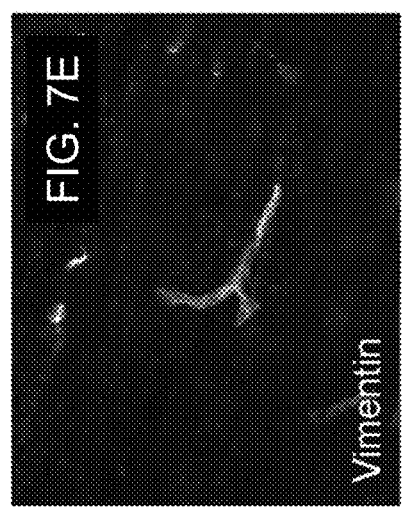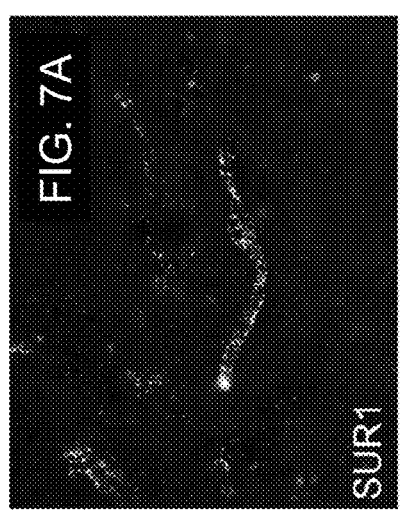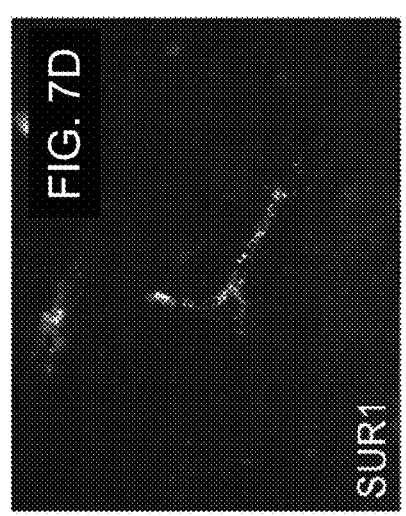

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: synthetic primer

<400> SEQUENCE: 1
cggaccaccc caagtattca                                               20

<210> SEQ ID NO 2
<211> LENGTH: 17
<212> TYPE: DNA
<213> ORGANISM: Artificial Sequence
<220> FEATURE:
<223> OTHER INFORMATION: synthetic primer

<400> SEQUENCE: 2
gccggcacgg ttcttct                                                  17

<210> SEQ ID NO 3
<211> LENGTH: 25
<212> TYPE: DNA
<213> ORGANISM: Artificial Sequence
<220> FEATURE:
<223> OTHER INFORMATION: synthetic primer

<400> SEQUENCE: 3
catgatcgtg gctgctatcc aggca                                         25

<210> SEQ ID NO 4
<211> LENGTH: 19
<212> TYPE: DNA
<213> ORGANISM: Artificial Sequence
<220> FEATURE:
<223> OTHER INFORMATION: synthetic primer

<400> SEQUENCE: 4
gagtcggact tctcgccct                                                19

<210> SEQ ID NO 5
<211> LENGTH: 20
<212> TYPE: DNA
<213> ORGANISM: Artificial Sequence
<220> FEATURE:
<223> OTHER INFORMATION: synthetic primer

<400> SEQUENCE: 5
ccttgacagt ggaccgaacc                                               20

<210> SEQ ID NO 6
<211> LENGTH: 25
<212> TYPE: DNA
<213> ORGANISM: Artificial Sequence
<220> FEATURE:
<223> OTHER INFORMATION: synthetic primer
```

-continued

```
<400> SEQUENCE: 6
ttccacatcc tggtcacacc gctgt                                          25

<210> SEQ ID NO 7
<211> LENGTH: 17
<212> TYPE: DNA
<213> ORGANISM: Artificial Sequence
<220> FEATURE:
<223> OTHER INFORMATION: synthetic primer

<400> SEQUENCE: 7
aagcacgtca acgccct                                                   17

<210> SEQ ID NO 8
<211> LENGTH: 19
<212> TYPE: DNA
<213> ORGANISM: Artificial Sequence
<220> FEATURE:
<223> OTHER INFORMATION: synthetic primer

<400> SEQUENCE: 8
gaagcttttc cggcttgtc                                                 19
```

TARGETING NC$_{Ca-ATP}$ CHANNEL FOR ORGAN PROTECTION FOLLOWING ISCHEMIC EPISODE

This application is a continuation of U.S. NonProvisional patent application Ser. No. 12/522,444 filed Jan. 27, 2010, now U.S. Pat. No. 9,511,075; which is a national phase application under 35 U.S.C. § 371 that claims priority to International Application No. PCT/US2008/050922 filed Jan. 11, 2008; which claims priority to U.S. Provisional Patent Application No. 60/880,119 filed Jan. 12, 2007; U.S. Provisional Patent Application No. 60/923,378 filed Apr. 13, 2007; U.S. Provisional Patent Application No. 60/952,396 filed Jul. 27, 2007; and U.S. Provisional Patent Application No. 61/012,613 filed Dec. 10, 2007, all of which applications are incorporated by reference herein in their entirety.

STATEMENT REGARDING FEDERALLY SPONSORED RESEARCH OR DEVELOPMENT

This invention was made with government support under Grant Numbers HL082517, HL051932, and NS048260 awarded by the National Institutes of Health and VA Merit Grant Number 003-40-4111 awarded by the United States Department of Veterans Affairs. The government has certain rights in the invention.

FIELD OF THE INVENTION

The present invention generally relates to the fields of cell biology, molecular biology, physiology, and medicine. In particular, the present invention relates to a novel non-selective monovalent cationic ATP-sensitive ion channel (hereinafter referred to as the NC$_{Ca-ATP}$ channel) that is coupled to sulfonylurea receptor type 1 in cells, including, for example, endothelial cells. The present invention also relates to therapy, including combination therapy, employing compounds and treatments that modulate NC$_{Ca-ATP}$ channel activity and to kits including compounds useful for treatment of disease or injury conditions, such as, for example, ischemia/hypoxia injury, organ transplantation, and trauma.

BACKGROUND OF THE INVENTION

Injury to vital organs, such as, for example, the heart, brain, lungs, kidneys, gastrointestinal tract, or liver, has serious and even life-threatening consequences as does damage to cells and tissues which include, for example, cornea, retina, bone, heart valves, tendons, ligaments, cartilage, vasculature, skin, bone marrow, blood cells, stem cells, and other tissues and cells derived from the body. Following injurious events, such as ischemia/hypoxia (e.g., a consequence of a heart attack, a stroke, tachycardia, atherosclerosis, hypotension (e.g. in septic shock, heart failure), thromboembolism (e.g. pulmonary embolism), outside compression of a blood vessel (e.g. by a tumor), foreign bodies in the circulation (e.g. amniotic fluid in amniotic fluid embolism), sickle cell disease, hemorrhage, or rupture of a vessel (e.g. aortic aneurysm rupture), or organ transplantation) cellular damage ensues. For example, following a stroke, the normal response of the surrounding brain is to mount a cellular response that includes formation of reactive astrocytes that are believed to be important to "contain" and "clean-up" the injury site. Swelling of neural cells is part of the cytotoxic or cell swelling response that characterizes brain damage in cerebral ischemia and traumatic brain injury, and is a major cause of morbidity and mortality. See, Staub et al., 1993; Kimelberg et al., 1995. A number of mediators have been identified that initiate swelling of neural cells, including elevation of extracellular K$^+$, acidosis, release of neurotransmitters and free fatty acids. See, Kempski et al., 1991; Rutledge and Kimelberg, 1996; Mongin et al., 1999. Cytotoxic edema is a well-recognized phenomenon clinically that causes brain swelling, which worsens outcome and increases morbidity and mortality in brain injury and stroke.

Secondary Injury—Progressive Hemorrhagic Necrosis (PHN)

Delayed injury is an important phenomenon and represents a potential therapeutic target for ischemia/hypoxia associated injuries. The concept of delayed or secondary injury following, for example, ischemia/hypoxia, arises from the observation that the volume of injured tissue increases with time after injury, i.e., the lesion itself expands and evolves over time. Whereas primary injured tissues are irrevocably damaged from the very beginning, for example, following ischemia/hypoxia, tissues that are destined to become "secondarily" injured are considered to be potentially salvageable. An example of secondary injury in spinal cord injury (SCI) has been described and reviewed in a paper by Tator (1991), as well as in more recent reviews (Kwon et al., 2004), wherein the overall concept of secondary injury is validated. Older observations based on histological studies that gave rise to the concept of lesion-evolution have been confirmed with non-invasive MRI (Bilgen et al., 2000; Ohta et al., 1999; Sasaki et al., 1978; Weirich et al., 1990).

Mechanisms of delayed hemorrhage and PHN

Tator and Koyanagi (1997) expressed the view that obstruction of small intramedullary vessels by the initial mechanical stress or secondary injury may be responsible for PHN. Kawata and colleagues (1993) attributed the progressive changes to leukocyte infiltration around the injured area leading to plugging of capillaries. Most importantly, damage to the endothelium of spinal cord capillaries and postcapillary venules has been regarded as a major factor in the pathogenesis of PHN (Griffiths et al., 1978; Kapadia, 1984; Nelson et al., 1977). Endothelial dysfunction and damage has also been attributed to myocardial ischemic events (Verma et al. Circulation. 2002; 105:2332). The notion that the endothelium is involved in ischemia/hypoxia injury is essentially certain and represents a viable therapeutic target for protection against ischemia/hypoxia associated injuries. However, no molecular mechanism for progressive dysfunction of endothelium has heretofore been identified.

"Hemorrhagic conversion" is a term familiar in the ischemia/hypoxia injury literature. Hemorrhagic conversion describes the process of conversion from a bland infarct into a hemorrhagic infarct, and is typically associated with post-ischemic reperfusion, either spontaneous or induced by thrombolytic therapy. The molecular pathology involved in hemorrhagic conversion has yet to be fully elucidated, but considerable work has implicated enzymatic destruction of capillaries by matrix-metalloproteinases (MMP) released by invading neutrophils (Gidday et al., 2005; Justicia et al., 2003; Lorenzl et al., 2003; Romanic et al., 1998). Maladaptive activation of MMP compromises the structural integrity of capillaries. In ischemic stroke, MMP inhibitors reduce hemorrhagic conversion following thrombolytic-induced reperfusion (PMID 15459442 and 11898581). Additionally, MMP inhibitors are effective against myocardial ischemic events (Creemers et al., Circ Res. 2001 Aug. 3; 89(3):201-10).

An alternative mechanism that gives rise to PHN and post ischemic injury involves expression and activation of $NC_{Ca\text{-}ATP}$ channels (see Simard et al., 2007). The data demonstrate that cells that express the $NC_{Ca\text{-}ATP}$ channel following an ischemic or other injury-stimulus, later undergo oncotic (necrotic) cell death when ATP is depleted. This is shown explicitly for astrocytes (Simard et al., 2006), and in specific embodiments it also occurs with capillary endothelial cells that express the channel. It follows that if capillary endothelial cells undergo this process leading to necrotic death, capillary integrity would be lost, leading to extravasation of blood and formation of petechial hemorrhages.

However, no treatment has been reported that reduces PHN and ischemia/hypoxia associated injury with the highly selective SUR1 antagonists, glibenclamide and repaglinide, as well as with antisense-oligodeoxynucleotide (AS-ODN) directed against SUR1. It is useful that the molecular mechanisms targeted by these 3 agents—SUR1 and the SUR1-regulated $NC_{Ca\text{-}ATP}$ channel, are characterized to further elucidate their role in PHN.

Other and further objects, features, and advantages will be apparent from the following description of the present exemplary embodiments of the invention, which are given for the purpose of disclosure.

SUMMARY OF THE INVENTION

The present invention concerns a specific channel, the $NC_{Ca\text{-}ATP}$ channel, which is expressed, for example, in cells, including, for example, neurons, glia, and endothelial cells and in tissues, including for example, cornea, retina, bone, heart valves, muscle, tendons, ligaments, cartilage, vasculature, skin, bone marrow, blood cells, stem cells, and other non-CNS tissues and cells derived from the body following, for example, trauma or ischemia/hypoxia. This unique non-selective cation channel is activated by intracellular calcium and blocked by intracellular ATP ($NC_{Ca\text{-}ATP}$ channel), and can be expressed in non-neural cells and in neural cells, such as neuronal cells, neuroglia cells (also termed glia, or glial cells, e.g., astrocyte, ependymal cell, oligodentrocyte and microglia) or endothelial cells (e.g., capillary endothelial cells) in which the cells have been or are exposed to a traumatic insult, for example, an acute insult (e.g., hypoxia, ischemia, tissue compression, mechanical distortion, cerebral edema or cell swelling), toxic compounds or metabolites, an acute injury, cancer, brain abscess, etc.

More specifically, the $NC_{Ca\text{-}ATP}$ channel of the present invention has a single-channel conductance to potassium ion ($K^+$) between 20 and 50 pS at physiological potassium concentrations. The $NC_{Ca\text{-}ATP}$ channel is also stimulated by $Ca^{2+}$ on the cytoplasmic side of the cell membrane in a physiological concentration range, where calcium ion concentration range is from $10^{-8}$ to $10^{-5}$ M. The $NC_{Ca\text{-}ATP}$ channel is also inhibited by cytoplasmic ATP in a physiological concentration range, where the concentration range is from $10^{-1}$ to 5 mM. The $NC_{Ca\text{-}ATP}$ channel is also permeable to the following cations; $K^+$, $Cs^+$, $Li^+$, $Na^+$; to the extent that the permeability ratio between any two of the cations is greater than 0.5 and less than 2.

More particularly, the present invention relates to the regulation and/or modulation of this $NC_{Ca\text{-}ATP}$ channel and how its modulation can be used to treat various diseases and/or conditions, for example acute insults (e.g., an ischemic/hypoxic insult, a traumatic or mechanical injury) or chronic ischemia and diseases or conditions leading to organ dysfunction or organ failure. The present invention is also drawn to treating and/or preventing various non-CNS diseases and/or conditions by the regulation and/or modulation of an $NC_{Ca\text{-}ATP}$ channel disclosed herein. The modulation and/or regulation of the channel results from administration of an antagonist or inhibitor of the channel, in specific embodiments. Thus, depending upon the disease, a composition (an antagonist or inhibitor) is administered to block or inhibit at least in part the channel to prevent cell death, for example to treat edema that results from ischemia due to tissue trauma or to increased tissue pressure. In these instances, the channel is blocked to prevent or reduce or modulate, for example, depolarization of the cells.

In one aspect, the present invention provides novel methods of treating a patient comprising administering at least a therapeutic compound that targets a unique non-selective cation channel activated by intracellular calcium and blocked by intracellular ATP ($NC_{Ca\text{-}ATP}$ channel), alone or in combination with an additional therapeutic compound. In specific embodiments, the therapeutic compound that targets the channel may be an antagonist (such as a SUR1 inhibitor, for example) that is employed in therapies, such as treatment of ischemia or edema, benefiting from blocking and/or inhibiting the $NC_{Ca\text{-}ATP}$ channel. Additional compounds for the compositions of the invention include cation channel blockers, blockers of TRPM4 channels, such as, for example, flufenamic acid, mefanimic acid, niflumic acid, etc., and antagonists of VEGF, MMP, NOS, TNFα, NFκB, and/or thrombin, for example.

The invention also encompasses the use of such compounds in combinatorial compositions that at least in part modulate $NC_{Ca\text{-}ATP}$ channel activity to treat cell swelling, for example.

The invention also relates to ischemia/hypoxia associated events such as, for example, heart attack, a stroke, tachycardia, atherosclerosis, hypotension (e.g. in septic shock, heart failure), thromboembolism (e.g. pulmonary embolism), outside compression of a blood vessel (e.g. by a tumor), foreign bodies in the circulation (e.g. amniotic fluid in amniotic fluid embolism), sickle cell disease, hemorrhage, or rupture of a vessel (e.g. aortic aneurysm rupture) and organ transplantation and treatments to reduce damage to heart and other organs following heart attack or other ischemic or hypoxic/ischemic events, including reducing damage to, or preserving the integrity and function of an organ in life or following removal of an organ for transplantation. Treatments in these aspects of the invention include administration of a compound or compounds to inhibit the activity of $NC_{Ca\text{-}ATP}$ channels, such as, for example, SUR1 antagonists, and/or TRPM4 channel antagonists, and may also include combination treatments with for example, SUR1 antagonists, and/or TRPM4 channel antagonists, in combination with one or more additional therapeutic compound(s), as discussed above (e.g., cation channel blockers, blockers of TRPM4 channels, such as, for example, flufenamic acid, mefanimic acid, niflumic acid, etc., and antagonists of VEGF, MMP, NOS, TNFα, NFκB, and/or thrombin). Organs and tissues that may be treated, preserved, and/or protected by the methods and compositions of the invention include, for example, heart, liver, lung, kidney, blood vessel, gastrointestinal tract organs such as intestine, cornea, and other organs and tissues, including connective tissue such as, for example, ligaments and tendons.

Further provided is a method of preventing cellular swelling and the resulting cellular damage through the therapeutic use of antagonists to the $NC_{Ca\text{-}ATP}$ channel, alone or in combination with an additional therapeutic compound.

In one embodiment, the therapeutic composition can be administered to a cell or organ of the body. Such administration an organ includes injection directly into the organ. The invention further provides the therapeutic use of sulfonylurea compounds, for example, as antagonists to the $NC_{Ca\text{-}ATP}$ channel to prevent cell swelling or to prevent and/or treat one or more ischemic episodes. In one embodiment, the sulfonylurea compound is glibenclamide. In another embodiment, the sulfonylurea compound is tolbutamide, or any of the other compounds that have been found to promote insulin secretion by acting on $K_{ATP}$ channels in pancreatic β cells, as listed elsewhere herein.

The invention also encompasses antagonists of the $NC_{Ca\text{-}ATP}$ channel, including small molecules, large molecules, and antibodies, as well as nucleotide sequences that can be used to inhibit $NC_{Ca\text{-}ATP}$ channel gene expression or expression of any of its subunit components (e.g., antisense and ribozyme molecules). An antagonist of the $NC_{Ca\text{-}ATP}$ channel includes one or more compounds capable of (1) blocking the channel; (2) preventing channel opening; (3) reducing the magnitude of membrane current through the channel; (4) inhibiting transcriptional expression of the channel or of its subunits; and/or (5) inhibiting post-translational assembly and/or trafficking of channel subunits.

The composition(s) of the present invention may be delivered alimentarily or parenterally, for example. Examples of alimentary administration include, but are not limited to orally, buccally, rectally, or sublingually. Parenteral administration can include, but are not limited to intramuscularly, subcutaneously, intraperitoneally, intravenously, intratumorally, intraarterially, intraventricularly, intracavity, intravesical, intrathecal, or intrapleural. The compound can be administered alimentary (e.g., orally, buccally, rectally or sublingually); parenterally (e.g., intravenously, intradermally, intramuscularly, intraarterially, intrathecally, subcutaneously, intraperitoneally, intraventricularly); by intracavity; intravesically; intrapleurally; and/or topically (e.g., transdermally), mucosally, or by direct injection into the brain parenchyma. Other modes of administration may also include topically, mucosally, transdermally, or direct injection into the brain parenchyma, for example.

An effective amount of an inhibitor of $NC_{Ca\text{-}ATP}$ channel that may be administered to an individual or a cell in a tissue or organ thereof includes a dose of about 0.0001 nM to about 2000 μM, for example. More specifically, doses of an antagonist to be administered are from about 0.01 nM to about 2000 μM; about 0.01 μM to about 0.05 μM; about 0.05 μM to about 1.0 μM; about 1.0 μM to about 1.5 μM; about 1.5 μM to about 2.0 μM; about 2.0 μM to about 3.0 μM; about 3.0 μM to about 4.0 μM; about 4.0 μM to about 5.0 μM; about 5.0 μM to about 10 μM; about 10 μM to about 50 μM; about 50 μM to about 100 μM; about 100 μM to about 200 μM; about 200 μM to about 300 μM; about 300 μM to about 500 μM; about 500 μM to about 1000 μM; about 1000 μM to about 1500 μM and about 1500 μM to about 2000 μM, for example. Of course, all of these amounts are exemplary, and any amount in-between these points is also expected to be of use in the invention.

An effective amount of an inhibitor of the $NC_{Ca\text{-}ATP}$ channel or related-compounds thereof as a treatment varies depending upon the host treated and the particular mode of administration. In one embodiment of the invention the dose range of the agonist or antagonist of the $NC_{Ca\text{-}ATP}$ channel or related-compounds thereof will be about 0.01 μg/kg body weight to about 20,000 μg/kg body weight.

In specific embodiments, the dosage is less than 0.8 mg/kg. In particular aspects, the dosage range may be from 0.005 mg/kg to 0.8 mg/kg body weight, 0.006 mg/kg to 0.8 mg/kg body weight, 0.075 mg/kg to 0.8 mg/kg body weight, 0.08 mg/kg to 0.8 mg/kg body weight, 0.09 mg/kg to 0.8 mg/kg body weight, 0.005 mg/kg to 0.75 mg/kg body weight, 0.005 mg/kg to 0.7 mg/kg body weight, 0.005 mg/kg to 0.65 mg/kg body weight, 0.005 mg/kg to 0.5 mg/kg body weight, 0.09 mg/kg to 0.8 mg/kg body weight, 0.1 mg/kg to 0.75 mg/kg body weight, 0.1 mg/kg to 0.70 mg/kg body weight, 0.1 mg/kg to 0.65 mg/kg body weight, 0.1 mg/kg to 0.6 mg/kg body weight, 0.1 mg/kg to 0.55 mg/kg body weight, 0.1 mg/kg to 0.5 mg/kg body weight, 0.1 mg/kg to 0.45 mg/kg body weight, 0.1 mg/kg to 0.4 mg/kg body weight, 0.1 mg/kg to 0.35 mg/kg body weight, 0.1 mg/kg to 0.3 mg/kg body weight, 0.1 mg/kg to 0.25 mg/kg body weight, 0.1 mg/kg to 0.2 mg/kg body weight, or 0.1 mg/kg to 0.15 mg/kg body weight, for example.

In specific embodiments, the dosage range may be from 0.2 mg/kg to 0.8 mg/kg body weight, 0.2 mg/kg to 0.75 mg/kg body weight, 0.2 mg/kg to 0.70 mg/kg body weight, 0.2 mg/kg to 0.65 mg/kg body weight, 0.2 mg/kg to 0.6 mg/kg body weight, 0.2 mg/kg to 0.55 mg/kg body weight, 0.2 mg/kg to 0.5 mg/kg body weight, 0.2 mg/kg to 0.45 mg/kg body weight, 0.2 mg/kg to 0.4 mg/kg body weight, 0.2 mg/kg to 0.35 mg/kg body weight, 0.2 mg/kg to 0.3 mg/kg body weight, or 0.2 mg/kg to 0.25 mg/kg body weight, for example.

In further specific embodiments, the dosage range may be from 0.3 mg/kg to 0.8 mg/kg body weight, 0.3 mg/kg to 0.75 mg/kg body weight, 0.3 mg/kg to 0.70 mg/kg body weight, 0.3 mg/kg to 0.65 mg/kg body weight, 0.3 mg/kg to 0.6 mg/kg body weight, 0.3 mg/kg to 0.55 mg/kg body weight, 0.3 mg/kg to 0.5 mg/kg body weight, 0.3 mg/kg to 0.45 mg/kg body weight, 0.3 mg/kg to 0.4 mg/kg body weight, or 0.3 mg/kg to 0.35 mg/kg body weight, for example.

In specific embodiments, the dosage range may be from 0.4 mg/kg to 0.8 mg/kg body weight, 0.4 mg/kg to 0.75 mg/kg body weight, 0.4 mg/kg to 0.70 mg/kg body weight, 0.4 mg/kg to 0.65 mg/kg body weight, 0.4 mg/kg to 0.6 mg/kg body weight, 0.4 mg/kg to 0.55 mg/kg body weight, 0.4 mg/kg to 0.5 mg/kg body weight, or 0.4 mg/kg to 0.45 mg/kg body weight, for example.

In specific embodiments, the dosage range may be from 0.5 mg/kg to 0.8 mg/kg body weight, 0.5 mg/kg to 0.75 mg/kg body weight, 0.5 mg/kg to 0.70 mg/kg body weight, 0.5 mg/kg to 0.65 mg/kg body weight, 0.5 mg/kg to 0.6 mg/kg body weight, or 0.5 mg/kg to 0.55 mg/kg body weight, for example. In specific embodiments, the dosage range may be from 0.6 mg/kg to 0.8 mg/kg body weight, 0.6 mg/kg to 0.75 mg/kg body weight, 0.6 mg/kg to 0.70 mg/kg body weight, or 0.6 mg/kg to 0.65 mg/kg body weight, for example. In specific embodiments, the dosage range may be from 0.7 mg/kg to 0.8 mg/kg body weight or 0.7 mg/kg to 0.75 mg/kg body weight, for example. In specific embodiments the dose range may be from 0.001 mg/day to 3.5 mg/day. In other embodiments, the dose range may be from 0.001 mg/day to 10 mg/day. In other embodiments, the dose range may be from 0.001 mg/day to 20 mg/day.

Further, those of skill will recognize that a variety of different dosage levels will be of use, for example, 0.0001 μg/kg, 0.0002 μg/kg, 0.0003 μg/kg, 0.0004 μg/kg, 0.005 μg/kg, 0.0007 μg/kg, 0.001 μg/kg, 0.1 μg/kg, 1.0 μg/kg, 1.5 μg/kg, 2.0 μg/kg, 5.0 μg/kg, 10.0 μg/kg, 15.0 μg/kg, 30.0 μg/kg, 50 μg/kg, 75 μg/kg, 80 μg/kg, 90 μg/kg, 100 μg/kg, 120 μg/kg, 140 μg/kg, 150 μg/kg, 160 μg/kg, 180 μg/kg, 200 μg/kg, 225 μg/kg, 250 μg/kg, 275 μg/kg, 300 μg/kg, 325

µg/kg, 350 µg/kg, 375 µg/kg, 400 µg/kg, 450 µg/kg, 500 µg/kg, 550 µg/kg, 600 µg/kg, 700 µg/kg, 750 µg/kg, 800 µg/kg, 900 µg/kg, 1 mg/kg, 5 mg/kg, 10 mg/kg, 12 mg/kg, 15 mg/kg, 20 mg/kg, and/or 30 mg/kg. In particular embodiments, there may be dosing of from very low ranges (e.g. 1 mg/kg/day or less; 5 mg/kg bolus; or 1 mg/kg/day) to moderate doses (e.g. 2 mg bolus, 15 mg/day) to high doses (e.g. 5 mg bolus, 30-40 mg/day; and even higher). Of course, all of these dosages are exemplary, and any dosage in-between these points is also expected to be of use in the invention. Any of the above dosage ranges or dosage levels may be employed for an agonist or antagonist, or both, of $NC_{Ca\text{-}ATP}$ channel or related-compounds thereof.

An effective amount of a therapeutic composition of the invention, including an antagonist of $NC_{Ca\text{-}ATP}$ channel and/or the additional therapeutic compound, that may be administered to a cell includes a dose of about 0.0001 nM to about 2000 µM, for example. More specifically, doses to be administered are from about 0.01 nM to about 2000 µM; about 0.01 µM to about 0.05 □µM; about 0.05 µM to about 1.0 µM; about 1.0 µM to about 1.5 µM; about 1.5 µM to about 2.0 µM; about 2.0 □µM to about 3.0 µM; about 3.0 µM to about 4.0 µM; about 4.0 µM to about 5.0 µM; about 5.0 µM to about 10 µM; about 10 µM to about 50 µM; about 50 µM to about 100 µM; about 100 µM to about 200 µM; about 200 µM to about 300 µM; about 300 □µM to about 500 µM; about 500 µM to about 1000 µM; about 1000 µM to about 1500 µM and about 1500 µM to about 2000 µM, for example. Of course, all of these amounts are exemplary, and any amount in-between these points is also expected to be of use in the invention.

An effective amount of an antagonist of the $NC_{Ca\text{-}ATP}$ channel or related-compounds thereof as a treatment varies depending upon the host treated and the particular mode of administration. In one embodiment of the invention, the dose range of the therapeutic combinatorial composition of the invention, including an antagonist of $NC_{Ca\text{-}ATP}$ channel and/or the additional therapeutic compound, is about 0.01 µg/kg body weight to about 20,000 µg/kg body weight. The term "body weight" is applicable when an animal is being treated. When isolated cells are being treated, "body weight" as used herein should read to mean "total cell body weight". The term "total body weight" may be used to apply to both isolated cell and animal treatment. All concentrations and treatment levels are expressed as "body weight" or simply "kg" in this application are also considered to cover the analogous "total cell body weight" and "total body weight" concentrations. However, those of skill will recognize the utility of a variety of dosage range, for example, 0.01 µg/kg body weight to 20,000 µg/kg body weight, 0.02 µg/kg body weight to 15,000 µg/kg body weight, 0.03 µg/kg body weight to 10,000 µg/kg body weight, 0.04 µg/kg body weight to 5,000 µg/kg body weight, 0.05 µg/kg body weight to 2,500 µg/kg body weight, 0.06 µg/kg body weight to 1,000 µg/kg body weight, 0.07 µg/kg body weight to 500 µg/kg body weight, 0.08 µg/kg body weight to 400 µg/kg body weight, 0.09 µg/kg body weight to 200 µg/kg body weight or 0.1 µg/kg body weight to 100 µg/kg body weight. Further, those of skill will recognize that a variety of different dosage levels are of use, for example, 0.0001 µg/kg, 0.0002 µg/kg, 0.0003 µg/kg, 0.0004 µg/kg, 0.005 µg/kg, 0.0007 µg/kg, 0.001 µg/kg, 0.1 µg/kg, 1.0 µg/kg, 1.5 µg/kg, 2.0 µg/kg, 5.0 µg/kg, 10.0 µg/k g, 15.0 µg/kg, 30.0 µg/kg, 50 µg/kg, 75 µg/kg, 80 µg/kg, 90 µg/kg, 100 µg/kg, 120 µg/kg, 140 µg/kg, 150 µg/kg, 160 µg/kg, 180 µg/kg, 200 µg/kg, 225 µg/kg, 250 µg/kg, 275 □µg/kg, 300 µg/kg, 325 µg/kg, 350 µg/kg, 375 µg/kg, 400 µg/kg, 450 µg/kg, 500 µg/kg, 550 µg/kg, 600 µg/kg, 700 µg/kg, 750 µg/kg, 800 µg/kg, 900 µg/kg, 1 mg/kg, 5 mg/kg, 10 mg/kg, 12 mg/kg, 15 mg/kg, 20 mg/kg, and/or 30 mg/kg.

In particular embodiments, there may be dosing of from very low ranges (e.g. for glyburide 1 mg/day or less) to moderate doses (e.g. 3.5 mg/day) to high doses (e.g. 10-40 mg/day; and even higher). Of course, all of these dosages are exemplary, and any dosage in-between these points is also expected to be of use in the invention. Any of the above dosage ranges or dosage levels may be employed for an agonist or antagonist, or both, of $NC_{Ca\text{-}ATP}$ channel or related-compounds thereof.

In certain embodiments, the amount of the combinatorial therapeutic composition administered to the subject is in the range of about 0.0001 µg/kg/day to about 20 mg/kg/day, about 0.01 µg/kg/day to about 100 µg/kg/day, or about 100 µg/kg/day to about 20 mg/kg/day. Still further, the combinatorial therapeutic composition may be administered to the subject in the form of a treatment in which the treatment may comprise the amount of the combinatorial therapeutic composition or the dose of the combinatorial therapeutic composition that is administered per day (1, 2, 3, 4, etc.), week (1, 2, 3, 4, 5, etc.), month (1, 2, 3, 4, 5, etc.), etc. Treatments may be administered such that the amount of combinatorial therapeutic composition administered to the subject is in the range of about 0.0001 µg/kg/treatment to about 20 mg/kg/treatment, about 0.01 µg/kg/treatment to about 100 µg/kg/treatment, or about 100 µg/kg/treatment to about 20 mg/kg/treatment.

A typical dosing regime consists of a loading dose designed to reach a target agent plasma level followed by an infusion of up to 7 days to maintain that target level. One skilled in the art will recognize that the pharmacokinetics of each agent will determine the relationship between the load dose and infusion rate for a targeted agent plasma level. In one example, for intravenous glyburide administration, a 15.7 µg bolus (also called a loading dose) is followed by a maintenance dose of 0.3 µg/min (432 µg/day) for 120 hours (5 days). This dose regime is predicted to result in a steady-state plasma concentration of 4.07 ng/mL. In another example for intravenous glyburide, a 117 µg bolus dose is followed by a maintenance dose of 2.1 µg/min (3 mg/day) for 3 days. This dose is predicted to result in a steady-state plasma concentration of 28.3 ng/mL. In yet another example for glyburide, a 665 µg bolus dose is followed by a maintenance dose of 11.8 µg/min (17 mg/day) for 120 hours (5 days). This dose is predicted to result in a steady-state plasma concentration of 160.2 ng/mL. Once the pharmacokinetic parameters for an agent are known, loading dose and infusion dose for any specified targeted plasma level can be calculated. As an illustrative case for glyburide, the bolus is generally 30-90 times, for example 40-80 times, such as 50-60 times, the amount of the maintenance dose, and one of skill in the art can determine such parameters for other compounds based on the guidance herein.

In some embodiments of the invention, several pathways to cell death are involved in ischemia/hypoxia, which require monovalent or divalent cation influx, implicating non-selective cation (NC) channels. NC channels are also likely to be involved in the dysfunction of vascular endothelial cells that leads to formation of edema following cerebral and other forms of ischemia/hypoxia. Non-specific blockers of NC channels, including pinokalant (LOE 908 MS) and rimonabant (SR141716A), have beneficial effects in rodent models of ischemic stroke.

In other embodiments of the invention, focal and global ischemia and post-ischemic reperfusion (e.g., in the heart and other organs including, for example, the liver, lungs, brain, spinal cord, kidneys, cornea, organs of the gastrointestinal tract, and other organs of the body susceptible to ischemia) cause capillary dysfunction, resulting in edema formation and hemorrhagic conversion. In specific embodiments, the invention generally concerns the central role of Starling's principle, which states that edema formation is determined by the "driving force" and capillary "permeability pore". In particular aspects related to the invention, movements of fluids are driven largely without new expenditure of energy by the ischemic tissue. In one embodiment, the progressive changes in osmotic and hydrostatic conductivity of abnormal capillaries is organized into 3 phases: formation of ionic edema, formation of vasogenic edema, and catastrophic failure with hemorrhagic conversion. In particular embodiments, ischemia-induced capillary dysfunction is attributed to de novo synthesis of a specific ensemble of proteins that determine the terms for osmotic and hydraulic conductivity in Starling's equation, and whose expression is driven by a distinct transcriptional program.

The $NC_{Ca-ATP}$ channel can be inhibited by an $NC_{Ca-ATP}$ channel inhibitor, an $NC_{CaATP}$ channel blocker, a type 1 sulfonylurea receptor (SUR1) antagonist, SUR1 inhibitor, or a compound capable of reducing the magnitude of membrane current through the channel, for example. More specifically, the exemplary SUR1 antagonist may be selected from the group consisting of glibenclamide, tolbutamide, repaglinide, nateglinide, meglitinide, mitiglinide, iptakalim, endosulfines, LY397364, LY389382, gliclazide, glipizide, gliquidone, chlorpropamide, glimepiride, estrogen, estrogen related-compounds (estradiol, estrone, estriol, genistein, non-steroidal estrogen (e.g., diethystilbestrol), phytoestrogen (e.g., coumestrol), zearalenone, etc.), and compounds known to inhibit or block $K_{ATP}$ channels. MgADP can also be used to inhibit the channel. Other compounds that can be used to block or inhibit $K_{ATP}$ channels include, but are not limited to tolbutamide, glyburide (1[p-2[5-chloro-O-anisamido)ethyl] phenyl] sulfonyl]-3-cyclohexyl-3-urea); chloropropamide (1-[[(p-chlorophenyl)sulfonyl]-3-propylurea; glipizide (1-cyclohexyl-3[[p-[2(5-methylpyrazine carboxamido)ethyl] phenyl] sulfonyl] urea); or tolazamide(benzenesulfonamide-N-[[(hexahydro-1H-azepin-1yl)amino] carbonyl]-4-methyl). Exemplary inhibitors may be selected from the group consisting of glibenclamide; tolbutamide; glyburide (1[p-2[5-chloro-O-anisamido)ethyl]phenyl] sulfonyl]-3-cyclohexyl-3-urea); chloropropamide (1-[[(p-chlorophenyl)sulfonyl]-3-propylurea; glipizide (1-cyclohexyl-3 [[p-[2(5-methylpyrazine carboxamido)ethyl] phenyl] sulfonyl] urea); tolazamide(benzenesulfonamide-N-[[(hexahydro-1H-azepin-1yl)amino]carbonyl]-4-methyl); glipizide; tolazamide; 2, 3-butanedione; 5-hydroxydecanoic acid; and quinine. In additional embodiments, non-sulfonyl urea compounds, such as 2, 3-butanedione and 5-hydroxydecanoic acid, quinine, and therapeutically equivalent salts and derivatives thereof, may be employed in the invention. In additional embodiments, active metabolites of the agents e.g. for glyburide 4-trans-hydroxy-(M1) and 3-cis-hydroxy-glibenclamide (M2) are employed. In specific cases, the inhibitor is a sulfonylurea compound or a benzamido derivative or meglitinide compound, or a mixture of two or more thereof.

The channel is expressed on cells, including, for example, neuronal cells, neuroglia cells, neural epithelial cells, endothelial cells, or a combination thereof. In specific embodiments, the inhibitor of the channel blocks the influx of $Na^+$ into the cells thereby preventing depolarization of the cells. Inhibition of the influx of $Na^+$ into the cells, thereby at least prevents or reduces cytotoxic edema and/or ionic edema, and prevents or reduces hemorrhagic conversion. Thus, this treatment reduces cell death, including, for example, necrotic cell death. In further embodiments, the invention reduces cell death of endothelial cells.

Another embodiment of the present invention comprises a method of reducing mortality of a subject suffering from ischemia/hypoxia comprising administering to the subject a combinatorial therapeutic composition effective at least in part to inhibit $NC_{Ca-ATP}$ channels in a cell.

Still further, another embodiment comprises a method of reducing edema in a peri-infarct tissue area of a subject comprising administering to the subject a combinatorial therapeutic composition effective to inhibit $NC_{Ca-ATP}$ channels.

Further embodiments comprises a method of treating a subject at risk of ischemia/hypoxia comprising administering to the subject a combinatorial therapeutic composition effective at least in part to inhibit a $NC_{Ca-ATP}$ channel in a cell.

In certain embodiments, the subject is undergoing treatment for a cardiac condition, thus the condition increases the subject's risk for ischemia, developing a stroke, or hemorrhage. The treatment, for example, may comprise the use of thrombolytic agents to treat myocardial infarctions. Still further, the subject may be at risk of ischemia or developing a stroke because the subject suffers from atrial fibrillation or a clotting disorder, for example. Other subjects that are at risk for ischemia or developing a stroke include subjects that are at risk of developing pulmonary emboli, subjects undergoing surgery (e.g., vascular surgery or neurological surgery), or subjects undergoing treatments that increase their risk for developing a stroke, for example, the treatment may comprise cerebral/endovascular treatment, angiography or stent placement. In other embodiments, the subject may be undergoing treatment for vascular disease that could place the spinal cord at risk for ischemia, such as surgery requiring aortic cross-clamping, surgery for abdominal aortic aneurysm, etc. In other embodiments, the patient may be undergoing surgery for a spinal or spinal cord condition, including discectomy, fusion, laminectomy, extradural or intradural surgery for tumor or mass etc., that would place the spinal cord at risk of injury. In some embodiments of the invention, the subject has a chronic condition, whereas in other embodiments of the invention, the subject does not have a chronic condition, such as a short-term condition.

Another embodiment of the present invention comprises a method of treating a subject at risk for developing edema comprising administering to the subject a combinatorial therapeutic composition effective at least in part to inhibit a $NC_{Ca-ATP}$ channel in at least an endothelial cell. The subject at risk may be suffering from an arterior-venous malformation, or a mass-occupying lesion (e.g., hematoma) or may be involved in activities that have an increased risk of trauma.

In further embodiments, the compound that inhibits the $NC_{Ca-ATP}$ channel can be administered in combination with the use of a mechanic thrombolytic device (e.g. the Concentric MERCI device) or a thrombolytic agent (e.g., tissue plasminogen activator (tPA), urokinase, prourokinase, streptokinase, anistreplase, reteplase, tenecteplase), an anticoagulant or antiplatelet (e.g., aspirin, warfarin or coumadin), statins, diuretics, vasodilators (e.g., nitroglycerin), mannitol, diazoxide or similar compounds that stimulate or promote ischemic precondition. In particular embodiments of the invention, the method further comprises delivery of an additional therapeutic agent to the individual, such as an immunosuppressant, an antiviral compound, an antibacterial compound, an antifungal compound, an antacid, or a combination or mixture thereof. In specific embodiments, the immunosuppressant is anti-thymocyte globulin, basiliximab, methylprednisone, tacrolimus, mycophenolate mofetil, prednisone, sirolimus, rapamycin, azathioprine, or a mixture thereof.

Yet further, another embodiment of the present invention comprises a pharmaceutical composition comprising a thrombolytic agent (e.g., tissue plasminogen activator (tPA), urokinase, prourokinase, streptokinase, anistreplase, reteplase, tenecteplase), an anticoagulant or antiplatelet (e.g., aspirin, warfarin or coumadin), statins, diuretics, vasodilators, mannitol, diazoxide or similar compounds that stimulate or promote ischemic precondition or a pharmaceutically acceptable salt thereof and a compound that inhibits a $NC_{Ca-ATP}$ channel or a pharmaceutically acceptable salt thereof. This pharmaceutical composition can be considered neuroprotective, in specific embodiments. For example, the pharmaceutical composition comprising a combination of the thrombolytic agent and a compound that inhibits a $NC_{Ca-ATP}$ channel is neuroprotective because it increases the therapeutic window for the administration of the thrombolytic agent by several hours; for example the therapeutic window for administration of thrombolytic agents may be increased by several hours (e.g. about 4 to about 8 hrs) by co-administering antagonist of the $NC_{Ca-ATP}$ channel.

In certain embodiments, the amount of the SUR1 antagonist administered to the subject is in the range of about 0.0001 µg/kg/day to about 20 mg/kg/day, about 0.01 µg/kg/day to about 100 µg/kg/day, or about 100 µg/kg/day to about 20 mg/kg/day. Still further, the SUR1 antagonist may be administered to the subject in the form of a treatment in which the treatment may comprise the amount of the SUR1 antagonist or the dose of the SUR1 antagonist that is administered per day (1, 2, 3, 4, etc.), week (1, 2, 3, 4, 5, etc.), month (1, 2, 3, 4, 5, etc.), etc. Treatments may be administered such that the amount of SUR1 antagonist administered to the subject is in the range of about 0.0001 µg/kg/treatment to about 20 mg/kg/treatment, about 0.01 µg/kg/treatment to about 100 µg/kg/treatment, or about 100 µg/kg/treatment to about 20 mg/kg/treatment.

In further embodiments, the compound that inhibits the $NC_{Ca-ATP}$ channel can be administered in combination with one or more of an antacid, an immunosuppressant, antibiotic, antiviral, antifungal, or combinations and/or mixtures thereof. Immunosuppressants include induction therapies, such as Thymoglobulin (anti-thymocyte globulin), Simulect (basiliximab) and/or Solumedrol (methylprednisolone), and/or maintenance therapies, such as Prograf (tacrolimus), CellCept (mycophenolate mofetil), Prednisone, Rapamune (Sirolimus, Rapamycin or RAPA) and/or Imuran (Azathioprine). Antibiotics include, for example, Bactrim (Sulfamethoxazole/Trimethoprim, SMZ/TMP), Mepron (Atovaquone), Co-trimoxazole, Nystatin, Clotrimazole, Pentamidine (Pentam 300), Amphotericin B (Fungazone) and/or Itraconazole (Sporanox). Antivirals include, for example, Valcyte (Valganciclovir), Valtrex (Valacyclovir), Acyclovir and Gancyclovir. Vaccinations include, for example, Influenza, Hepatitis A, Hepatitis B, Tetanus, Polio (inactivated), *S. pneumoniae, N. Meningitidis*, Rabies, Varicella, BCG, Smallpox and/or Anthrax. Anti-ulcer medications include, for example, Ranitidine, Famotidine (Pepcid) and/or Omeprazole. Blood pressure medication includes, for example, Calcium channel blockers, ACE inhibitors, Clonidine, Minoxidil and/or Diuretics (Furosemide Metolazone and Hydrochlorothiazide). Calcium supplements include, for example, Os-cal, calcium carbonate, Tums-EX, Biocal and/or Caltrate. Potassium supplements include, for example, K-Dur, Micro-K, Slow-K, K-lyte, K-lor, Klotrix, Kay Ciel, Kaon-Cl and/or Kaochlor. Cholesterol lowering drugs ("statins") include, for example, Pravachol, Lescol, Zocor, Lipitor and/or Baycol. Others drugs include, for example, platelet aggregatin inhibitors (Aspirin, Ascriptin, Bayer, Bufferin, Ecotrin, Empirin, Alka-Seltzer, etc.), Iron polysaccharide complex (Niferex®—150 Forte, Niferex®, Nu-Iron), magnesium supplements, Vitamin D, and/or laxatives (Docusate (aka colace), Metamucil, Dulcolax, and/or Pericolace).

The invention also relates to assays designed to screen for compounds or compositions that modulate the $NC_{Ca-ATP}$ channel, particularly compounds or compositions that act as antagonists of the channel, and thereby prevents and/or treats an ischemic episode. To this end, cell-based assays or non-cell based assays can be used to detect compounds that interact with, e.g., bind to, the outside (i.e., extracellular domain) of the $NC_{Ca-ATP}$ channel and/or its associated SUR1 regulatory subunit and TRPM4 pore. The cell-based assays have the advantage in that they can be used to identify compounds that affect $NC_{Ca-ATP}$ channel biological activity (i.e., depolarization). The invention also provides a method of screening for and identifying antagonists of the $NC_{Ca-ATP}$ channel, by contacting neural cells, for example, or any cell that expresses the channel, with a test compound and determining whether the test compound inhibits the activity of the $NC_{Ca-ATP}$ channel. In one embodiment, methods for identifying compounds that are antagonists of the $NC_{Ca-ATP}$ are provided. In one embodiment, therapeutic compounds of the present invention, including $NC_{Ca-ATP}$ antagonists, are identified by the compound's ability to block the open channel or to prevent channel opening, such as by quantifying channel function using electrophysiological techniques to measure membrane current through the channel, for example. $NC_{Ca-ATP}$ antagonists include compounds that are $NC_{Ca-ATP}$ channel inhibitors, $NC_{Ca-ATP}$ channel blockers, SUR1 antagonists, SUR1 inhibitors, and/or compounds that reduce the magnitude of membrane current through the channel, for example. In this embodiment, channel function can be measured in a preparation of neural cells, for example, from a human or animal, and the test compound can be brought into contact with the cell preparation by washing it over the cell preparation in solution. The invention further provides a method of screening for sulfonylurea compounds that may act as antagonists of the $NC_{Ca-ATP}$ channel.

In one embodiment of the invention, there is a method of preventing or reducing ischemic damage in one or more organs or tissues outside the central nervous system following an ischemic episode in an individual, comprising delivering to the individual an inhibitor of an $NC_{Ca-ATP}$ channel. The inhibitor may be further defined as a sulfonylurea compound, in certain aspects.

In certain aspects, delivering of the inhibitor is further defined as delivering the inhibitor directly to the organ or tissue. Delivering may be further defined as delivering the inhibitor to the individual prior to extraction of the organ or tissue, during extraction of the organ or tissue, or both, in particular embodiments. In other aspects, the delivering is further defined as delivering the inhibitor to the organ or tissue prior to extraction of the respective organ or tissue from the individual, delivering the inhibitor to the organ or tissue during extraction of the respective organ or tissue from the individual, delivering the inhibitor to the organ or tissue subsequent to extraction of the respective organ or tissue from the individual, or a combination thereof. Additional embodiments provide that delivering is further defined as delivering the inhibitor to a recipient of the organ or tissue prior to transplantation of the respective organ or tissue into the recipient, during transplantation of the respective organ or tissue into the recipient, and/or after transplantation of the respective organ or tissue into the recipient.

In specific embodiments of the invention, an ischemic episode is related to organ preservation for transplantation, angina pectoris, or kidney reperfusion injury. The organ is outside of the central nervous system and is the heart, kidney, lung, liver, eye, pancreas, or spleen, in particular aspects. In additional aspects, the tissue is spinal cord, corneal, skin, bone marrow, heart valve, or connective tissue.

In another embodiment of the invention, there is a method of determining the amount or severity of ischemic damage in one or more organs or tissues following an ischemic episode in an individual, comprising assaying one or more cells of the respective organ or tissue for a $NC_{Ca-ATP}$ channel. The assaying may be further defined as patch clamp analysis in at least one cell from the respective organ or tissue, in specific embodiments. In additional specific embodiments, when the channel is determined to be present in one or more cells of the organ or tissue, the respective organ or tissue is subjected to an inhibitor of the $NC_{Ca-ATP}$ channel. In further aspects, the respective organ or tissue is subjected to the inhibitor of the $NC_{Ca-ATP}$ channel prior to extraction from the individual, during extraction from the individual, and/or following extraction from the individual, or a combination thereof.

In particular aspects, there is a kit of the invention that comprises one or more of an inhibitor of the $NC_{Ca-ATP}$ channel, an organ transplantation therapeutic compound, or an organ transplantation apparatus. In another embodiment, there is a kit comprising two or more of the following, each of which is housed in a suitable container: an inhibitor of $NC_{Ca-ATP}$ channel, wherein the channel is regulated by SUR1; an organ transplant therapeutic compound; and an organ transplant apparatus. The organ transplant therapeutic compound may be selected from the group consisting of an immunosuppressant, an antiviral compound, an antibacterial compound, an antifungal compound, an antacid, or a combination or mixture thereof, in particular embodiments. In specific aspects, the organ transplantation apparatus comprises one or more of a scalpel, a needle, a thread, a suture, or a staple.

Still further, another embodiment comprises a method of treating acute ischemia (including, for example, in the brain, spinal cord, heart, liver, lungs, kidneys, and GI tract) in a subject comprising administering to a subject an amount of a compound that inhibits a $NC_{Ca-ATP}$ channel or a pharmaceutically acceptable salt thereof either with or without an amount of a thrombolytic agent or a pharmaceutically acceptable salt thereof in combination, or in conjunction with a mechanical thrombolytic device such as the Concentric MERCI device. In certain embodiments, the thrombolytic agent is a tissue plasminogen activator (tPA), urokinase, prourokinase, streptokinase, anistreplase, reteplase, tenecteplase or any combination thereof. The SUR1 antagonist can be administered by any standard parenteral or alimentary route, for example the SUR1 antagonist may be administered as a bolus injection or as an infusion or a combination thereof.

In another embodiment of the invention, there is a kit, housed in a suitable container, that comprises an inhibitor of $NC_{Ca-ATP}$ channel and one or more of a cation channel blocker and/or an antagonist of VEGF, MMP, NOS, or thrombin, for example. The kit may also comprise suitable tools to administer compositions of the invention to an individual.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following exemplary descriptions taken in conjunction with the accompanying exemplary drawings.

FIGS. 1A-1D show that glibenclamide inhibits newly expressed $NC_{Ca-ATP}$ channel in neurons isolated from the core of an infarct 2 hr after middle cerebral artery occlusion. (FIG. 1A) phase contrast micrograph of isolated neurons; b-d, patch clamp recordings showing block of channel activity by intracellular ATP (FIG. 1B), requirement for intracellular $Ca^{2+}$ (B), slope conductance of 34 pS with $K^+$ as the charge carrier (FIG. 1C), channel inhibition by 50 nM glibenclamide at pH 7.4 that increases at pH 6.8 (FIG. 1D); recordings in b and d were obtained with $Cs^+$ as the charge carrier to block any $K^+$ channel; recordings in b obtained with $K^+$ as the charge carrier, showing half the slope conductance expected for $K_{ATP}$ channel. (from Simard et al., 2006)

FIGS. 4A-4C show Na azide-induced blebbing is followed by necrotic death of freshly isolated reactive astrocytes. Color photomicrographs showing fields of cells at low power, labeled using propidium iodide (PI, red) to identify necrotic death (FIG. 4A) and annexin V (green) to identify apoptotic death (FIG. 4B). Necrotic death induced by 1 mM Na azide (NaAz) was significant reduced by 1 µM glibenclamide (FIG. 4A, FIG. 4C). Apoptotic death was minimal after exposure to Na azide (FIG. 4B, FIG. 4C) (from Simard et al., 2006).

FIGS. 5A-5D provide spinal cord injury (SCI) results in up-regulation of SUR1. Immunofluorescence (composite) images of axial spinal cord sections from control (FIG. 5A) and 24-hr after severe crush injury to the thoracolumbar cord (FIGS. 5B-5D), labeled for SUR1 (FIG. 5A, FIG. 5B, FIG. 5D) or GFAP (FIG. 5C). At high magnification, individual SUR1-positive cells (FIG. 5D) are stellate-shaped and co-label for GFAP (not shown), consistent with reactive astrocytes; severe crush injury was applied from the dorsal midline and resulted in complete loss of function.

FIGS. 6A-6B demonstrate SCI results in up-regulation of SUR1. Immunofluorescence images of longitudinal spinal cord sections from control (FIG. 6A) and 24-hr after modest cervical hemi-cord contusion injury (FIG. 6B), both labeled for SUR1; impact from above with impact site (IS) marked; contusion injury obtained using the same weight drop method as described in this proposal.

FIGS. 7A-7F illustrate immunofluorescence images of high power views of tissues following cervical SCI (same rat as FIG. 6, right) showing prominent labeling of capillaries, labeled for SUR1 (FIG. 7A, FIG. 7D) and co-labeled for vimentin (FIG. 7B, FIG. 7E); super-imposed images are also shown in color (FIG. 7C, FIG. 7F).

FIG. 14C shows immunolabeling and Western blots (lanes 1,2) for SUR1 in human aortic endothelial cells (ENDO) cultured under normoxic (N) or hypoxic (H) conditions; Western blots for SUR1 of rat insulinoma RIN-m5F cells (INSUL; lanes 3,4) cultured under normoxic or hypoxic condition, with β-actin also shown.

DETAILED DESCRIPTION OF THE INVENTION

Figure 2C:
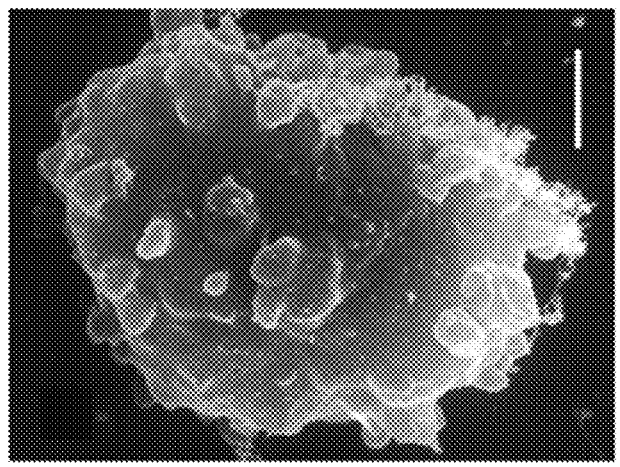
FIGS. 2A-2C demonstrate scanning electron micrographs showing numerous fine processes decorating the surface of freshly isolated reactive astrocyte under control conditions (FIG. 2A), and cell blebbing observed 5 min (FIG. 2B) and 25 min (FIG. 2C) after exposure to 1 mM Na azide; separate labeling showed that cells were GFAP-positive astrocytes. (from Chen and Simard, 2001)

The present application incorporates by reference herein in their entirety U.S. patent application Ser. No. 10/391,561, filed on Mar. 20, 2003; U.S. patent application Ser. No. 11/099,332, filed on Apr. 5, 2005; U.S. application Ser. No. 11/229,236, filed Sep. 16, 2005; U.S. patent application Ser. No. 11/359,946, filed on Feb. 22, 2006; U.S. Provisional Patent Application Ser. No. 60/889,065, filed on Feb. 9, 2007; and U.S. Provisional Patent Application Ser. No. 60/950,170, filed on Jul. 17, 2007.

Some of the preferred embodiments of the present invention will be described in detail with reference to the attached drawings. This invention may be embodied in many different forms and should not be construed as being limited to the embodiments set forth herein.

I. Definitions of Embodiments of the Invention

The use of the word "a" or "an" when used in conjunction with the term "comprising" in the claims and/or the specification may mean "one," but it is also consistent with the meaning of "one or more," "at least one," and "one or more than one." Some embodiments of the invention may consist of or consist essentially of one or more elements, method steps, and/or methods of the invention. It is contemplated that any method or composition described herein can be implemented with respect to any other method or composition described herein.

The use of the term "or" in the claims is used to mean "and/or" unless explicitly indicated to refer to alternatives only or the alternative are mutually exclusive, although the disclosure supports a definition that refers to only alternatives and "and/or."

As used herein, "about" refers to a numeric value, including, for example, whole numbers, fractions, and percentages, whether or not explicitly indicated. The term "about" generally refers to a range of numerical values (e.g., +/−10-20%, more preferably 5-10%, of the recited value) that one would consider equivalent to the recited value (e.g., having the same function or result). In some instances, the term "about" may include numerical values that are rounded to the nearest significant figure. As used herein "infarct" refers to an area of cell death in a cell, tissue, or organ resulting from an insufficiency of oxygen to said cell, tissue, or organ by, for example, inadequate blood supply.

As used herein, the term "acute" refers to the onset of a health effect, usually the effect is a rapid onset that is considered brief, not prolonged.

As used herein, the term "acute cerebral ischemia" refers to a cerebral ischemic event that has a rapid onset and is not prolonged. The terms "acute cerebral ischemia" and "stroke" can be used interchangeably.

As used herein, the term "$NC_{Ca-ATP}$ channel" refers to a non-selective cation channel complex that is activated by intracellular calcium and blocked by intracellular ATP, and has a single-channel conductance to potassium ion ($K^+$) of between about 20 and about 50 pS at physiological potassium concentrations. This channel complex includes a SUR1 receptor and is sensitive to SUR1 agonists and antagonists. In certain embodiments, the channel complex includes a pore that has similar properties to the TRPM4 channels, including blockade by TRPM4 blockers (such as, e.g., flufenamic acid, mefanimic acid, and niflumic acid), and therefore the pore of the $NC_{Ca-ATP}$ channel complex is TRPM4 channel. This channel complex is referred to herein as a "channel" and is described in greater detail elsewhere in the application.

As used herein, the term "TRPM4 channel" refers to a pore that passed ions that is a member of the transient receptor potential channel family (hence the acronym "TRP") and is the pore forming portion of the SUR1-sensitive $NC_{Ca-ATP}$ channel.

As used herein, the term "antagonist" refers to a biological or chemical agent that acts within the body to reduce the physiological activity of another chemical or biological substance. In the present invention, the antagonist blocks, inhibits, reduces and/or decreases the activity of a $NC_{Ca-ATP}$ channel of a neural cell, such as a neuronal cell, a neuroglia cell or a neural endothelial cell (e.g., capillary endothelial cells) or of endothelium and cells found outside of the CNS, for example in the aorta, liver, kidney, gastrointestinal tract, peripheral nerves, and heart. In the present invention, the antagonist combines, binds, associates with a $NC_{Ca-ATP}$ channel of a neural cell, such as a neuronal cell, a neuroglia cell or a neural endothelial cell (e.g., capillary endothelial cells) or of endothelium and cells found outside of the CNS, for example in the aorta, liver, kidney, gastrointestinal tract, peripheral nerves, and heart, such that the $NC_{Ca-ATP}$ channel is closed (deactivated), meaning reduced biological activity with respect to the biological activity in the diseased state. In certain embodiments, the antagonist combines, binds and/or associates with a regulatory subunit of the $NC_{Ca-ATP}$ channel, particularly a SUR1. Alternatively, the antagonist combines, binds, and/or associates with a pore-forming subunit of the $NC_{Ca-ATP}$ channel, such that the $NC_{Ca-ATP}$ channel is closed (deactivated). The terms antagonist or inhibitor can be used interchangeably.

As used herein, the terms "brain abscess" or "cerebral abscess" refer to a circumscribed collection of purulent exudate that is typically associated with swelling.

As used herein, the terms "blood brain barrier" or "BBB" refer the barrier between brain blood vessels and brain tissues whose effect is to restrict what may pass from the blood into the brain.

As used herein, the term "cerebral ischemia" refers to a lack of adequate blood flow to an area, for example a lack of adequate blood flow to the brain or spinal cord, which may be the result of a blood clot, blood vessel constriction, a hemorrhage or tissue compression from an expanding mass.

As used herein, the term "depolarization" refers to an increase in the permeability of the cell membrane to sodium ions wherein the electrical potential difference across the cell membrane is reduced or eliminated.

As used herein, the terms "effective amount" or "therapeutically effective amount" are interchangeable and refer to an amount that results in an improvement or remediation of at least one symptom of the disease or condition. Those of skill in the art understand that the effective amount may improve the patient's or subject's condition, but may not be a complete cure of the disease and/or condition.

As used herein, the term "endothelium" refers to a layer of cells that line the inside surfaces of body cavities, blood vessels, and lymph vessels or that form capillaries.

As used herein, the term "endothelial cell" refers to a cell of the endothelium or a cell that lines the surfaces of body cavities, for example, blood or lymph vessels or capillaries. In certain embodiments, the term endothelial cell refers to a neural endothelial cell or an endothelial cell that is part of the nervous system, for example the central nervous system or the brain or spinal cord.

As used herein, the term "gliotic capsule" refers to a physical barrier surrounding, in whole or in part, a foreign body, including a metastatic tumor, a cerebral abscess or other mass not normally found in brain except under pathological conditions. In certain embodiments, the gliotic capsule comprises an inner zone comprising neuronal cells, neuroglial cells (e.g., astrocytes) and/or endothelial cells expressing a $NC_{Ca-ATP}$ channel.

As used herein, the term "ionic edema" in brain or nervous tissue refers to edema arising in tissue in which the blood-brain barrier remains substantially intact, and is associated with the movement of electrolytes (e.g. $Na^+$, $Cl^-$) plus water into brain parenchyma.

As used herein, the term "inhibit" refers to the ability of the compound to block, partially block, interfere, decrease, reduce or deactivate a channel such as the $NC_{Ca-ATP}$ channel. Thus, one of skill in the art understands that the term inhibit encompasses a complete and/or partial loss of activity of a channel, such as the $NC_{Ca-ATP}$ channel. Channel activity may be inhibited by channel block (occlusion or closure of the pore region, preventing ionic current flow through the channel), by changes in an opening rate or in the mean open time, changes in a closing rate or in the mean closed time, or by other means. For example, a complete and/or partial loss of activity of the $NC_{Ca\text{-}ATP}$ channel as may be indicated by a reduction in cell depolarization, reduction in sodium ion influx or any other monovalent ion influx, reduction in an influx of water, reduction in extravasation of blood, reduction in cell death, as well as an improvement in cellular survival following an ischemic challenge.

The term "morbidity" as used herein is the state of being diseased. Yet further, morbidity can also refer to the disease rate or the ratio of sick subjects or cases of disease in to a given population.

The term "mortality" as used herein is the state of being mortal or causing death. Yet further, mortality can also refer to the death rate or the ratio of number of deaths to a given population.

As used herein, the term "neuron" refers to a nerve cell, also termed a neuronal cell.

As used herein, the term "neuronal cell" refers to a cell that is a morphologic and functional unit of the nervous system. The cell comprises a nerve cell body, the dendrites, and the axon. The terms neuron, nerve cell, neuronal, neurone, and neurocyte can be used interchangeably. Neuronal cell types can include, but are not limited to a typical nerve cell body showing internal structure, a horizontal cell (of Cajal) from cerebral cortex; Martinottic cell, biopolar cell, unipolar cell, Pukinje cell, and a pyramidal cell of motor area of cerebral cortex.

As used herein, the term "neural" refers to anything associated with the nervous system. As used herein, the term "neural cells" includes neurons and glia, including astrocytes, oligodrocytes, ependymal cells, and capillary endothelial cells. As used herein, the term "isolated neural cells" means neural cells isolated from brain.

As used herein, the terms "neuroglia" or "neuroglial cell" refers to a cell that is a non-neuronal cellular element of the nervous system. The terms neuroglia, neurogliacyte, and neuroglial cell can be used interchangeably. Neuroglial cells can include, but are not limited to ependymal cells, astrocytes, oligodendrocytes, or microglia.

As used herein, the term "non-CNS" refers to cells, tissues, or organs other than the brain or spinal cord. Non-CNS diseases and/or conditions exclude stroke, traumatic brain injury, and spinal cord injury.

The term "preventing" as used herein refers to minimizing, reducing or suppressing the risk of developing a disease state or parameters relating to the disease state or progression or other abnormal or deleterious conditions.

The term "protection" or "protect" as used herein refers to both protection and preservation of a cell, tissue, or organ under any circumstance. Protection encompasses, for example, protection in vivo, ex vivo, and in vitro.

The term "reactive astrocytes" means astrocytes found in brain at the site of a lesion or ischemia. The term "native reactive astrocytes" or "NRAs" means reactive astrocytes that are freshly isolated from brain. The term "freshly isolated" as used herein refers to NRAs that have been purified from brain, particularly NRAs that were purified from about 0 to about 72 hours previously. When NRAs are referred to as being "purified from brain" the word "purified" means that the NRAs are isolated from other brain tissue and/or implanted gelatin or sponge and does not refer to a process that simply harvests a population of cells from brain without further isolation of the cells. As described herein, the $NC_{Ca\text{-}ATP}$ channel found in reactive astrocytes is present only in freshly isolated cells; the $NC_{Ca\text{-}ATP}$ channel is lost shortly after culturing the cells under typical normoxic conditions. NRAs provide an in vitro model that is more similar to reactive astrocytes as they exist in vivo in the brain, than astrocytes grown in culture. The terms "native" and "freshly isolated" are used synonymously.

As used herein, the term "reduces" refers to a decrease in cell death, inflammatory response, hemorrhagic conversion, extravasation of blood, etc. as compared to no treatment with the compound of the present invention. Thus, one of skill in the art is able to determine the scope of the reduction of any of the symptoms and/or conditions associated with a spinal cord injury in which the subject has received the treatment of the present invention compared to no treatment and/or what would otherwise have occurred without intervention.

As used herein, the term "stroke" refers to any acute, clinical event related to the impairment of cerebral circulation. The terms "acute cerebral ischemia" and "stroke" can be used interchangeably.

The terms "treating" and "treatment" as used herein refer to administering to a subject a therapeutically effective amount of a composition so that the subject has an improvement in the disease or condition. The improvement is any observable or measurable improvement. Thus, one of skill in the art realizes that a treatment may improve the patient's condition, but may not be a complete cure of the disease. Treating may also comprise treating subjects at risk of developing a disease and/or condition.

As used herein, the term "vasogenic edema" in brain or nervous tissue refers to edema arising in tissue in which the blood-brain barrier is not substantially intact, and in which macromolecules plus water enter into brain parenchyma in addition to any movement of electrolytes.

II. General Embodiments of the Invention

The present invention relates to a novel ion channel whose function underlies the swelling of mammalian cells, for example, such as in response to ATP depletion. Treatment methods are provided that relate to diseases, trauma, and conditions that lead to the expression of such channels, including the use of inhibitors of the channel function to prevent this cell swelling response, which characterizes damage in ischemia/hypoxia and traumatic injury.

The $NC_{Ca\text{-}ATP}$ channel of the present invention is distinguished by certain functional characteristics, the combination of which distinguishes it from known ion channels. The characteristics that distinguish the $NC_{Ca\text{-}ATP}$ channel of the present invention include, but are not necessarily limited to, the following: 1) it is a non-selective cation channel that readily allows passage of Na, K and other monovalent cations; 2) it is activated by an increase in intracellular calcium, and/or by a decrease in intracellular ATP; 3) it is regulated by sulfonylurea receptor type 1 (SUR1), which heretofore had been considered to be associated exclusively with $K_{ATP}$ channels such as those found in pancreatic β cells, for example.

More specifically, the $NC_{Ca\text{-}ATP}$ channel of the present invention has a single-channel conductance to potassium ion ($K^+$) between 20 and 50 pS. The $NC_{Ca\text{-}ATP}$ channel is also stimulated by $Ca^{2+}$ on the cytoplasmic side of the cell membrane in a physiological concentration range, where said concentration range is from $10^{-8}$ to $10^{-5}$ M. The $NC_{Ca\text{-}ATP}$ channel is also inhibited by cytoplasmic ATP in a physiological concentration range, where said concentration range is from about $10^{-1}$ to about 5 mM. The $NC_{Ca\text{-}ATP}$ channel is also permeable to the following cations; $K^+$, $Cs^+$, Li$^+$, Na$^+$; to the extent that the permeability ratio between any two of said cations is greater than 0.5 and less than 2.

In general embodiments of the invention, there are methods and compositions for treating and/or preventing ischemic episode in an organ and/or tissue outside the central nervous system. In particular embodiments, an individual with an ischemic episode in an organ and/or tissue or at risk for having an ischemic episode in an organ and/or tissue is administered one or more inhibitors of a SUR1-regulated NC$_{Ca-ATP}$ channel. Exemplary inhibitors include sulfonylurea compounds, although others are also suitable.

In certain embodiments, the present invention concerns treatment and/or prevention of secondary or delayed injury associated with ischemia. Secondary injury involves a zone of potentially viable tissue, called the "penumbra", composed of "at-risk" tissue surrounding the primary injury site. Unlike primarily injured tissues that suffer injury from the very onset, for example, during ischemia or shortly following reperfusion, penumbral tissues are salvagable after the injury. Viability of cells in the penumbra is precarious, however, as these tissues can easily succumb and die.

It is generally accepted that penumbral tissues are at risk from formation of edema and ischemia. What is not generally recognized is that penumbral tissues are also at risk from "hemorrhagic conversion", a phenomenon wherein capillaries, especially those in capillary-rich gray matter, gradually loose their structural integrity, resulting in extravasation of blood. In the SCI literature, this may be referred to as "hemorrhagic necrosis". Whereas historically edema has been targeted for treatment with steroids, hemorrhagic conversion has not, simply because hemorrhage has not been viewed as being preventable. Blood is extremely toxic to neural tissues, however, as it incites free radicals and inflammatory responses that are especially damaging to myelin of white matter tracks, thereby worsening the overall neurological injury. Thus, if secondary injury is to be reduced, it is mandatory that hemorrhagic conversion be minimized.

The inventor identified a novel ion channel, the NC$_{Ca-ATP}$ channel, in neurons, astrocytes, and capillary endothelial cells. This channel is not constitutively expressed in any cell, but is expressed only after injury to the CNS or, in specific embodiments, is expressed in cells of tissue or organs after an ischemic episode. Originally, the work indicated that an ischemic/hypoxic insult was required for de novo expression, but more recently, evidence was obtained that indicated that this channel is also newly expressed following contusion injury to both brain and spinal cord.

The NC$_{Ca-ATP}$ channel conveys monovalent but not divalent cations, it requires intracellular Ca$^{2+}$, and channel opening is triggered by depletion of intracellular ATP. When opened, the channel rapidly depolarizes the cell due to influx of Na$^+$, drawing in Cl$^-$ and water, leading to cytotoxic (cellular) edema and eventually to oncotic (necrotic) cell death. Of particular importance, this channel is regulated by sulfonylurea receptor 1 (SUR1), just like many K$_{ATP}$ channels found throughout the body. Unlike K$_{ATP}$ channels, whose opening leads to hyperpolarization, opening of NC$_{Ca-ATP}$ channels leads to cell depolarization. Opening of NC$_{Ca-ATP}$ channels is prevented by the sulfonylurea, glibenclamide, which thus protects cells that express the channel from cytotoxic edema and cell death typically triggered by ATP depletion. In rodent models of stroke, systemic administration of low-dose glibenclamide is highly neuroprotective, resulting in large reductions in cerebral edema, stroke volume and mortality (Simard et al., 2006).

Studies using a cervical spinal cord contusion model were undertaken, because this is the typical injury seen clinically in the vast majority of patients with SCI. The inventor made some unexpected discoveries: (i) hemorrhage in the area of the contusion invariably increased after 24 hr; (ii) the SUR1 regulatory subunit of the NC$_{Ca-ATP}$ channel was up-regulated in neurons and capillaries following SCI; (iii) the delayed increase in hemorrhage could be significantly reduced by administering low-dose glibenclamide, which blocks the NC$_{Ca-ATP}$ channel; (iv) glibenclamide-treatment immediately following cervical spinal cord contusion was associated with significant neurological functional improvement. It is these unexpected discoveries that led the inventor to an embodiment of the present invention being that penumbral tissues are subject to delayed hemorrhagic conversion. In specific aspects of the invention, hemorrhagic conversion in penumbral tissues can be significantly ameliorated by glibenclamide, which completely transforms current treatment of SCI.

In specific embodiments, the present invention concerns treatment to reduce secondary injury from hemorrhagic conversion in SCI. In specific aspects of the invention, the time-course for up-regulation of the glibenclamide-sensitive, SUR1-regulated NC$_{Ca-ATP}$ channel following cervical SCI is determined, because knowledge of the time course assists in determination of the optimal treatment window. In additional embodiments, the time-course for evolution of secondary injury (edema and hemorrhagic conversion) and progression of lesion size is determined, again because knowledge of the time course assists in determination of an optimal treatment window. In particular embodiments, the optimal time-window and dose for treatment with glibenclamide are determined, which is based in part on information from the aforementioned studies. In additional embodiments, the therapeutic efficacy of an optimal dose of glibenclamide in neurological/behavioral studies is determined. Because glibenclamide is a safe drug that has been used for over two decades to treat type 2 diabetes in humans, the present invention provides an eminently useful treatment of SCI in humans that is critical to reducing secondary injury.

In specific embodiments related at least to ischemia of an organ, early treatment with the proper dose of the sulfonylurea receptor antagonist, glibenclamide, will do one or more of the following: (i) minimize secondary injury (formation of edema and hemorrhagic conversion); (ii) minimize lesion size, limiting it to the original site of direct injury; (iii) optimize functional neurological recovery.

In particular aspects, the time-course and cellular location for up-regulation of the glibenclamide-sensitive, SUR1-regulated NC$_{Ca-ATP}$ channel following organ ischemia is determined or provided. In another aspect, the time-course for evolution of secondary injury (edema and hemorrhagic conversion) and progression of lesion size is determined. In a further aspect, the optimal time-window and dose for treatment with glibenclamide is determined. In another aspect, the therapeutic efficacy of glibenclamide in functional recovery studies is further characterized.

The present invention concerns protection of one or more organs or tissues outside the central nervous system following an ischemic episode. Specific organ preservation uses include, for example, organ preservation for transplantation, including but not limited to liver, kidney, bladder, intestines, pancreas, lung and heart and other organs, angina pectoris, kidney reperfusion injury, and so forth. Tissue preservation uses include, for example, corneas, heart valves, skin, blood, bone marrow, connective tissue, and so forth. In particular aspects of the invention, an organ or tissue is subjected to a composition following an ischemic episode or prior to an ischemic episode. An individual may be delivered an inhibitor of the $NC_{Ca\text{-}ATP}$ channel, such as a sulfonylurea compound, including glibenclamide, for example. Such a delivery will prevent organ or tissue damage following ischemia, will prevent further organ or tissue damage following ischemia, or will prevent organ damage upon onset of ischemia.

Organs may be subjected to inhibitors of $NC_{Ca\text{-}ATP}$ for any therapeutic purpose for the organ, but in particular embodiments the organ is to be utilized for organ transplant. Therefore, delivery of an inhibitor of the $NC_{Ca\text{-}ATP}$ channel may occur prior to removal of the organ from the donor, upon removal of the organ from the donor, after removal of the organ from the donor, or a combination thereof. If delivery of an inhibitor of the $NC_{Ca\text{-}ATP}$ channel occurs upon or after removal of the organ, the inhibitor may be applied to part or all of the organ, such as to the part of the organ with detectable damage from ischemia or part of the organ susceptible to damage from the organ. Following extraction from the donor, the organ may be subjected to an inhibitor of the $NC_{Ca\text{-}ATP}$ channel in any suitable manner, for example by applying the inhibitor topically or by bathing part or all of the organ in a solution of the inhibitor of the $NC_{Ca\text{-}ATP}$ channel either alone or in conjunction with an existing organ preservation solution such as for example Celsior, UW, or HTK.

In other aspects of the invention, an organ is assessed for damage and subsequent determination of suitability for transplantation. In specific embodiments, the organ is assessed for suitable transplantation by determination of the presence of the $NC_{Ca\text{-}ATP}$ channel in one or more cells from the organ. If the organ is determined to have the $NC_{Ca\text{-}ATP}$ channel, the organ may not be used or the organ may still be used, such as following treatment of the organ with inhibitor of the $NC_{Ca\text{-}ATP}$ channel. The channel may be assayed in one or more of the cells by any suitable method, although in particular embodiments the cell is assayed by patch clamp technique, by standard molecular biology methods, or both, for example.

III. Ischemic Episode

In the context of the present invention, the term "ischemic episode" is referred to herein as a restriction in blood supply and/or decreased availability of oxygen to and/or in an organ or tissue of an individual, wherein the restriction may be a constriction and/or an obstruction, for example. The restriction may be due to factors in the blood vessels, in certain cases, and in particular aspects the ischemic episode results in damage or dysfunction of tissue of the organ or tissue and, in some cases, of the function of the organ or tissue itself.

In particular aspects of the invention, the ischemic episode concerns an absolute shortage of blood supply to an organ. In other aspects, the ischemic episode concerns inequity between blood supply (oxygen delivery) and blood demand for sufficient oxygenation of tissue. In certain aspects, an ischemic episode relates to inadequate flow of blood to a part of the body, such as an organ, caused by constriction or blockage of the blood vessels supplying it. For example, angina pectoris (chest pain from insufficient oxygen in the heart) is produced by ischemia of heart muscle. Ischemia may be a characteristic of a variety of maladies, including, for example, heart disease, transient ischemic attacks, cerebrovascular accidents, ruptured arteriovenous malformations, and peripheral artery occlusive disease.

In certain aspects of the invention, necrosis develops as a result of the ischemic episode, which may develop within minutes or hours of the episode, in specific embodiments.

Exemplary organs sensitive to inadequate blood supply include the brain, heart, kidney, lung, liver, eye, intestines, bladder, pancreas, or spleen. Ischemia in brain tissue, for example due to a heart attack, results in an ischemic cascade wherein reactive oxygen species, proteolytic enzymes, and/or other harmful chemicals damage and may ultimately destroy cardiac tissue. Exemplary tissues include, for example, corneal, skin, bone marrow, heart valve, or connective tissue.

It is known that restoration of blood flow following an ischemic episode can be equally if not more damaging than the ischemic episode, because reintroduction of oxygen results in an increased production of damaging free radicals that results in reperfusion injury. Necrosis can be greatly accelerated upon reperfusion, and therefore the compounds of the present invention may be delivered to an individual prior to, upon initiating restoration of blood flow, or during the restoration of blood flow to the body part.

In particular embodiments of the invention, an ischemic episode occurs prior to and/or during shock or organ transplantation or is at risk for developing with shock or organ transplantation, and in these exemplary cases the ischemic episode is treated with a compound of the invention.

IV. $NC_{Ca\text{-}ATP}$ Channel

A unique non-selective monovalent cationic ATP-sensitive channel ($NC_{Ca\text{-}ATP}$ channel) was identified first in native reactive astrocytes (NRAs) and later in neurons and capillary endothelial cells after stroke or traumatic brain or spinal cord injury (See at least International application WO 03/079987 to Simard et al., and Chen and Simard, 2001, each incorporated by reference herein in its entirety). As with the $K_{ATP}$ channel in pancreatic (3 cells, the $NC_{CaATP}$ channel is considered to be a heteromultimer structure comprised of sulfonylurea receptor type 1 (SUR1) regulatory subunits and pore-forming subunits (Chen et al., 2003). The pore-forming subunits have been characterized biophysically and have been identified as TRPM4.

The invention is based, in part, on the discovery of a specific channel, the $NC_{Ca\text{-}ATP}$ channel, defined as a channel on astrocytes in U.S. Application Publication No. 20030215889, which is incorporated herein by reference in its entirety. More specifically, the present invention has further defined that this channel is not only expressed on astrocytes, it is expressed on neural cells, neuroglial cells, and/or endothelial cells after brain and spinal cord trauma, for example, an hypoxic event, an ischemic event, or other secondary neuronal injuries relating to these events. Moreover, it is also expressed in cells outside of the CNS, including endothelial cells and cells of other organs.

The $NC_{Ca\text{-}ATP}$ channel is activated by calcium ions ($Ca^{2+}$) and is sensitive to ATP. Thus, this channel is a non-selective cation channel activated by intracellular $Ca^{2+}$ and blocked by intracellular ATP. When opened by depletion of intracellular ATP, this channel is responsible for complete depolarization due to massive $Na^+$ influx, which creates an electrical gradient for $Cl^-$ and an osmotic gradient for $H_2O$, resulting in cytotoxic edema and cell death. When the channel is blocked or inhibited, massive $Na^+$ does not occur, thereby preventing cytotoxic edema.

Certain functional characteristics distinguish the $NC_{Ca\text{-}ATP}$ channel from other known ion channels. These characteristics can include, but are not limited to, at least some of the following: 1) it is a non-selective cation channel that readily allows passage of $Na^+$, $K^+$ and other monovalent cations; 2) it is activated by an increase in intracellular calcium, and/or by a decrease in intracellular ATP; 3) it is regulated by sulfonylurea receptor type 1 (SUR1), which heretofore had been considered to be associated exclusively with $K_{ATP}$ channels such as those found in pancreatic β cells.

More specifically, the $NC_{Ca\text{-}ATP}$ channel of the present invention has a single-channel conductance to potassium ion ($K^+$) between 20 and 50 pS. The $NC_{Ca\text{-}ATP}$ channel is also stimulated by $Ca^{2+}$ on the cytoplasmic side of the cell membrane in a physiological concentration range, where concentration range is from $10^{-8}$ to $10^{-5}$ M. The $NC_{Ca\text{-}ATP}$ channel is also inhibited by cytoplasmic ATP in a physiological concentration range, where the concentration range is from $10^{-1}$ to 5 mM. The $NC_{Ca\text{-}ATP}$ channel is also permeable to the following cations; $K^+$, $Cs^+$, $Li^+$, $Na^+$; to the extent that the permeability ratio between any two of the cations is greater than 0.5 and less than 2.

SUR imparts sensitivity to antidiabetic sulfonylureas such as glibenclamide and tolbutamide and is responsible for activation by a chemically diverse group of agents termed "$K^+$ channel openers" such as diazoxide, pinacidil and cromakalin (Aguilar-Bryan et al., 1995; Inagaki et al., 1996; Isomoto et al., 1996; Nichols et al., 1996; Shyng et al., 1997). In various tissues, molecularly distinct SURs are coupled to distinct pore-forming subunits to form different $K_{ATP}$ channels with distinguishable physiological and pharmacological characteristics. The $K_{ATP}$ channel in pancreatic β cells is formed from SUR1 linked with Kir6.2, whereas the cardiac and smooth muscle $K_{ATP}$ channels are formed from SUR2A and SUR2B linked with Kir6.2 and Kir6.1, respectively (Fujita et al., 2000). Despite being made up of distinctly different pore-forming subunits, the $NC_{Ca\text{-}ATP}$ channel is also sensitive to sulfonylurea compounds.

Also, unlike the $K_{ATP}$ channel, the $NC_{Ca\text{-}ATP}$ channel conducts sodium ions, potassium ions, cesium ions and other monovalent cations with near equal facility (Chen and Simard, 2001) suggesting further that the characterization, and consequently the affinity to certain compounds, of the $NC_{Ca\text{-}ATP}$ channel differs from the $K_{ATP}$ channel.

Other nonselective cation channels that are activated by intracellular $Ca^{2+}$ and inhibited by intracellular ATP have been identified by others but not in astrocytes, neurons, or endothelial cells, as disclosed herein. Further, the $NC_{Ca\text{-}ATP}$ channel expressed and found in astrocytes differs physiologically from the other channels with respect to calcium sensitivity and adenine nucleotide sensitivity (Chen et al., 2001).

V. Summary of $Nc_{Ca\text{-}Atp}$ Channel Characteristics

At least some of the characteristics of cells expressing and composition comprising the $NC_{Ca\text{-}ATP}$ channel of the present invention are summarized in Table 1 (taken from experiments with freshly isolated native reactive astrocytes (NRA]).

TABLE 1

| Properties of cells and membrane compositions containing the $NC_{Ca\text{-}ATP}$ Channel of the Present Invention | Reactive Astrocytes | Membrane Preparation derived from freshly isolated native reactive astrocytes |
|---|---|---|
| Monovalent cation permeable? | Yes: $Na^+$ $K^+$ $Li^+$ $Rb^+$ $Cs^+$ ($Na^+\approx K^+\approx Li^+\approx Rb^+$) | Yes: $Na^+$ $K^+$ $Li^+$ $Rb^+$ $Cs^+$ ($Na^+\approx K^+\approx Li^+\approx Rb^+$) |
| Anion permeable? | No | No |
| Divalent cation permeable? | No | No |
| Compounds blocking channel activity | SUR1 antagonists | SUR1 ANTAGONISTS |
| Channel opening Requires: | Intracell. ATP depletion Intracell. $Mg^{2+}$ | Intracell ATP depletion Intracell. $Mg^{2+}$ |
| Single Channel Conductance | ~35 pS | ~35 pS |
| Activation [$Ca^{2+}$] | <1.0 μM | <1.0 μM |
| [ATP]$_1$EC$_{50}$ (um) | 0.79 μM | 0.79 μM |
| ADP AMP | No channel effect | No channel effect |
| Pore radius (nm) | 0.41 | 0.41 |

VI. Exemplary Embodiments of the Present Invention

In some embodiments, the present invention is directed to therapeutic compositions and methods of using the same. In one embodiment, the therapeutic composition comprises at least an antagonist of at least one $NC_{Ca\text{-}ATP}$ channel of a cell, such as, for example, a neuronal cell, a neuroglial cell, an endothelial cell, or other cell type subject to ischemia/hypoxia or trauma.

It is a further object of the present invention to provide a method of preventing and/or reducing cell swelling in a subject, said method comprising administering to the subject a formulation containing an effective amount of a combinatorial therapeutic composition comprising a compound that blocks the $NC_{Ca\text{-}ATP}$ channel, and a pharmaceutically acceptable carrier.

It is an object of the present invention to provide a method of alleviating the negative effects of traumatic injury or ischemia stemming from cell swelling in a subject, comprising administering to the subject a formulation comprising an effective amount of a combinatorial therapeutic composition that at least in part blocks the $NC_{Ca\text{-}ATP}$ channel, and a pharmaceutically acceptable carrier. Such administration may be delivery directly, intravenously, subcutaneously, intramuscularly, intracutaneously, intragastrically and orally. Examples of such compounds include an inhibitor of the channel, such as, for example, an antagonist of a type 1 sulfonylurea receptor, such as sulfonylureas like glibenclamide and tolbutamide, as well as other insulin secretagogues such as repaglinide, nateglinide, meglitinide, Mitiglinide, iptakalim, endosulfines, LY397364, LY389382, gliclazide, glimepiride, MgADP, and combinations thereof.

It is yet another object of the present invention to provide a formulation for preventing or inhibiting cell swelling in a subject, using a formulation that includes a combinatorial therapeutic composition that at least in part blocks the $NC_{Ca\text{-}ATP}$ channel and a pharmaceutically acceptable carrier, wherein the quantity of said compound is less than the quantity of said compound in formulations for treating diabetes. It is a further object of the present invention to provide a formulation for preventing or inhibiting cell swelling in a subject, using a formulation that includes a compound that blocks the $NC_{Ca\text{-}ATP}$ channel and a pharmaceutically acceptable carrier, wherein the quantity of said compound is at least 2 times less than the quantity of said compound in formulations for treating diabetes. It is a further object of the present invention to provide a formulation for preventing or inhibiting cell swelling in a subject, using a formulation that includes a compound that blocks the $NC_{Ca\text{-}ATP}$ channel and a pharmaceutically acceptable carrier, wherein the quantity of said compound is at least 5 times less than the quantity of said compound in formulations for treating diabetes. It is yet another object of the present invention to provide a formulation for preventing or inhibiting cell swelling in a subject, using a formulation that includes a compound that blocks the $NC_{Ca\text{-}ATP}$ channel and a pharmaceutically acceptable carrier, wherein the quantity of said compound is at least 10 times less than the quantity of said compound in formulations for treating diabetes.

In addition to the sulfonylurea receptor 1 (SUR1) being expressed in R1 astrocytes as part of the $NC_{Ca\text{-}ATP}$ channel, the present invention further describes that the SUR1 regulatory subunit of this channel is up-regulated in neurons and capillary endothelial cells following ischemia, and blocking this receptor reduces infarct size, edema and mortality. Thus, antagonists of the $NC_{Ca\text{-}ATP}$ channel have an important role in preventing, alleviating, inhibiting and/or abrogating the formation of cytotoxic and ionic edema.

In other embodiments, the therapeutic compound of the present invention comprises at least an antagonist of a $NC_{Ca\text{-}ATP}$ channel of a cell, such as a neuronal cell, a neuroglial cell, an endothelial cell or a combination thereof. Antagonists are contemplated for use in treating adverse conditions associated with hypoxia and/or ischemia that result in increased cytotoxic edema. Such conditions include trauma, ischemia/hypoxia, namely secondary injury, and hemorrhagic infarction. Antagonists protect the cells expressing the $NC_{Ca\text{-}ATP}$ channel, which is desirable for clinical treatment in which gliotic capsule integrity is important and must be maintained to prevent the spread of infection, such as with a brain abscess. The protection via inhibition of the $NC_{Ca\text{-}ATP}$ channel is associated with a reduction in edema.

In one aspect, the $NC_{Ca\text{-}ATP}$ channel is blocked, inhibited, or otherwise is decreased in activity. In such examples, an antagonist of the $NC_{Ca\text{-}ATP}$ channel is administered and/or applied. The antagonist modulates the $NC_{Ca\text{-}ATP}$ channel such that flux through the channel is reduced, ceased, decreased and/or stopped. The antagonist may have a reversible or an irreversible activity with respect to the activity of the $NC_{Ca\text{-}ATP}$ channel of a cell, such as, a neuronal cell, neuroglial cell, endothelial cell or a combination thereof. The antagonist may prevent or lessen the depolarization of the cells thereby lessening cell swelling due to osmotic changes that can result from depolarization of the cells. Thus, inhibition of the $NC_{Ca\text{-}ATP}$ channel can reduce cytotoxic edema and death of endothelial cells.

Subjects that can be treated with the therapeutic composition of the present invention include, but are not limited to subjects suffering from or at risk of developing conditions associated hypoxia and/or ischemia that result in increased cytotoxic edema. Such conditions include, but are not limited to trauma (e.g., traumatic brain or spinal cord injury (TBI or SCI), concussion) ischemia/hypoxia, hemorrhagic infarction, stroke, atrial fibrillations, clotting disorders, pulmonary emboli, arterio-venous malformations, mass-occupying lesions (e.g., hematomas), shock, etc. Still further subjects at risk of developing such conditions can include subjects undergoing treatments that increase the risk of stroke, for example, surgery (vascular or neurological), treatment of myocardial infarction with thrombolytics, cerebral/endovascular treatments, stent placements, angiography, etc.

In other embodiments, the therapeutic compound of the present invention comprises at least an antagonist of a $NC_{Ca\text{-}ATP}$ channel of a cell, such as a neuronal cell, a neuroglial cell, an endothelial cell or a combination thereof. Antagonists are contemplated for use in treating adverse conditions associated with cytotoxic edema, in specific embodiments. Such conditions include trauma (e.g., traumatic brain or spinal cord injury (TBI or SCI, respectively)), ischemia/hypoxia, primary and secondary ischemia/hypoxia injury, stroke, arteriovenous malformations (AVM), mass-occupying lesion (e.g., hematoma), and hemorrhagic infarction. Antagonists protect the cells expressing the $NC_{Ca\text{-}ATP}$ channel, which is desirable for clinical treatment in which ionic or cytotoxic edema is formed, in which capillary integrity is lost following ischemia, and/or in which gliotic capsule integrity is important and must be maintained to prevent the spread of infection, such as with a brain abscess. Those of skill in the art realize that a brain abscess is a completely enclosed and results in cerebral swelling. The protection via inhibition of the $NC_{Ca\text{-}ATP}$ channel is associated with a reduction in ionic and cytotoxic edema. Thus, the compound that inhibits the $NC_{Ca\text{-}ATP}$ channel is cytoprotective.

In one aspect, the $NC_{Ca\text{-}ATP}$ channel is blocked, inhibited, or otherwise is decreased in activity. In such examples, an antagonist of the $NC_{Ca\text{-}ATP}$ channel is administered and/or applied. The antagonist modulates the $NC_{Ca\text{-}ATP}$ channel such that flux (ion and/or water) through the channel is reduced, ceased, decreased and/or stopped. The antagonist may have a reversible or an irreversible activity with respect to the activity of the $NC_{Ca\text{-}ATP}$ channel of the neuronal cell, neuroglial cell, a neural endothelial cell or a combination thereof. Thus, inhibition of the $NC_{Ca\text{-}ATP}$ channel can reduce cytotoxic edema and death of endothelial cells which are associated with formation of ionic edema and with hemorrhagic conversion.

Accordingly, the present invention is useful in the treatment or alleviation of acute ischemia. According to a specific embodiment of the present invention the administration of effective amounts of the active compound can block the channel, which if remained open leads to cell swelling and cell death. A variety of antagonists to SUR1 are suitable for blocking the channel. Examples of suitable SUR1 antagonists include, but are not limited to glibenclamide, tolbutamide, repaglinide, nateglinide, meglitinide, Mitiglinide, iptakalim, endosulfines, LY397364, LY389382, glyclazide, glimepiride, mitiglinide, iptakalim, endosulfines, estrogen, estrogen related-compounds including estradiol, estrone, estriol, genistein, non-steroidal estrogen (e.g., diethylstilbestrol), phytoestrogen (e.g., coumestrol), zearalenone, etc., and combinations thereof. In a preferred embodiment of the invention the SUR1 antagonists is selected from the group consisting of glibenclamide and tolbutamide. Another antagonist that can be used is MgADP. Still other therapeutic "strategies" for preventing cell swelling and cell death can be adopted including, but not limited to methods that maintain the cell in a polarized state and methods that prevent strong depolarization.

In further embodiments, inhibitors or antagonist of the $NC_{Ca\text{-}ATP}$ channel can be used to reduce or alleviate or abrogate hemorrhagic conversion. The pathological sequence that takes place in capillaries after ischemia can be divided into 3 stages, based on the principal constituents that move from the intravascular compartment into the parenchyma (Ayata 2002; Betz, 1996; Betz 1989). For example in the brain, the first stage is characterized by formation of "ionic" edema, during which the BBB remains intact, with movement of electrolytes ($Na^+$, $Cl^-$) plus water into brain parenchyma. The second stage is characterized by formation of "vasogenic" edema, due to breakdown of the BBB, during which macromolecules plus water enter into brain parenchyma. The third stage is characterized by hemorrhagic conversion, due to catastrophic failure of capillaries, during which all constituents of blood extravasate into brain parenchyma. In accordance with Starling's law, understanding these phases requires that 2 things be identified: (i) the driving force that "pushes" things into the parenchyma; and (ii) the permeability pore that allows passage of these things into the parenchyma.

Thus, the use of the antagonist or related-compounds thereof can reduce the mortality of a subject suffering from ischemia/hypoxia and/or rescue the penumbra area or prevent damage in the penumbra area which comprises areas of tissue that are at risk of becoming irreversibly damaged.

With the administration of an antagonist of the $NC_{Ca-ATP}$ channel, endothelial cell depolarization is abrogated, slowed, reduced or inhibited due to the opening of the $NC_{Ca-ATP}$ channel. Thus, abrogation of cell depolarization results in abrogation or inhibition of $Na^+$ influx, which prevents a change in osmotic gradient thereby preventing an influx of water into the endothelial cell and stopping cell swelling, blebbing and cytotoxic edema. Thus, preventing or inhibiting or attenuating endothelial cell depolarization can prevent or reduce hemorrhagic conversion.

Cells in which the antagonist of the $NC_{Ca-ATP}$ channel may be administered include any cell that expresses SUR1, including for example, any neuronal cell, neuroglial cell, endothelia cell, or other cell of an organ or tissue subject to ischemia/hypoxia, trauma, or transplantation.

Subjects that may be treated with the antagonist or related-compound thereof include those that are suffering from or at risk of developing trauma (e.g., traumatic brain or spinal cord injury (TBI or SCI)), ischemic brain or spinal cord injury, primary and secondary neuronal injury, stroke, arteriovenous malformations (AVM), brain abscess, mass-occupying lesion, hemorrhagic infarction, or any other condition associated with cerebral hypoxia or cerebral ischemia resulting in cerebral edema and/or increased intracranial pressure (for example, but not limited to brain mass, brain edema, hematoma, end stage cerebral edema, encephalopathies, etc.), shock, ischemic tissues or organs, and organ transplantation. Thus, the antagonist can be a therapeutic treatment in which the therapeutic treatment includes prophylaxis or a prophylactic treatment. The antagonist or related-compounds thereof are cytoprotective.

Other subjects that may be treated with the antagonist of the present invention include those subjects that are at risk or predisposed to developing a stroke or heart attack. Such subjects can include, but are not limited to subjects that suffer from arrhythmia of the atria or ventricle, atrial fibrillations, clotting disorders, and/or risk of pulmonary emboli.

In certain embodiments, a subject at risk for developing ischemia, a stroke or heart attack or shock may include subjects undergoing treatments, for example, but not limited to cerebral/endovascular treatments, surgery (e.g., craniotomy, cranial surgery, removal of brain tumors (e.g., hematoma), coronary artery bypass grafting (CABG), angiography, stent replacement, other vascular surgeries, and/or other CNS or neurological surgeries), and treatment of myocardial infarction (MI) with thrombolytics, as well as surgeries on aortic abdominal aneurysms and major vessels that provide blood supply to the spinal cord. In such cases, the subject may be treated with the antagonist or related-compound of the present invention prior to the actual treatment. Pretreatment can include administration of the antagonist and/or related-compound months (1, 2, 3, etc.), weeks (1, 2, 3, etc.), days (1, 2, 3, etc.), hours (1, 2, 3, 4, 5, 6, 7, 8, 9, 10, 11, 12), or minutes (15, 30, 60, 90, etc.) prior to the actual treatment or surgery. Treatment of the antagonist and/or related-compound can continue during the treatment and/or surgery and after the treatment and/or surgery until the risk of developing a stroke or heart attack in the subject is decreased, lessened or alleviated.

In further embodiments, the antagonist of the present invention can be given to a subject at risk of developing head/neck trauma, such as a subject involved in sports or other activities that have an increased risk of head/neck trauma.

An effective amount of an antagonist of the $NC_{Ca-ATP}$ channel that may be administered to a cell includes a dose of about 0.0001 nM to about 2000 µM. More specifically, doses of an agonist to be administered are from about 0.01 nM to about 2000 µM; about 0.01 µM to about 0.05 µM; about 0.05 µM to about 1.0 µM; about 1.0 µM to about 1.5 µM; about 1.5 µM to about 2.0 □µM; about 2.0 µM to about 3.0 µM; about 3.0 µM to about 4.0 µM; about 4.0 µM to about 5.0 µM; about 5.0 µM to about 10 µM; about 10 µM to about 50 µM; about 50 µM to about 100 µM; about 100 µM to about 200 □µM; about 200 µM to about 300 µM about 300 µM to about 500 µM; about 500 µM to about 1000 µM; about 1000 µM to about 1500 µM and about 1500 µM to about 2000 µM. Of course, all of these amounts are exemplary, and any amount in-between these points is also expected to be of use in the invention.

The antagonist or related-compound thereof can be administered parenterally or alimentary. Parenteral administrations include, but are not limited to intravenously, intradermally, intramuscularly, intraarterially, intrathecally, subcutaneous, or intraperitoneally U.S. Pat. Nos. 6,613,308, 5,466,468, 5,543,158; 5,641,515; and 5,399,363 (each specifically incorporated herein by reference in its entirety). Alimentary administrations include, but are not limited to orally, buccally, rectally, or sublingually.

The administration of the therapeutic compounds and/or the therapies of the present invention may include systemic, local and/or regional administrations, for example, topically (dermally, transdermally), via catheters, implantable pumps, etc. Alternatively, other routes of administration are also contemplated such as, for example, arterial perfusion, intra-cavitary, intraperitoneal, intrapleural, intraventricular and/or intrathecal. The skilled artisan is aware of determining the appropriate administration route using standard methods and procedures. Other routes of administration are discussed elsewhere in the specification and are incorporated herein by reference.

Treatment methods involve treating an individual with an effective amount of a composition containing an antagonist of $NC_{Ca-ATP}$ channel or related-compound thereof. An effective amount is described, generally, as that amount sufficient to detectably and repeatedly to ameliorate, reduce, minimize or limit the extent of a disease or its symptoms. More specifically, treatment with the an antagonist of $NC_{Ca-ATP}$ channel or related-compounds thereof inhibits cell depolarization, inhibits $Na^+$ influx, inhibits an osmotic gradient change, inhibits water influx into the cell, inhibits cytotoxic cell edema, decreases infarct size, inhibits hemorrhagic conversion, and decreases mortality of the subject.

The effective amount of an antagonist of $NC_{Ca-ATP}$ channel or related-compounds thereof to be used are those amounts effective to produce beneficial results, particularly with respect to stroke or heart attack treatment, in the recipient animal or patient. Such amounts may be initially determined by reviewing the published literature, by conducting in vitro tests or by conducting metabolic studies in healthy experimental animals. Before use in a clinical setting, it may be beneficial to conduct confirmatory studies in an animal model, preferably a widely accepted animal model of the particular disease to be treated. Preferred animal models for use in certain embodiments are rodent models, which are preferred because they are economical to use and, particularly, because the results gained are widely accepted as predictive of clinical value.

As is well known in the art, a specific dose level of active compounds such as an antagonist of the $NC_{Ca-ATP}$ channel or related-compounds thereof for any particular patient depends upon a variety of factors including the activity of the specific compound employed, the age, body weight, general health, sex, diet, time of administration, route of administration, rate of excretion, drug combination, and the severity of the particular disease undergoing therapy. The person responsible for administration will determine the appropriate dose for the individual subject. Moreover, for human administration, preparations should meet sterility, pyrogenicity, general safety and purity standards as required by FDA Office of Biologics standards.

One of skill in the art realizes that the effective amount of the antagonist or related-compound thereof can be the amount that is required to achieve the desired result: reduction in the risk of stroke or heart attack, reduction in intracranial pressure, reduction in cell death, reduction in infarct size, reduction in cell edema, reduction in spinal cord injury, etc. This amount also is an amount that maintains a reasonable level of blood glucose in the patient, for example, the amount of the antagonist maintains a blood glucose level of at least 60 mmol/l, more preferably, the blood glucose level is maintain in the range of about 60 mmol/l to about 150 mmol/l. Thus, the amounts prevent the subject from becoming hypoglycemic. If glucose levels are not normal, then one of skill in the art would administer either insulin or glucose, depending upon if the patient is hypoglycemic or hyperglycemic.

Administration of the therapeutic antagonist of $NC_{Ca-ATP}$ channel composition of the present invention to a patient or subject will follow general protocols for the administration of therapies used in stroke or heart attack treatment, such as thrombolytics, taking into account the toxicity, if any, of the antagonist of the $NC_{Ca-ATP}$ channel. It is expected that the treatment cycles would be repeated as necessary. It also is contemplated that various standard therapies, as well as surgical intervention, may be applied in combination with the described therapy.

Another aspect of the present invention for the treatment of ischemia, trauma, or other injury comprises administration of an effective amount of a SUR1 antagonist and administration of glucose. Glucose administration may be at the time of treatment with an antagonist of the $NC_{Ca-ATP}$ channel, such as a SUR1 antagonist, or may follow treatment with an antagonist of the $NC_{Ca-ATP}$ channel (e.g., at about 15 minutes after treatment with an antagonist of the $NC_{Ca-ATP}$ channel, or at about one half hour after treatment with an antagonist of the $NC_{Ca-ATP}$ channel, or at about one hour after treatment with an antagonist of the $NC_{Ca-ATP}$ channel, or at about two hours after treatment with an antagonist of the $NC_{Ca-ATP}$ channel, or at about three hours after treatment with an antagonist of the $NC_{Ca-ATP}$ channel). Glucose administration may be by intravenous, intraperitoneal, or other suitable route and means of delivery as determined by one of ordinary skill in the art. Additional glucose allows administration of higher doses of an antagonist of the $NC_{Ca-ATP}$ channel than might otherwise be possible, so that combined glucose with an antagonist of the $NC_{Ca-ATP}$ channel provides greater protection, and may allow treatment at later times, than with an antagonist of the $NC_{Ca-ATP}$ channel alone. Greater amounts of glucose are administered where larger doses of an antagonist of the $NC_{Ca-ATP}$ channel are administered.

Another aspect of the present invention comprises co-administration of an antagonist of the $NC_{Ca-ATP}$ channel with a thrombolytic agent. Co-administration of these two compound increases the therapeutic window of the thrombolytic agent by reducing hemorrhagic conversion. The therapeutic window for thrombolytic agents may be increased by several (4-8) hours by co-administering antagonist of the $NC_{Ca-ATP}$ channel. In addition to a thrombolytic agent, other agents can be used in combination with the antagonist of the present invention, for example, but not limited to antiplatelets, anticoagulants, vasodilators, statins, diuretics, etc.

Yet further, the compositions of the present invention can be used to produce cytoprotective kits that are used to treat subjects at risk or suffering from conditions that are associated with cytotoxic edema, including, for example, ischemia/hypoxia and organ or tissue transplantation.

VII. Non-Selective Cation Channels, Transient Receptor Potential Channels, and Ischemic Stroke A number of different mechanisms have been implicated in cell death associated with, for example, ischemia/hypoxia and trauma, including excitotoxicity, oxidative stress, apoptosis, and oncotic (necrotic) cell death. Each of these mechanisms is thought to propagate through largely distinct, mutually exclusive signal transduction pathways (Won et al., 2002). However, in some measure, each of these mechanisms requires cation influx into cells. Unchecked influx of $Na^+$ gives rise to oncotic cell swelling (cytotoxic edema), which predisposes to oncotic cell death. Unchecked influx of $Ca^{2+}$ can trigger apoptotic as well as necrotic death. Because cation channels are responsible for most cation influx, it is evident that cation channels are key to life-death processes in cells during ischemia/hypoxia and trauma.

A variety of cation channels have been implicated in cell death induced by ischemia/hypoxia. Among them are channels that are highly selective for permeant cations, such as voltage-dependent $Na^+$ and $Ca^{2+}$ channels, as well as channels that are not selective for any given cation—non-selective cation (NC) channels. In ischemic stroke, much attention has been directed to dihydropyridine-sensitive L-type voltage-dependent $Ca^{2+}$ channels (CaV1.2), but block of this channel in patients with acute ischemic stroke has shown little benefit (Horn and Limburg, 2000). Arguably, the best studied channels in ischemic stroke belong to the group of receptor operated cation channels opened by glutamate, including N-methyl-D-aspartate (NMDA) and γ-amino-3-hydroxy-5-methyl-4-isoxazolepropionate (AMPA) receptor channels, which are involved in excitotoxic cell death (Choi, 1988; Planells-Cases et al., 2006).

Apart from neural cell death, other critically important pathophysiological processes that contribute to adverse outcome in ischemic stroke include formation of ionic edema, vasogenic edema and hemorrhagic conversion—all processes involving capillary endothelial cells (Simard et al., 2007). In the case of ionic edema formation, transcapillary flux of Na+ constitutes the seminal process that drives inflow of $H_2O$ into brain parenchyma, resulting in edema and swelling. In specific embodiments, NC channels play a role in this process. Thus, NC channels are implicated not only in primary neural cell death but in secondary neural cell death caused by endothelial dysfunction.

In recent years, study of ischemia/hypoxia-induced cell death has been dominated by discussion of apoptosis, a form of "delayed" programmed cell death that involves transcriptional up-regulation of death-related gene products, such as caspases. However, in stroke, only a fraction of cells undergo apoptotic death, with the majority of cells dying by oncotic/necrotic death (Lipton, 1999). The lesson from studies on apoptosis is that death, like so many other cellular events, is driven by gene expression and synthesis of new gene products, a concept that has not been fully embraced in studies on oncotic/necrotic death. Comprehensive understanding of the pathophysiology of ischemia/hypoxia requires a focus not only on constitutively expressed NC channels in cells undergoing ischemia hypoxia, including endothelial cells, but perhaps more importantly, on newly expressed NC channels whose transcription is driven by mechanisms involved in ischemia/hypoxia, namely, hypoxia and oxidative stress.

VIII. Non-Specific NC Channel Blockers in Ischemic Stroke

A number of studies have shown that pharmacological inhibition of NC channels reduces focal ischemic injury in rodent models of ischemic stroke. Although none of these pharmacological agents is uniquely specific for any single molecular entity, some have been shown to block TRP channels.

A. The NC Channel Blocker, Pinokalant

The isoquinoline derivative pinokalant (LOE 908 MS, (R,S)-(3,4-dihydro-6,7-dimethoxy-isoquinoline-1-yl)-2-phenyl-N,N-di [2-(2,3,4-trimethoxyphenyl)ethyl]-acetamide) blocks a variety of NC channels, including both receptor- and store-operated NC channels that mediate $Ca^{2+}$-entry, including:

(i) norepinephrine-activated $Ca^{2+}$-entry channels in adrenergic receptor-expressing Chinese hamster ovary cells (Kawanabe et al., 2001);

(ii) endothelin-1 (ET-1)-activated $Ca^{2+}$-entry channels in rat aorta myocytes (Zhang et al., 1999), A7r5 cells (Iwamuro et al., 1999; Miwa et al., 2000), rabbit internal carotid artery myocytes (Kawanabe et al., 2003), in C6 glioma cells (Kawanabe et al., 2001), in ET-1-expressing CHO cells (Kawanabe et al., 2002; Kawanabe et al., 2003) and in bovine adrenal chromaffin cells (Lee et al., 1999);

(iii) ATP- and N-formyl-L-methionyl-L-leucyl-L-phenyl-alanine (fMLP)-stimulated cation currents in HL-60 cells (Krautwurst et a., 1993);

(iv) vasopressin-induced cation current in A7r5 cells (Krautwurst et al., 1994);

(v) store-operated NC channels in human endothelial cells (Encabo et al., 1996); (however, in some cells, store-operated NC channels are resistant to pinokalant, reflecting a significant diversity of molecular constituents of these channels (Miwa et al., 1999; Flemming et al., 2003).

The primary candidate subunits of mammalian receptor- and store-operated NC channels are TRP proteins. Some of the above receptor- and store-operated NC channels that are blocked by pinokalant have been shown to be mediated by members of the TRP family, indicating that pinokalant, at least in part, is targeting some TRP channels. Thus, TRPC6 is a component of the norepinephrine-activated channel in rabbit portal vein, and it is believed that TRP6 plays an important role in mediating $Ca^{2+}$ influx in vascular smooth muscle (Large, 2002). TRPC1 has been implicated in ET-1-evoked arterial contraction (Beech, 2005). TRPC are thought to function as $Ca^{2+}$ entry channels operated by store-depletion as well as receptor-activated channels in a variety of cell types, including endothelial cells (Ahmmed and Malik, 2005). In the cockroach, Periplaneta Americana, the TRP (pTRP) channel is blocked by pinokalant (Wicher et al., 2006). However, block by pinokalant cannot be taken as evidence in and of itself that a TRP channel is involved in any given cationic current. Voltage-activated delayed rectifier K+ channels in PC12 cells and cortical neurons (Krause et al., 1998) and in HL-60 cells (Krautwurst et al., 1993) are also blocked by pinokalant.

Given its pharmacological profile as an inhibitor of NC channels, pinokalant has been evaluated as a potential neuroprotectant in rodent models of stroke (Christensen et al., 2005; Hoehn-Berlage et al., 1997; Li et al., 1999; Tatlisumak et al., 2000; Tatlisumak et al., 2000). Magnetic resonance imaging (MRI) was used to study the effect of pinokalant in a permanent (suture occlusion) middle cerebral artery occlusion (MCAO) model (Hoehn-Berlage et al., 1997). In untreated animals, the ischemic lesion volume [defined as the region in which the apparent diffusion coefficient (ADC) of water decreased to below 80% of control] steadily increased by approximately 50% during the initial 6 h of vascular occlusion. In treated animals, the ADC lesion volume decreased by approximately 20% during the same interval. After 6 h of vascular occlusion, blood flow was significantly higher in treated animals, and the volume of ATP-depleted and morphologically injured tissue representing the infarct core was 60-70% smaller. The volume of severely acidic tissue did not differ, indicating that pinokalant does not reduce the size of ischemic penumbra. These findings were interpreted as demonstrating that post-occlusion treatment delays the expansion of the infarct core into the penumbra for a duration of at least 6 h.

MRI was also used to study the effect of pinokalant in a temporary (90-min suture occlusion) MCAO model (Li et al., 1999; Tatlisumak et al., 2000; Tatlisumak et al., 2000). Before treatment, the DWI-derived infarct volume did not differ between the groups, whereas at 4 h after MCAO, it was significantly smaller in the treated group. A significant difference in ischemic lesion size was detected beginning 1.5 h after treatment. The size of the ischemic core was significantly smaller in the treatment group, while the size of the ischemic penumbra was similar in the two groups at 85 min after arterial occlusion. Postmortem, 2,3,5-triphenyltetrazolium chloride (TTC)-derived infarct volume was significantly attenuated in the pinokalant group and the neurological scores at 24 h were significantly better among the treated rats.

B. The NC Channel Blockers, the Fenamates

The fenamates, flufenamic acid, mefenamic acid and niflumic acid, for example, block $Ca^{2+}$-activated non-selective cation channels in a variety of cells (Gogelein et al., 1990; cho et al., 2003; Koivisto et al., 1998). Recently, it was shown in Chinese hamster ovary cells that flufenamic acid inhibits TRPM2 activated by extracellular $H_2O_2$(Naziroglu et al., 2006), although other channels are also blocked by these compounds.

Three fenamates (flufenamic acid, meclofenamic acid and mefenamic acid) were examined for their protective effect on retina under ischemic (glucose/oxygen deprivation) or excitotoxic conditions, using the isolated retina of chick embryo as a model (Chen et al., 1998). The retina is one of the most metabolically active tissues in mammalian bodies, and is particularly susceptible to ischemic damage. The fenamates protected the retina against the ischemic or excitotoxic insult, with only part of the neuroprotection attributed to inhibition of NMDA receptor-mediated currents, implicating non-NMDA NC channels in the response.

The effect of pre-treatment or post-treatment with mefenamate was evaluated in a rodent model of transient focal ischemia (Kelly and Auer, 2003). However, neither pre- nor post-ischemic administration of a dose previously shown effective in preventing epileptic neuronal necrosis was found to reduce necrosis in cortex, nor in any subcortical structures, which forced the authors to conclude that NC channel blockade with mefenamate affords no neuroprotection in this model.

C. The NC Channel Blocker, SKF 96365

SKF 96365 (SK&F 96365) (1-(beta-[3-(4-methoxy-phenyl)propoxy]-4-methoxyphenethyl)-1H-imidazole hydrochloride) is structurally distinct from the known $Ca^{2+}$ antagonists and shows selectivity in blocking receptor-mediated $Ca^{2+}$ entry, compared with receptor-mediated internal $Ca^{2+}$ release (Merritt et al., 1990). However, SKF 96365 is not as potent ($IC_{50}$~10 µM) or selective (also inhibits voltage-gated $Ca^{2+}$ entry) as would be desirable, so caution has been advised when using this compound (Merritt et al., 1990).

Measurements of intracellular $Ca^{2+}$ in human embryonic kidney (HEK)293 cells that stably expressed human TRP3 were used to show that SKF 96365 blocks TRP channels (Zhu et al., 1998). Expression of TRP3 in these cells forms a non-selective cation channel that opens after the activation of phospholipase C, but not after store depletion. Increased $Ca^{2+}$ entry in TRP3-expressing cells is blocked by high concentrations of SKF 96365 (Zhu et al., 1998).

The blood-brain barrier (BBB) serves as a critical organ in the maintenance of CNS homeostasis and is disrupted in a number of neurological disorders, including ischemic stroke. SKF 96365 was used to determine if $Ca^{2+}$ flux was important in mediating hypoxic/aglycemic effects on endothelial cells of the BBB (Brown and Davis, 2005; Brown et al., 2004; Abbruscato and Davis, 1999), which do not express voltage-dependent $Ca^{2+}$ channels. Expression of the tight junction protein occludin increased after hypoxic/aglycemic stress when cells were exposed to SKF 96365, which correlated with inhibition of the hypoxia-induced increase in permeability. Treatment with SKF 96365 increased intracellular $Ca^{2+}$ under normoglycemic conditions, and was protective against hypoxia-induced BBB disruption under normoglycemia.

D. The Cannabinoid 1 Receptor Blocker, Rimonabant and the Vanilloid Agonist, Capsaicin Rimonabant (SR141716A) is a compound that interacts with the G-protein coupled cannabinoid 1 (CB1) receptor (Henness et al., 2006). Rimonabant has also been suggested to block TRP channel vanilloid subfamily member 1 (TRPV1) (Pegorini et al., 2006). The link between CB1 and TRPV1 is reinforced by evidence that anandamide, an endogenous CB1 ligand, also activates TRPV1 (Pertwee, 2005). Capsaicin as well as $H^+$ (pH 5.9) are agonists known to activate TRPV1 (Gunthorpe et al., 2002; Van Der and Di, 2004).

In a rat model of ischemic stroke, rimonabant, given 30 min after initiation of permanent MCAO, reduced infarct volume by ~40% (Berger et al., 2004). The effects of rimonabant and capsaicin were investigated, with the aim of assessing the potential role of TRPV1 in a model of global cerebral ischemia in gerbils (Pegorini et al., 2006; Pegorini et al., 2005). Both compounds were found to antagonize the electroencephalographic changes, hyperlocomotion and memory impairment induced by global ischemia, and both were associated with a progressive survival of pyramidal cells in the CA1 subfield of the hippocampus. Notably, capsazepine, a selective TRPV1 antagonist, reversed both rimonabant-induced and capsaicin-induced neuroprotective effects. The authors interpreted their findings as suggesting that neuroprotection associated with capsaicin might be attributable, at least in part, to TRPV1 desensitization.

E. SUR1-Regulated $NC_{Ca-ATP}$ Channel

The $NC_{Ca-ATP}$ channel is a 35 pS cation channel that conducts all inorganic monovalent cations ($Na^+$, $K^+$, $Cs^+$, $Li^+$, $Rb^+$), but is impermeable to $Ca^{2+}$ and $Mg^{2+}$ (Chen and Simard, 2001). The fact that it conducts $Cs^+$ makes it easy to distinguish from $K_{ATP}$ channels with which it shares several properties (see below). Channel opening requires nanomolar concentrations of $Ca^{2+}$ on the cytoplasmic side. Channel opening is blocked by ATP (EC50, 0.79 µM), but is unaffected by ADP or AMP. Studies using a variety of organic monovalent cations indicate that the channel has an equivalent pore radius of 0.41 nm.

The $NC_{Ca-ATP}$ channel is believed to be composed of pore-forming and regulatory subunits. The regulatory subunit is sulfonylurea receptor 1 (SUR1), the same as that for $K_{ATP}$ channels in pancreatic β cells (Chen et al., 2003), and so $NC_{Ca-ATP}$ and pancreatic $K_{ATP}$ channels have pharmacological profiles that resemble each other closely. $NC_{Ca-ATP}$ channel opening is blocked by tolbutamide (EC50, 16.1 µM at pH 7.4) and glibenclamide (EC50, 48 nM at pH 7.4). Block by sulfonylurea is due to prolongation of and an increase in the probability of long closed states, with no effect on open channel dwell times or channel conductance. The potency of block by glibenclamide is increased ~8-fold at pH 6.8 (EC50, 6 nM), consistent with the weak acid needing to enter the lipid phase of the membrane to cause block (Simard et al., 2006). In the presence of ATP, channel opening is increased by diazoxide, but not pinacidil or cromakalin, as expected for SUR1 but not SUR2. The inhibitory effect of glibenclamide on opening of the $NC_{Ca-ATP}$ channel is prevented by antibody directed against one of the cytoplasmic loops of SUR1. Knockdown of SUR1 using antisense-oligodeoxynucleotide reduces SUR1 expression (Simard et al., 2006) and prevents expression of functional $NC_{Ca-ATP}$ channels.

The biophysical properties of the $NC_{Ca-ATP}$ channel resemble those of TRPM4. TRPM4 is a 25-pS channel that is also highly selective for monovalent cations, that has no significant permeation of $Ca^{2+}$, and that is activated by nanomolar $Ca^{2+}$ intracellularly (Launay et al., 2002; Harteneck, 2005), although it has not been shown to be sensitive to adenine nucleotides. TRPM4 and TRPM5 are currently the only molecularly identified $Ca^{2+}$-activated NC channels (Ullrich et al., 2005). Whereas TRPM5 is selectively expressed in the gastrointestinal system, expression of TRPM4 is ubiquitous (Harteneck, 2005).

The $NC_{Ca-ATP}$ channel is not constitutively expressed, but is expressed in the CNS under conditions of hypoxia or injury. The channel was first discovered in freshly isolated reactive astrocytes obtained from the hypoxic inner zone of the gliotic capsule (Chen and Simard, 2001; Chen et al., 2003). Since then, it has also been identified in neurons from the core of an ischemic stroke (Simard et al., 2006). In rodent models of ischemic stroke, the SUR1 regulatory subunit is transcriptionally up-regulated in neurons, astrocytes and capillary endothelial cells.

The consequence of channel opening has been studied in isolated cells that express the channel, by depleting ATP using Na azide or Na cyanide plus 2-deoxyglucose, or by using diazoxide. These treatments induce a strong inward current that depolarizes the cell completely to 0 mV. Morphological studies demonstrate that cells subsequently undergo changes consistent with cytotoxic edema (oncotic cell swelling), with formation of membrane blebs. Bleb formation is reproduced without ATP depletion by diazoxide (Chen and Simard, 2001). Cells later die predominantly by non-apoptotic, propidium iodide-positive necrotic death (Simard et al., 2006).

The effect of channel block by glibenclamide has been studied in vitro in reactive astrocytes that express the channel (Chen et al., 2003; Simard et al., 2006). In cells exposed to Na azide to deplete ATP, glibenclamide blocks membrane depolarization, significantly reduces blebbing associated with cytotoxic edema, and significantly reduces necrotic cell death.

The effect of channel block by glibenclamide has also been studied in 2 rodent models of ischemic stroke (Simard et al., 2006). Specificity of the drug for the target was based on administering a low dose by constant infusion (75-200 ng/h), which was predicted to yield serum concentrations of ~1-3 ng/ml (2-6 nM), coupled with the low pH of the ischemic tissues, to take advantage of the fact that glibenclamide is a weak acid that would preferentially target acidic tissues. In a rodent model of massive ischemic stroke with malignant cerebral edema associated with high mortality (68%), glibenclamide reduced mortality and cerebral edema (excess water) by half. In a rodent model of stroke induced by thromboemboli with delayed spontaneous reperfusion, glibenclamide reduced lesion volume by half, and its use was associated with cortical sparing attributed to improved leptomeningeal collateral blood flow due to reduced mass effect from edema.

In summary, the salient features of the $NC_{Ca\text{-}ATP}$ channel are that: (i) it is not constitutively expressed, but is transcriptionally up-regulated in association with an hypoxic insult; (ii) when expressed, it is not active but becomes activated when intracellular ATP is depleted, leading to cell depolarization, cytotoxic edema and necrotic cell death; (iii) block of the channel in vitro results in block of depolarization, cytotoxic edema and necrotic cell death induced by ATP depletion; (iv) block of the channel in vivo results in significant improvement in rodent models of ischemic stroke.

IX. Molecular Pathophysiology of Edema Following Ischemia

Dysfunction of cerebral capillaries due to ischemia and post-ischemic reperfusion results in a progressive alteration in permeability of the blood brain barrier (BBB), leading to formation of ionic edema, vasogenic edema and hemorrhagic conversion. When capillaries can no longer retain intravascular constituents such as $Na^+$, $H_2O$, serum proteins and blood, these substances enter into the extracellular space and cause swelling. It is common to divide edema into different subtypes (Joo and Klatzo, 1989; Betz et al., 1989; Ayata and Ropper, 2002) but it is not typical to include hemorrhagic conversion in the same discussion. Yet, it now appears that ionic edema, vasogenic edema and hemorrhagic conversion share important molecular antecedents, both transcriptional and pre-transcriptional, suggesting that hemorrhagic conversion may represent an end-stage in a process that manifests initially as edema.

Edema and hemorrhagic conversion are topics of great importance to clinicians who cope daily with their damaging consequences. Excellent reviews on these subjects have appeared (Ayata and Ropper, 2002; Young et al., 1994; Betz, 1996; Rosenberg, 1999). The present disclosure relates to methods of treating or preventing edema formation and hemorrhagic conversion.

A. Edema Versus Swelling

Edema is detrimental because it causes swelling (FIGS. 1A-1D). Swelling means that the volume occupied by a given mass of tissue is increased, due to tumor, edema, blood, etc. Swelling is harmful because of its effects on adjacent tissues, with these effects magnified by the fixed volume of the skull. Swollen tissues exert mechanical force on a surrounding shell of tissue, displacing it and increasing tissue pressure within it. When tissue pressure exceeds capillary pressure, capillary inflow is compromised, leading to ischemia, formation of edema and swelling of the shell (Hossmann and Schuier, 1980). Edema and swelling are both indicators and causes of injury.

B. Swelling Requires Active Blood Flow

Swelling implies that a new constituent is added to the extracellular space. Excluding tumor, the new constituent can only come from the vascular space. The absolute requirement for active blood flow is easily appreciated with a simple thought-experiment. Excision of a piece of tissue from a live brain, whether in the operating room or laboratory, will cause the cells within the tissue to die, exhibiting shifts in ionic and water content between extracellular and intracellular spaces that are characteristic of cytotoxic edema. However, such tissues will not swell, will not become heavier, and will show no ionic edema, vasogenic edema, or hemorrhagic conversion, simply because there is no source of new water, ions and blood. This thought-experiment reinforces the distinction between cytotoxic edema and the three pathophysiological processes (ionic edema, vasogenic edema and hemorrhagic conversion), with the latter three requiring blood flow to cause swelling.

With post-ischemic reperfusion, the requirement for active blood flow is fulfilled. In the case of unperfused tissue, there is a spatial gradient of ischemia/hypoxia, ranging from profound hypoxia in the core, to near-critical hypoxia in the penumbra, to normoxia further away. These zones are associated with different molecular and physiological responses (Hossmann, 1994). Ionic edema forms in the zone of perfused but severely ischemic tissue. In a rodent model of malignant cerebral edema studied 8 hours after permanent middle cerebral artery occlusion (FIG. 1B), the excess water of edema is localized overwhelmingly in perfused TTC(+) regions adjacent to the core, with minimal excess water in the poorly-perfused TTC(−) core (Simard et al., 2006). Magnetic resonance imaging confirms that edema is found first in peri-infarct regions that are perfused (Quast et al., 1993).

Edema fluid moves by bulk flow (convection) into the unperfused tissue. The driving force for this movement is the concentration gradient for the constituents that are moving, including $Na^+$ and $Cl^-$, and $H_2O$. Before equilibration, areas within the core will contain little or no excess electrolytes, whereas penumbral areas adjacent to infarct will contain an excess of electrolytes and water. The rate of accumulation of excess $Na^+$ in the core may be used to estimate the age of the infarct (Wang et al., 2000).

C. Starling's Principle

Over a century ago, Starling established the basic principles involved in formation of edema (Starling, 1896). According to Starling, understanding edema formation requires that two things be identified: (i) the driving force that "pushes" substances into the tissue; and (ii) the permeability pore that allows transcapillary passage of these substances from the intravascular to the extracellular space.

The driving force is determined by the sum of hydrostatic and osmotic pressure gradients. Hydrostatic pressure is determined by the difference between pre-capillary arteriolar and post-capillary venular pressures, which are influenced by blood pressure and tissue pressure. Osmotic pressure is determined by the concentrations of osmotically active particles in blood versus extracellular tissues. In the normal brain capillary, osmotic pressure plays a much more important role than hydrostatic pressure, due to the existence of tight junctions between endothelial cells that minimize this mechanism of fluid transfer across the capillary. Under pathological conditions, both osmotic and hydrostatic pressure gradients play critical roles in fluid transfer.

The second factor, the permeability pore, is determined by "passages" through and between the capillary endothelial cells (Hawkins and Davis, 2005). Passages through endothelial cells can be formed by ion channels, if those channels are expressed on both luminal and abluminal sides of endothelial cells. Also, reverse pinocytosis has been put forth as a mechanism by which substances can undergo transcapillary movement. Formation of passages between capillary endothelial cells implies either that cells contract, partially "retracting" cell borders, that cells loose tight junctions between themselves, or that the cells are totally lost, e.g., by necrotic death.

D. Cytotoxic Edema

Cytotoxic edema is a premorbid process that involves oncotic swelling of cells due to movement of osmotically active molecules (principally $Na^+$, $Cl^-$ and $H_2O$) from the extracellular to the intracellular space (Klatzo, 1987; Kimelberg, 1995; Go, 1997; Kempski, 2001). The terms "cytotoxic edema", "cellular edema", "oncosis" and "necrotic volume increase" are synonymous and refer to pathophysiological processes at the cellular level. With cytotoxic edema, no new constituent from the intravascular space is added and tissue swelling does not occur. However, cytotoxic edema creates the "driving force" for transcapillary formation of ionic and vasogenic edema, which do cause swelling.

An older definition of cytotoxic edema encompassed not only the definition as given here involving a strictly cellular disturbance, but also the concept of transcapillary water and electrolyte transport into parenchyma, i.e., ionic edema. Because distinct physiological processes are involved, however, we regard it as important to maintain independent definitions.

Movements of osmotically active molecules into the cell can occur either by primary active transport or secondary active transport. Primary active transport (ATP-dependent, $Na^+/K^+$ ATPase, etc.) requires continuous expenditure of energy, which is not readily available under conditions of ischemia (Sweeney et al., 1995; White et al., 2000). Secondary active transport uses energy stored in a pre-existing ionic gradients across the cell membrane (ion channels, $Na^+/K^+/Cl^-$ cotransporter, etcetera.) Because of the dysfunctional energy state that exists with ischemia, we focus on mechanisms that are largely independent of continuous expenditure of energy.

Two types of substances are involved in cytotoxic edema—primary drivers and secondary participants. Primary drivers are molecules that are more concentrated outside compared to inside the cell and that are normally extruded from the cell by primary active transport. Secondary participants are molecules for which no pre-existing electrochemical gradient normally exists, but for which a gradient is created by the primary drivers. If $Na^+$ is the primary driver, $Cl^-$ and $H_2O$ would be the secondary participants that move in order to maintain electrical and osmotic neutrality. Many types of $Cl^-$ channels normally exist in all cells of the CNS. Aquaporin channels that may aid bulk flow of $H_2O$ are up-regulated, at least in astrocytes, in CNS ischemia (Badaut et al., 2002; Amiry-Moghaddam and ottersen, 2003).

Different molecular mechanisms may be utilized for secondary active transport. For $Na^+$, conventional thinking asserts that in neurons and astrocytes, constitutively expressed $Na^+$ influx pathways, including tetrodotoxin-sensitive $Na^+$ channels, $Na^+/K^+/Cl^-$ cotransporter, N-methyl-D-aspartate receptor channels, etc., admit $Na^+$ during the course of normal activity or during "pathological depolarization" (Banasiak et al., 2004; Breder et al., 2000; Beck et al., 2003) and that, because of ischemia, newly admitted $Na^+$ cannot be extruded due to failure of $Na^+/K^+$ ATPase and other ATP-dependent transporters (yang et al., 1992).

Apart from constitutively expressed pathways, non-selective cation channels up-regulated by ischemia or oxidative stress may provide new pathways for $Na^+$ influx. Transient receptor potential channels (Aarts and Tymianski, 2005) and the sulfonylurea receptor 1 (SUR1)-regulated $NC_{Ca-ATP}$ channel (Simard et al., 2006; Chen and Simard, 2001; Chen et al., 2003) can act in this manner. The $NC_{Ca-ATP}$ channel is transcriptionally up-regulated within 2-3 hr of ischemia. Opening of this channel, which is triggered by ATP depletion, causes cell depolarization, cell blebbing, cytotoxic edema and oncotic cell death, all of which are prevented by blocking the channel.

Opening non-selective cation channels allows egress of $K^+$ from the cell, but movements of $Na^+$ and $K^+$ do not simply neutralize one another, because the cell is full of negatively charged proteins and other macromolecules that act to bind $K^+$, (Young and Constantini, 1994) resulting in a significantly greater inflow of $Na^+$ than outflow of $K^+$. The net inflow of $Na^+$ generates an osmotic force that drives influx of $H_2O$ typical of cytotoxic edema.

Cytotoxic edema is tied to cell death. With the inflow of $N^+$ down its concentration gradient, and the resultant inflow of $Cl^-$ and $H_2O$, the cell depolarizes, blebs or outpouchings form in the cell membrane, and eventually the membrane ruptures as the cell undergoes lysis-necrotic cell death (FIGS. 5A-5D) (Barros et al., 2001; Barros et al., 2002).

Cytotoxic edema (oncotic volume increase) may be contrasted with "apoptotic volume decrease" (Okada and Maeno, 2001). The former involves influx of $Na^+$, $Cl^-$ and $H_2O$, whereas the latter involves opening of $K^+$ selective channels resulting in $K^+$ efflux, which is accompanied by $Cl^-$ efflux and by loss of $H_2O$ from the cell. Apoptotic volume decrease results in cell shrinkage, which presages apoptotic cell death.

E. Driving Force for Edema Formation

The extracellular space of the brain is small compared to the intracellular space, constituting only 12-19% of brain volume (Go, 1997). Thus, movements of ions and water into cells during formation of cytotoxic edema results in depletion of these constituents from the extracellular space (Stiefel and Marmarou, 2002; Mori et al., 2002). Cytotoxic edema sets up a new gradient for $Na^+$ between the intravascular space and the extracellular space, which acts as a driving force for transcapillary movement of edema fluid. If neurons and astrocytes undergo necrotic death, joining their intracellular contents to that of the extracellular space, a concentration gradient for Na$^+$ is still set up across the BBB, again because the extracellular space of the brain is small compared to the intracellular space, as reflected by the high K$^+$ concentration and low Na$^+$ concentration of normal homogenized brain tissue (Young and Constantini, 1994), coupled with the fact that K$^+$ ions remain largely bound to negatively charged intracellular proteins and other macromolecules (Young and Constantini, 1994). Thus, whether or not cells are intact, cytotoxic edema and cell death create a transcapillary gradient that acts to drive subsequent movement of edema fluid.

F. Permeability Pores

In accordance with Starling's principle, the driving force across the BBB that is newly created by cytotoxic edema represents a form of potential energy that will not be expended unless the permeability properties of the BBB are changed. In the following sections, the permeability pore(s) are considered that permit fluxes to occur down concentration gradients across the capillary wall. The ischemia-induced changes in capillary permeability may be organized into three distinct phases (ionic edema, vasogenic edema and hemorrhagic conversion), based on the principal constituents that undergo transcapillary movement (FIGS. 2A-2C and 5A-5D). The 3 phases are considered to occur sequentially, but the likelihood and rapidity of transition from one phase to another probably depend on such factors as duration and depth of hypoxia during perfusion or prior to reperfusion. Thus, the reperfused capillary in the core that was completely ischemic is more likely to go on to the third phase than the hypoxic capillary at the edge of the penumbra.

1. First Phase—Formation of Ionic Edema

The earliest phase of endothelial dysfunction in ischemia is characterized by formation of ionic edema (Betz et al., 1989; Young and Constantini, 1994; Gotoh et al., 1985; Young et al., 1987; Betz et al., 1990). Formation of ionic edema involves transport of Na$^+$ across the BBB, which generates an electrical gradient for Cl$^-$ and an osmotic gradient for H$_2$O, thus replenishing Na$^+$, Cl$^-$ and water in the extracellular space that was depleted by formation of cytotoxic edema. As with cytotoxic edema, in ionic edema, the amount of Na$^+$ accumulation exceeds the amount of K$^+$ lost, giving a net inflow of Na$^+$ into edematous brain (Young and Constantini, 1994; Young et al., 19987).

Formation of ionic edema is clearly distinct from formation of vasogenic edema, as it involves abnormal Na$^+$ transport in the face of normal exclusion of protein by the BBB (Schuier and Hossmann, 1980; Todd et al., 1986; Goto et al., 1985; Todd et al., 1986). Early water influx (stage of ionic edema) is well correlated with Na$^+$ accumulation and precedes albumin influx (stage of vasogemic edema) by 6 hours or more. In this phase of ionic edema, the BBB remains "intact", i.e., macromolecules do not permeate it. Thus, influx of Na$^+$ cannot be accounted for by leakiness of the BBB, reverse pinocytosis, loss of tight junctions or other physical processes that would also allow transport of serum macromolecules along with Na$^+$.

As with cytotoxic edema, two mechanisms can account for selective flux of Na$^+$ across the BBB, primary active transport and secondary active transport, but again, we focus only on secondary active transport mechanisms that depend on preexisting electrochemical gradients. Unlike neurons and astrocytes, endothelial cells do not express voltage-dependent channels that conduct Na$^+$ (Nilius and Droogmans, 2001). They express ligand-gated channels that could act in this manner (Nilius and Droogmans, 2001), but no evidence exists to show their involvement.

The secondary active Na$^+$/K$^+$/Cl$^-$ cotransporter (Russell, 2000), located mostly on the luminal side of endothelium, has been postulated to be involved in formation of ionic edema, based on salutary effects of pre-ischemic administration of the cotransporter inhibitor, bumetanide (O'Donnell et al., 2004). However, this mechanism is said to require the participation of abluminal Na$^+$/K$^+$ ATPase to complete transcapillary flux of Na$^+$ (O'Donnell et al., 2004). Thus, invoking this mechanism in the context of ischemia is problematic, although it may be relevant should energy restoration occur with timely reperfusion.

Data from the inventor's laboratory implicate SUR1-regulated NC$_{Ca-ATP}$ channels in formation of ionic edema. Post-ischemic block of the channel by low-dose glibenclamide reduces edema by half (Simard et al., 2006). Involvement of NC$_{Ca-ATP}$ channels would imply that formation of ionic edema does not proceed by co-opting existing membrane proteins, but requires instead the expression of new protein by endothelial cells of ischemic but perfused capillaries.

A mechanism involving Na$^+$-conducting channels in transcapillary flux of Na$^+$ represents little more than a description of cytotoxic edema of endothelial cells. Channels on the luminal side contribute to cytotoxic edema of endothelial cells, providing an influx pathway for Na$^+$, whereas channels on the abluminal side act to relieve this cytotoxic edema by providing an efflux pathway for Na$^+$ down its concentration gradient from the cell into the extracellular space. Obviously, this relief mechanism completes the pathway for transcapillary flux of Na$^+$. As noted previously, Cl$^-$ and H$_2$O follow via their own respective channels, completing the process of formation of ionic edema. Although Cl$^-$ channels are present (Nilius and Droogmans, 2001), expression of aquaporin channels by endothelium in situ remains to be clarified, with aquaporin-1 but not aquaporin-4 possibly playing a role in ischemia (Dolman et al., 2005).

In this stage of ionic edema, BBB integrity is maintained, capillary tight junctions are preserved, and macromolecules are excluded from brain parenchyma. Thus, the driving force for formation of edema is determined only by osmotic pressure gradients, with hydrostatic pressure gradients being essentially irrelevant.

2. Second Phase—Formation of Vasogenic Edema

The second phase of endothelial dysfunction is characterized by "breakdown" of the BBB, with leakage of plasma proteins into extracellular space. Macromolecules such as albumin, IgG and dextran, to which the BBB is normally impermeable, now pass readily across the endothelial barrier.

Vasogenic edema may be considered an ultrafiltrate of blood (Vorbrodt et al., 1985), suggesting that the permeability pore is now quite large. The permeability pore that allows pass age of larger molecules across the BBB has not been uniquely identified, and may have contributions from more than one mechanism. Any physical disruption of the capillary must be relatively limited, however, to account for egress of a proteinacious ultrafiltrate without passage of erythrocytes.

Several mechanisms have been proposed to account for changes in permeability that gives rise to vasogenic edema, including reverse pinocytosis (Castejon et al., 1984), disruption of Ca$^{2+}$ signaling (Brown and Davis, 2002), actin polymerization-dependent endothelial cell rounding or retraction with formation of inter-endothelial gaps, uncoupling of tight junctions, and enzymatic degradation of basement membrane. Formation of inter-endothelial gaps is observed with many inflammatory mediators (Ahmmed and Malik, 2005), including mediators up-regulated in cerebral ischemia such as thrombin (Satpathy et al., 2004). Thrombin-induced endothelial cell retraction may account for vasogenic edema associated not only with focal ischemia but also with intracerebral hematoma (Lee et al., 1996; Hua et al., 2003). Uncoupling of endothelial tight junctions is observed following up-regulation of vascular endothelial growth factor (VEGF), which increases hydraulic conductivity in isolated perfused microvessels, increases vascular permeability and promotes formation of edema (Weis and Cheresh, 2005). Antagonism of VEGF reduces edema associated with post-ischemia reperfusion (Van et al., 1999). Degradation of basement membrane required for structural integrity of capillaries is observed with enzymes that are up-regulated in cerebral ischemia, especially the matrix metalloproteinases (MMP), MMP-9 (gelatinase B) and MMP-2 (gelatinase A) (Asahi et al., 2001; Asahi et al., 2000; Mun-Bryce and rosenberg, 1998; Fukuda et al., 2004). Ischemia activates latent MMPs and causes de novo synthesis and release of MMPs (Asahi et al., 2001; Romanic et al., 1998; Kolev et al., 2003). MMP inhibitors reduce ischemia/reperfusion-related brain edema (Lapchak et al., 2000; Pfefferkorn and Rosenberg, 2003). Other proteins that are up-regulated and whose function results in degradation of the BBB include nitric oxide synthase (NOS), either iNOS (ladecola et al., 1996) or nNOS (Sharma et al., 2000). Notably, these various molecular mechanisms establish the specific embodiment that constitutively expressed participants play only a limited role, and up-regulation of a family of proteins that alter BBB permeability is the norm.

Once BBB integrity is lost, capillaries behave like "fenestrated" capillaries, and both the hydrostatic and osmotic pressure gradients must be considered to understand edema formation. Determinants of hydrostatic pressure, including systemic blood pressure and intracranial pressure, now assume an important role. Determinants of osmotic pressure now consist of all osmotically active molecules, including $Na^+$ and macromolecules. There are implications regarding clinical management: (i) systemic blood pressure must be sufficient to perfuse the brain, but excess pressure will promote edema formation (Kogure et al., 1981); (ii) intracranial pressure, which determines tissue pressure, must be lowered to appropriate levels, but lowering it too much will promote edema formation. Optimization of parameters to achieve these conflicting goals is difficult. Treatments generally include use of osmotically active agents such as mannitol, but their effects may only be temporizing.

These concepts shed light on reasons for mixed outcomes following decompressive craniectomy (Kilincer et al., 2005; Mori et al., 2004), a procedure that abruptly lowers tissue pressure. In contrast to the stage of ionic edema, when hydrostatic pressure and therefore tissue pressure are unimportant for edema formation, in the stage of vasogenic edema, tissue pressure is a critical determinant of edema formation. Decompressive craniectomy may be safe if performed early, during the stage of ionic edema when the BBB is intact, as it may aid in restoring reperfusion by reducing intracranial pressure. By contrast, decompressive craniectomy performed later, during the stage of vasogenic edema, will decrease tissue pressure, drive formation of vasogenic edema, and thus may have an unintended deleterious effect. Brain imaging may guide the timing of treatment based on detection of these stages. Diffusion restriction on MRI correlates with the cytotoxic stage, while early hypodensity prior to mass effect on CT scan may be useful to assess ionic versus vasogenic edema prior to decompressive craniectomy (Knight et al., 1998; Latour et al., 2004).

3. Third Phase—Hemorrhagic Conversion

The third phase of endothelial dysfunction is marked by catastrophic failure of capillary integrity, during which all constituents of blood, including erythrocytes, extravasate into the parenchyma. Up to 30-40% of ischemic strokes undergo spontaneous hemorrhagic conversion, a complication that is more prevalent and more severe with use of thrombolytic stroke therapy (Asahi et al., 2000; Jaillard et al., 1999; Larrue et al., 1997). Hemorrhagic conversion, the transformation of a bland infarct into a hemorrhagic infarct after restoration of circulation, accounts for a major cause of early mortality in acute-stroke patients, ranging from 26-154 extra deaths per 1000 patients (Hacke et al., 1995; Hacke et al., 1998; Multicentre Acute Stroke Trial, 1995; National Institute of Neurological Disorders and Stroke rt-PA Stroke Study Group, 1995; Donnan et al., 1996).

Prolonged ischemia, aggravated by reperfusion, causes initial dysfunction and later death of capillary endothelial cells (del Zoppo et al., 1998; Hamann et al., 1999; Lee and Lo, 2004). As this process evolves, the BBB is increasingly compromised, capillaries become leaky, and eventually they lose their physical integrity. In the end, capillaries can no longer contain circulating blood, resulting in formation of petechial hemorrhages—hemorrhagic conversion. The close connection between BBB compromise and hemorrhagic conversion is supported by both animal (Knight et al., 1998) and human studies (Latour et al., 2004; Warach and Latour, 2004; NINDS t-PA Stroke Study Group, 1997) that predict hemorrhagic conversion following thrombolytic therapy based on pre-existing BBB dysfunction manifested either as gadolinium enhancement or hypodensity on computed tomographic imaging.

Hemorrhagic conversion is probably a multifactorial phenomenon due to reperfusion injury and oxidative stress. Mechanisms may include plasmin-generated laminin degradation, endothelial cell activation, transmigration of leukocytes through the vessel wall and other processes (Hamann et al., 1999; Wang and Lo, 2003). Factors important during the phase of vasogenic edema also participate. Exogenous VEGF administered intravascularly early following reperfusion aggravates hemorrhagic transformation (Abumiya et al., 2005). Dysregulation of extracellular proteolysis plays a key role in hemorrhagic transformation, with MMPs being critical participants (Fukuda et al., 2004; Wang and Lo, 2003; Heo et al., 1999; Sumii and Lo, 2002). As with vasogenic edema, inhibition of BBB proteolysis reduces hemorrhagic conversion with reperfusion (Lapchak et al., 2000; Pfefferkorn and Rosenberg, 2003). Finally, oncotic death of endothelial cells, mediated by SUR1-regulated $NC_{Ca\text{-}ATP}$ channels, would also be expected to give rise to hemorrhagic conversion.

As regards driving force, everything noted above for the "fenestrated capillary" associated with vasogenic edema holds in this phase as well. Theoretically, adding blood into the parenchyma and thereby increasing tissue pressure may reduce the hydrostatic driving force, but it does so at an untenable cost to the organ, adding mass that contributes to increased intracranial pressure, adding the exquisitely toxic oxidant, hemoglobin, and inciting a robust inflammatory response, all of which contribute adversely to outcome (Rosenberg, 2002; Zheng and Yenari, 2004; Price et al., 2003). Implications for clinical management are similar to those for the previous stage, but optimization of parameters to achieve the conflicting goals is now appreciably more difficult.

G. Energy Considerations

The conceptualization of edema formation depicted here is grounded on physiological principals originally enunciated over a century ago. The power of this conceptualization lies in its ability to explain massive fluxes of ions and water into brain parenchyma despite the severe energy constraints typically encountered with ischemia. During formation of ionic edema, movements of ions and water occur by secondary active transport mechanisms, powered by concentration gradients originally formed by exclusion of $Na^+$ from neurons and astrocytes. During formation of vasogenic edema as well as during hemorrhagic conversion, movements of plasma and blood into parenchyma are driven by hydrostatic pressure generated by the heart. Thus, vast quantities of ions, macromolecules, water and blood can move into the parenchyma with no new energy expenditure by the brain.

On the other hand, this conceptualization requires new protein synthesis induced by ischemia in order to alter permeability of the BBB. One important example is aquaporin 4 (AQP4), now strongly implicated in ischemia-induced edema (Badaut et al., 2002; Taniguchi et al., 2000). As for the SUR1-regulated $NC_{Ca-ATP}$ channel, which appears to be integral to formation of ionic edema, the need for protein synthesis has been shown at least for the SUR1 regulatory subunit of this channel, which is transcriptionally up-regulated in ischemia (Simard et al., 2006). In addition, the need for protein synthesis is true for prothrombin (Riek-Burchardt et al., 2002; Striggow et al., 2001), MMP-9 (Asahi et al., 2001; Asahi et al., 2000; Planas et al., 2000). VEGF (Croll and Wiegand, 2001) and iNOS, which play important roles in vasogenic edema and hemorrhagic conversion. New protein synthesis requires what is presumably a limited, perhaps "one-time" energy expenditure—what may ultimately be the last such expenditure on the way to self destruction of capillaries. Notably, the burden for new protein synthesis is left largely, though not exclusively, to endothelial cells in capillaries that are still perfused, and thus it is most likely to maintain a positive energy balance the longest in the face of an ischemic insult.

H. Transcriptional Program

What links the various proteins, newly synthesized by ischemic endothelium, that are tied to progressive capillary dysfunction? Because the 3 phases of capillary dysfunction arise from a severe hypoxic insult, with or without free radicals generated upon reperfusion, synthesis of these proteins must be regulated by a transcriptional program involving hypoxia- or redox-sensitive transcription factors such as activator protein-1 (AP-1) (dimers of Fos, Jun and related oncoproteins that activate immediate early genes (IEGs) (Sng et al., 2004)), hypoxia inducible factor-1 (HIF-1), Sp-1 and nuclear factor-□B (NF-□B). Each of these factors is activated by focal cerebral ischemia (Simard et al., 2006; Kogure and Kato, 1993; Salminene et al., 1995; Han et al., 2003; Matrone et al., 2004; Schneider et al., 1999; Hermann et al., 2005). HIF is activated when oxygen tension falls below 5% (40 mmHg), and is progressively activated with a decrease in oxygen tension down to 0.2-0.1% (1.6-0.8 mmHg), close to anoxia (Pouyssegur et al., 2006). Analysis of the promoter regions of the various proteins reveals the presence of one or more putative binding sites for each of these transcription factors (FIGS. 7A-7F). Definitive evidence for involvement of all 4 factors in transcriptional regulation of proteins involved in cerebral edema remains to be obtained, but some pieces of the matrix have been filled in, including for AQP4 (AP-1, Sp-1) (Umenishi and Verkman, 1998), SUR1 (Sp-1) (Simard et al., 2006; Ashfield and Ashcroft, 1998; Hernandez-Sanchez et al., 1999), prothrombin (Sp-1) (Ceelie et al., 2003), VEGF (Sp-1, HIF-1, AP-1) (Hasegawa et al., 2006; Pore et al., 2006; Nordal et al., 2004; Sainikow et al., 2002) and MMP-9 (NF-□B) (Kolev et al., 2003; Bond et al., 2001).

Other hypoxia- or redox-activated transcription factors that are involved may be determined by standard methods in the art. Nevertheless, the functional grouping of these 4 factors affirms the concept of a transcriptional program which, when unleashed, initiates a sequential dynamic alteration in BBB characteristics that can lead to demise of the organ and ultimately, demise of the organism.

X. Coronary Artery Bypass Graft

Coronary artery disease is a major medical problem affecting morbidity and mortality worldwide. Coronary arteries, as well as other blood vessels, can become obstructed, partially or wholly, by for example atherosclerotic plaque. Plaque formation can lead to the impairment of the efficiency of the heart's physiological action and can lead to the inhibition of blood flow to heart, which can lead to heart attack and death. In certain instances, damaged cardiac vasculature (e.g., a narrowed lumen due to atherosclerotic plaque formation) can be treated by techniques such as, for example, balloon angioplasty or percutaneous transluminal coronary angioplasty. In other instances, surgical bypass of the damaged cardiac vessel is necessary.

Coronary artery bypass graft ("CABG") involves performing an anastomosis on a diseased coronary artery to reestablish blood flow to an ischemic portion of the heart. Improved long-term survival has been demonstrated by bypassing the left anterior descending artery with a left internal mammary artery, which has encouraged surgeons to extend revascularization with arterial grafts to all coronary arteries. Since the internal mammary artery can only be used for two CABG procedures (using right and left internal mammary arteries, respectively), where multiple-vessels need to be bypassed, other arteries or veins are used. Such other arteries or veins that have been used include, for example, the right gastroepiploic artery, the inferior epigastric artery, the internal mammary artery (also known as the internal thoracic artery), the radial artery, and the saphenous vein. The internal mammary artery is the most common arterial conduit used for CABG; yet, despite its widespread use and superior patency when compared to the saphenous vein (Grondin et al., 1984, Circulation, 70 (suppl I): 1-208-212; Camereon et al., 1996, N Engl J Med, 334: 216-219), the saphenous vein continues to be one of the most popular conduits for CABG (Roubos et al., 1995, Circulation, 92 (9 Suppl) II31-6).

During a typical coronary artery bypass graft procedure using the saphenous vein, a section of the saphenous vein is surgically removed from the leg and the graft is retained ex vivo (out of the body) for a length of time prior to attachment to another blood vessel within the body (Angelini and Jeremy, 2002, Biorheology, 39 (3-4): 491-499). In a bypass operation involving such a venous graft, the graft is harvested by a surgically invasive procedure from the leg of the patient and then stored for up to several hours ex vivo (e.g., four hours) as surgery is performed on the heart. Although there are variations in methodology in surgical preparation of the heart, the first part of the procedure typically requires an incision through the patient's sternum (sternotomy), and in one technique, the patient is then placed on a bypass pump so that the heart can be operated on while not beating. In alternative techniques, the heart is not stopped during the procedure. Having harvested and stored the saphenous vein or arterial blood vessel conduit and upon completion of the surgery to prepare the heart for grafting, the bypass procedure is performed. A precise surgical procedure is required to attach the bypass graft to the coronary artery (anastomosis), with the graft being inserted between the aorta and the coronary artery. The inserted venous/arterial segments/transplants act as a bypass of a blocked portion of the coronary artery and thus provide for an unobstructed flow of blood to the heart. More than 500,000 bypass procedures are performed in the United States every year. The overall short and long term success of the CABG procedure is dependent on several factors including the condition of the graft used, which itself depends on any form of damage during the removal of the graft from the body or deterioration or damage of the graft due to storage conditions. In such circumstances, the short term detrimental effect can be potentially lethal thrombotic disease as a result of inadequate blood flow because of a changed phenotype of the graft due to its deterioration or damage during the removal or storage stage. Possible long term detrimental effects include, for example, the vein graft itself becoming diseased, stenosed, or occluded. In this case, the diseased or occluded saphenous vein grafts are associated with acute ischemic syndromes necessitating some form of intervention. It is therefore of critical importance not only that care be taken in the surgical procedure to remove the blood vessel to be used as the graft in surgical bypass procedures including CABG, but, also that no deterioration or damage occurs in the storage period of the graft prior to attachment to another blood vessel and the resumption of blood flow in that vessel.

In certain embodiments, any vascular graft and any vein/artery (including, for example, saphenous vein, tibial artery (including, for example, posterior tibial artery), mammary artery, radial artery, or any other vein/artery (including, for example, infrainguinal, popliteal, and distal leg arteries)) are included in the invention described herein. Furthermore, the invention is not restricted to nature of the vascular graft with respect to recipient and its origin (i.e., the graft can be either heterologous in nature or autologous in nature). In other certain embodiments, the artery or vein that is to be used for a bypass procedure can be stored in compositions comprising glyburide or other compositions of the invention prior to the surgical procedure whereby attachment of the bypass graft to the coronary artery (anastomosis) is performed. In further embodiments, compositions comprising glyburide or other compositions of the invention can be combined with an organ preservation solution or glyburide or other compositions of the invention can be used with saline for CABG or other transplantation procedure (including, for example, kidney transplant, liver transplant, heart transplant, limb transplant, skin graft, or any other organ transplant). An organ preservation solution includes, for example, Stanford University solution (see, e.g., Swanson et al., 1988, Journal of Heart Transplantation, 7(6): 456-467); Collins solution; modified Collins solution (see, e.g., Maurer et al., 1990, Transplantation Proceedings, 22(2): 548-550; Swanson et al., supra); University of Wisconsin solution (see, e.g., U.S. Pat. No. 4,798,824, issued to Belzer et al.); modified University of Wisconsin solution (Yeh et al., Ann Thorac Surg. 1990 June; 49(6):932-9); Columbia University solution (see, e.g., U.S. Pat. Nos. 5,552,267 and 5,370,989, and Kayano et al., 1999, J. Thoracic Cardiovascular Surg. 118: 135-144); histidine-tryptophan-ketoglutarate (HTK) solution (see, e.g., Ku et al., Transplantation. 1997 Oct. 15; 64(7):971-5); Celsior (see, e.g., Janssen et al., Transplant International (2003), 16(7): pp. 515-522); isotonic saline solutions, that may contain, in various proportions, salts, sugars, osmotic agents, local anesthetic, buffers, and other such agents (see, e.g., Berdyaev et al., U.S. Pat. No. 5,432,053; Belzer et al.); ViaSpan® (see, e.g., U.S. Pat. Nos. 4,798,824, 4,879,283; and 4,873,230; Taylor, U.S. Pat. No. 5,405,742; Dohi et al., U.S. Pat. No. 5,565,317; Stern et al., U.S. Pat. Nos. 5,370,989 and 5,552,267); solutions comprising pyruvate, inorganic salts supporting cell membrane potential and albumin or fetal calf serum (see, e.g., U.S. Pat. No. 5,066,578); solutions comprising one or more phosphatidic acids or sugars, and lysophosphotidic acids or sugars, together with enhancers such as albumen, optionally delivered in liposomal compositions (see, e.g., U.S. Pat. Nos. 6,495,532 and 6,004,579); other organ preservation solutions (see, e.g., U.S. Pat. No. 7,220,538); or any combination of the foregoing.

In other further embodiments, compositions of the invention comprise glyburide, saline, and db-cAMP (regarding the use of db-cAMP see, e.g., Sakaguchi T, Asai T, Belov D, Okada M, Pinsky D J, Schmidt A M, Naka Y. Influence of ischemic injury on vein graft remodeling: role of cyclic adenosine monophosphate second messenger pathway in enhanced vein graft preservation. J Thorac Cardiovasc Surg. 2005 January; 129(1):129-37). It will be understood that other SUR1 antagonists may be used in place of, or in addition to glyburide, as listed and discussed elsewhere in the application, and that blockers of TRPM4 channels, such as a fenamate, as listed and discussed elsewhere in the application, may also be used, in addition to, or in place of, a SUR1 antagonist.

XI. Organ Transplanation

In certain embodiments, the invention provides compositions for preserving and/or maintaining a cell, tissue, or organ in vivo, ex vivo and/or in vitro, as well as methods of making and using these compositions. In particular embodiments, the invention is drawn to using the compositions and methods described herein to preserve an organ, limb, cell, or tissue to be transplanted or re-attached. An organ includes, for example, solid organs (e.g., heart, kidney, liver, lung, pancreas, small bowel and other organ of the gastrointestinal tract) and functional parts thereof (e.g., lobes of a liver, kidney, lung, and the like). A Cell and tissue includes, for example, cornea, retina, bone, heart valves, tendons, ligaments, cartilage, vasculature, skin, bone marrow, blood cells, stem cells, and other tissues and cells derived from the body.

Such compositions and treatments using these compositions may be administered before an expected or possible ischemic or ischemic/hypoxic incident; may be administered during an ischemic or ischemic/hypoxic incident; and/or may be administered following an ischemic or ischemic/hypoxic incident. For example, an organ removed from a patient for later placement in the patient's body (e.g., a blood vessel used in heart bypass surgery) may be treated before, during, and/or after removal from its place of origin, and may be treated before, during, and/or after its placement in its new location. For further example, an organ removed from an organ donor for later transplantation into a different patient's body (e.g., a liver, kidney, lung, pancreas or heart used in transplant surgery) may be treated before, during, and/or after removal from the organ donor, and may be treated before, during, and/or after its placement in its new location in the patient receiving the organ. The organs may be stored in compositions having features of the invention, such as compositions including SUR1 antagonists at concentrations effective to inhibit the $NC_{Ca-ATP}$ channel, and/or including TRPM4 antagonists at concentrations effective to inhibit the $NC_{Ca-ATP}$ channel, and/or including agents that inhibit the expression and or function of $NC_{Ca-ATP}$ channel or any of its consitutents (e.g., SUR1 receptor and TRPM4 channel) and/or including other therapeutic compounds and agents, as discussed elsewhere in the application.

XII. Combinatorial Therapeutic Compositions

The present invention includes a combinatorial therapeutic composition comprising an antagonist of the $NC_{Ca-ATP}$ channel and another therapeutic compound, such as a cation channel blocker and/or an antagonist of a specific molecule, such as VEGF, MMP, NOS, thrombin, and so forth.

A. Inhibitors of $NC_{Ca-ATP}$ Channel

According to a specific embodiment of the present invention, the administration of effective amounts of the active compound can block the channel, which if it remained open would lead to neural cell swelling and cell death. A variety of antagonists to SUR1 are suitable for blocking the channel. Examples of suitable SUR1 antagonists include, but are not limited to glibenclamide, tolbutamide, repaglinide, nateglinide, meglitinide, Mitiglinide, iptakalim, endosulfines, LY397364, LY3 89382, gliclazide, glimepiride, MgADP, and combinations thereof. In a preferred embodiment of the invention the SUR1 antagonists is selected from the group consisting of glibenclamide and tolbutamide. Still other therapeutic "strategies" for preventing neural cell swelling and cell death can be adopted including, but not limited to methods that maintain the neural cell in a polarized state and methods that prevent strong depolarization.

The present invention comprises modulators of the channel, for example one or more agonists and/or one or more antagonists of the channel. Examples of antagonists or agonists of the present invention may encompass respective antagonists and/or agonists identified in US Application Publication No. 20030215889, which is incorporated herein by reference in its entirety. One of skill in the art is aware that the $NC_{Ca-ATP}$ channel is comprised of at least two subunits: the regulatory subunit, SUR1, and the pore forming subunit.

1. Exemplary SUR1 Inhibitors

In certain embodiments, antagonists to sulfonylurea receptor-1 (SUR1) are suitable for blocking the channel. Examples of suitable SUR1 antagonists include, but are not limited to glibenclamide, tolbutamide, repaglinide, nateglinide, meglitinide, Mitiglinide, iptakalim, endosulfines, LY397364, LY389382, glyclazide, glimepiride, estrogen, estrogen related-compounds estrogen related-compounds (estradiol, estrone, estriol, genistein, non-steroidal estrogen (e.g., diethystilbestrol), phytoestrogen (e.g., coumestrol), zearalenone, etc.) and combinations thereof. In a preferred embodiment of the invention the SUR1 antagonists is selected from the group consisting of glibenclamide and tolbutamide. Yet further, another antagonist can be MgADP. Other antagonist include blockers of $K_{ATP}$ channels, for example, but not limited to tolbutamide, glyburide (1[p-2 [5-chloro-O-anisamido)ethyl] phenyl] sulfonyl]-3-cyclohexyl-3-urea); chlopropamide (1-[[(p-chlorophenyl)sulfonyl]-3-propylurea; glipizide (1-cyclohexyl-3[[p-[2(5-methylpyrazine carboxamido) ethyl] phenyl] sulfonyl] urea); or tolazamide(benzenesulfonamide-N-[[(hexahydro-1H-azepin-1yl)amino] carbonyl]-4-methyl).

2. Modulators of SUR1 Transcription and/or Translation

In certain embodiments, the modulator can comprise a compound (protein, nucleic acid, siRNA, etc.) that modulates transcription and/or translation of SUR1 (regulatory subunit), TRPM4, and/or the molecular entities that comprise the pore-forming subunit.

3. Transcription Factors

Transcription factors are regulatory proteins that binds to a specific DNA sequence (e.g., promoters and enhancers) and regulate transcription of an encoding DNA region. Thus, transcription factors can be used to modulate the expression of SUR1. Typically, a transcription factor comprises a binding domain that binds to DNA (a DNA-binding domain) and a regulatory domain that controls transcription. Where a regulatory domain activates transcription, that regulatory domain is designated an activation domain. Where that regulatory domain inhibits transcription, that regulatory domain is designated a repression domain. More specifically, transcription factors such as Sp1, HIF1, and NFB can be used to modulate expression of SUR1.

In particular embodiments of the invention, a transcription factor may be targeted by a composition of the invention. The transcription factor may be one that is associated with a pathway in which SUR1 is involved. The transcription factor may be targeted with an antagonist of the invention, including siRNA to downregulate the transcription factor. Such antagonists can be identified by standard methods in the art, and in particular embodiments the antagonist is employed for treatment and or prevention of an individual in need thereof. In an additional embodiment, the antagonist is employed in conjunction with an additional compound, such as a composition that modulates the $NC_{Ca-ATP}$ channel of the invention. For example, the antagonist may be used in combination with an inhibitor of the channel of the invention. When employed in combination, the antagonist of a transcription factor of a SUR1-related pathway may be administered prior to, during, and/or subsequent to the additional compound.

4. Antisense and Ribozymes

An antisense molecule that binds to a translational or transcriptional start site, or splice junctions, are ideal inhibitors. Antisense, ribozyme, and double-stranded RNA molecules target a particular sequence to achieve a reduction or elimination of a particular polypeptide, such as SUR1. Thus, it is contemplated that antisense, ribozyme, and double-stranded RNA, and RNA interference molecules are constructed and used to modulate SUR1 expression.

5. Antisense Molecules

Antisense methodology takes advantage of the fact that nucleic acids tend to pair with complementary sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases, such as inosine, 5-methylcytosine, 6-methyladenine, hypoxanthine and others, in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNAs, are employed to inhibit gene transcription or translation or both within a host cell, either in vitro or in vivo, such as within a host animal, including a human subject.

Antisense constructs are designed to bind to the promoter and other control regions, exons, introns or even exon-intron boundaries of a gene. It is contemplated that the most effective antisense constructs may include regions complementary to intron/exon splice junctions. Thus, antisense constructs with complementarity to regions within 50-200 bases of an intron-exon splice junction are used. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

It is advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

6. RNA Interference

It is also contemplated in the present invention that double-stranded RNA is used as an interference molecule, e.g., RNA interference (RNAi). RNA interference is used to "knock down" or inhibit a particular gene of interest by simply injecting, bathing or feeding to the organism of interest the double-stranded RNA molecule. This technique selectively "knock downs" gene function without requiring transfection or recombinant techniques (Giet, 2001; Hammond, 2001; Stein P, et al., 2002; Svoboda P, et al., 2001; Svoboda P, et al., 2000).

Another type of RNAi is often referred to as small interfering RNA (siRNA), which may also be utilized to inhibit SUR1. A siRNA may comprises a double stranded structure or a single stranded structure, the sequence of which is "substantially identical" to at least a portion of the target gene (See WO 04/046320, which is incorporated herein by reference in its entirety). "Identity," as known in the art, is the relationship between two or more polynucleotide (or polypeptide) sequences, as determined by comparing the sequences. In the art, identity also means the degree of sequence relatedness between polynucleotide sequences, as determined by the match of the order of nucleotides between such sequences. Identity can be readily calculated. See, for example: Computational Molecular Biology, Lesk, A. M., ed. Oxford University Press, New York, 1988; Biocomputing: Informatics and Genome Projects, Smith, D. W., ea., Academic Press, New York, 1993, and the methods disclosed in WO 99/32619, WO 01/68836, WO 00/44914, and WO 01/36646, specifically incorporated herein by reference. While a number of methods exist for measuring identity between two nucleotide sequences, the term is well known in the art. Methods for determining identity are typically designed to produce the greatest degree of matching of nucleotide sequence and are also typically embodied in computer programs. Such programs are readily available to those in the relevant art. For example, the GCG program package (Devereux et al.), BLASTP, BLASTN, and FASTA (Atschul et al.,) and CLUSTAL (Higgins et al., 1992; Thompson, et al., 1994).

Thus, siRNA contains a nucleotide sequence that is essentially identical to at least a portion of the target gene, for example, SUR1, or any other molecular entity associated with the $NC_{Ca-ATP}$ channel such as the pore-forming subunit. One of skill in the art is aware that the nucleic acid sequences for SUR1 are readily available in GenBank, for example, GenBank accession L40624, which is incorporated herein by reference in its entirety. Preferably, the siRNA contains a nucleotide sequence that is completely identical to at least a portion of the target gene. Of course, when comparing an RNA sequence to a DNA sequence, an "identical" RNA sequence will contain ribonucleotides where the DNA sequence contains deoxyribonucleotides, and further that the RNA sequence will typically contain a uracil at positions where the DNA sequence contains thymidine.

One of skill in the art will appreciate that two polynucleotides of different lengths may be compared over the entire length of the longer fragment. Alternatively, small regions may be compared. Normally sequences of the same length are compared for a final estimation of their utility in the practice of the present invention. It is preferred that there be 100% sequence identity between the dsRNA for use as siRNA and at least 15 contiguous nucleotides of the target gene (e.g., SUR1), although a dsRNA having 70%, 75%, 80%, 85%, 90%, or 95% or greater may also be used in the present invention. A siRNA that is essentially identical to a least a portion of the target gene may also be a dsRNA wherein one of the two complementary strands (or, in the case of a self-complementary RNA, one of the two self-complementary portions) is either identical to the sequence of that portion or the target gene or contains one or more insertions, deletions or single point mutations relative to the nucleotide sequence of that portion of the target gene. siRNA technology thus has the property of being able to tolerate sequence variations that might be expected to result from genetic mutation, strain polymorphism, or evolutionary divergence.

There are several methods for preparing siRNA, such as chemical synthesis, in vitro transcription, siRNA expression vectors, and PCR expression cassettes. Irrespective of which method one uses, the first step in designing an siRNA molecule is to choose the siRNA target site, which can be any site in the target gene. In certain embodiments, one of skill in the art may manually select the target selecting region of the gene, which may be an ORF (open reading frame) as the target selecting region and may preferably be 50-100 nucleotides downstream of the "ATG" start codon. However, there are several readily available programs available to assist with the design of siRNA molecules, for example siRNA Target Designer by Promega, siRNA Target Finder by GenScript Corp., siRNA Retriever Program by Imgenex Corp., EMBOSS siRNA algorithm, siRNA program by Qiagen, Ambion siRNA predictor, Ambion siRNA predictor, Whitehead siRNA prediction, and Sfold. Thus, it is envisioned that any of the above programs may be utilized to produce siRNA molecules that can be used in the present invention.

7. Ribozymes

Ribozymes are RNA-protein complexes that cleave nucleic acids in a site-specific fashion. Ribozymes have specific catalytic domains that possess endonuclease activity (Kim and Cech, 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence specific cleavage/ligation reactions involving nucleic acids (Joyce, 1989; Cech et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression is particularly suited to therapeutic applications (Scanlon et al., 1991; Sarver et al., 1990; Sioud et al., 1992). Most of this work involved the modification of a target mRNA, based on a specific mutant codon that is cleaved by a specific ribozyme. In light of the information included herein and the knowledge of one of ordinary skill in the art, the preparation and use of additional ribozymes that are specifically targeted to a given gene will now be straightforward.

Other suitable ribozymes include sequences from RNase P with RNA cleavage activity (Yuan et al., 1992; Yuan and Altman, 1994), hairpin ribozyme structures (Berzal-Herranz et al., 1992; Chowrira et al., 1993) and hepatitis D virus based ribozymes (Perrotta and Been, 1992). The general design and optimization of ribozyme directed RNA cleavage activity has been discussed in detail (Haseloff and Gerlach, 1988; Symons, 1992; Chowrira, et al., 1994; and Thompson, et al., 1995).

The other variable on ribozyme design is the selection of a cleavage site on a given target RNA. Ribozymes are targeted to a given sequence by virtue of annealing to a site by complimentary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence which is the cleavage site. For hammerhead ribozymes, the cleavage site is a dinucleotide sequence on the target RNA, uracil (U) followed by either an adenine, cytosine or uracil (A, C or U; Perriman, et al., 1992; Thompson, et al., 1995). The frequency of this dinucleotide occurring in any given RNA is statistically 3 out of 16.

Designing and testing ribozymes for efficient cleavage of a target RNA is a process well known to those skilled in the art. Examples of scientific methods for designing and testing ribozymes are described by Chowrira et al. (1994) and Lieber and Strauss (1995), each incorporated by reference. The identification of operative and preferred sequences for use in SUR1 targeted ribozymes is simply a matter of preparing and testing a given sequence, and is a routinely practiced screening method known to those of skill in the art.

8. Inhibition of Post-Translational Assembly and Trafficking

Following expression of individual regulatory and pore-forming subunit proteins of the channel, and in particular aspects of the invention, these proteins are modified by glycosylation in the Golgi apparatus of the cell, assembled into functional heteromultimers that comprise the channel, and then transported to the plasmalemmal membrane where they are inserted to form functional channels. The last of these processes is referred to as "trafficking".

In specific embodiments of the invention, molecules that bind to any of the constituent proteins interfere with post-translational assembly and trafficking, and thereby interfere with expression of functional channels. One such example is with glibenclamide binding to SUR1 subunits. In additional embodiments, glibenclamide, which binds with femtomolar affinity to SUR1, interferes with post-translational assembly and trafficking required for functional channel expression.

B. Cation Channel Blockers

In some embodiments of the present invention, the combinatorial therapeutic composition comprises one or more cation channel blockers (including, for example, $Ca^{2+}$ channel blocker, $K^+$ channel blocker, $Na^+$ channel blocker, and non-specific cation channel blocker). Exemplary blockers include pinokalant (LOE 908 MS); rimonabant (SR141716A); fenamates (flufenamic acid, mefenamic acid, niflumic acid, for example); SKF 96365 (1-(beta-[3-(4-methoxy-phenyl)propoxy]-4-methoxyphenethyl)-1H-imidazole hydrochloride); and/or a combination or mixture thereof.

In certain embodiments a $Ca^{2+}$ channel blocker includes, for example, Amlodipine besylate, (R)-($^+$)-Bay K, Cilnidipine, w-Conotoxin GVIA, w-Conotoxin MVIIC, Diltiazem hydrochloride, Gabapentin, Isradipine, Loperamide hydrochloride, Mibefradil dihydrochloride, Nifedipine, (R)-(−)-Niguldipine hydrochloride, (S)-($^+$)-Niguldipine hydrochloride, Nimodipine, Nitrendipine, NNC 55-0396 dihydrochloride, Ruthenium Red, SKF 96365 hydrochloride, SR 33805 oxalate, Verapamil hydrochloride.

In certain embodiments a $K^+$ channel blocker includes, for example, Apamin, Charybdotoxin, Dequalinium dichloride, Iberiotoxin, Paxilline, UCL 1684, Tertiapin-Q, AM 92016 hydrochloride, Chromanol 293B, (−)-[3R,4S]-Chromanol 293B, CP 339818 hydrochloride, DPO-1, E-4031 dihydrochloride, KN-93, Linopirdine dihydrochloride, XE 991 dihydrochloride, 4-Aminopyridine, DMP 543, YS-035 hydrochloride.

In certain embodiments a $Na^+$ channel blocker includes, for example, Ambroxol hydrochloride, Amiloride hydrochloride, Flecainide acetate, Flunarizine dihydrochloride, Mexiletine hydrochloride, QX 222, QX 314 bromide, QX 314 chloride, Riluzole hydrochloride, Tetrodotoxin, Vinpocetine.

In certain embodiments a non-specific cation channel blocker includes, for example, Lamotrigine, Zonisamide.

In some embodiments of the present invention, the combinatorial therapeutic composition comprises one or more glutamate receptor blockers including, for example, D-AP5, DL-AP5, L-AP5, D-AP7, DL-AP7, (R)-4-Carboxyphenylglycine, CGP 37849, CGP 39551, CGS 19755, (2R,3S)-Chlorpheg, Co 101244 hydrochloride, (R)-CPP, (RS)-CPP, D-CPP-ene, LY 235959, PMPA, PPDA, PPPA, Ro 04-5595 hydrochloride, Ro 25-6981 maleate, SDZ 220-040, SDZ 220-581, (±)-1-(1,2-Diphenylethyl)piperidine maleate, IEM 1460, Loperamide hydrochloride, Memantine hydrochloride, (−)-MK 801 maleate, ($^+$)-MK 801 maleate, N20C hydrochloride, Norketamine hydrochloride, Remacemide hydrochloride, ACBC, CGP 78608 hydrochloride, 7-Chlorokynurenic acid, CNQX, 5,7-Dichlorokynurenic acid, Felbamate, Gavestinel, (S)-(−)-HA-966, L-689,560, L-701,252, L-701,324, Arcaine sulfate, Eliprodil, N-(4-Hydroxyphenylacetyl)spermine, N-(4-Hydroxyphenylpropanoyl) spermine trihydrochloride, Ifenprodil hemitartrate, Synthalin sulfate, CFM-2, GYKI 52466 hydrochloride, IEM 1460, ZK 200775, NS 3763, UBP 296, UBP 301, UBP 302, CNQX, DNQX, Evans Blue tetrasodium salt, NBQX, SYM 2206, UBP 282, ZK 200775]

C. Antagonists of Specific Molecules

Antagonists of specific molecules may be employed, for example, those related to endothelial dysfunction.

1. Antagonists of VEGF

Antagonists of VEGF may be employed. The antagonists may be synthetic or natural, and they may antagonize directly or indirectly. VEGF TrapR1R2 (Regeneron Pharmaceuticals, Inc.); Undersulfated, low-molecular-weight glycol-split heparin (Pisano et al., 2005); soluble NRP-1 (sNRP-1); Avastin (Bevacizumab); HuMV833; s-Flt-1, s-Flk-1; s-Flt-1/Flk-1; NM-3; and/or GFB 116.

2. Antagonists of MMP

Antagonists of any MMP may be employed. The antagonists may be synthetic or natural, and they may antagonize directly or indirectly. Exemplary antagonists of MMPs include at least (2R)-2-[(4-biphenylsulfonyl)amino]-3-phenylproprionic acid (compound 5a), an organic inhibitor of MMP-2/MMP-9 (Nyormoi et al., 2003); broad-spectrum MMP antagonist GM-6001 (Galardy et al., 1994; Graesser et al., 1998); TIMP-1 and/or TIMP-2 (Rolli et al., 2003); hydroxamate-based matrix metalloproteinase inhibitor (RS 132908) (Moore et al., 1999); batimastat (Corbel et al., 2001); those identified in United States Application 20060177448 (which is incorporated by reference herein in its entirety); and/or marimastat (Millar et al., 1998); peptide inhibitors that comprise HWGF (including CTTHWG-FTLC) (Koivunen et al., 1999); and combinations thereof.

3. Antagonists of NOS

Antagonists of NOS may be employed. The antagonists may be synthetic or natural, and they may antagonize directly or indirectly. The antagonists may be antagonists of NOS I, NOS II, NOS III, or may be nonselective NOS antagonists. Exemplary antagonists include at least the following: aminoguanidine (AG); 2-amino-5,6-dihydro-6-methyl-4H-1,3 thiazine (AMT); S-ethylisothiourea (EIT) (Rairigh et al., 1998); asymmetric dimethylarginine (ADMA) (Vallance et al., 1992); N-nitro-L-arginine methylester (L-NAME) (Papapetropoulos et al., 1997; Babaei et al., 1998); nitro-L-arginine (L-NA) (Abman et al., 1990; Abman et al., 1991; Cornfield et al., 1992; Fineman et al., 1994; McQueston et al., 1993; Storme et al., 1999); the exemplary selective NOS II antagonists, aminoguanidine (AG) and N-(3-aminomethyl) benzylacetamidine dihydrochloride (1400 W); NG-monomethyl-L-arginine (L-NMMA); the exemplary selective NOS I antagonist, 7-nitroindazole (7-NINA), and a nonselective NOS antagonist, N-nitro-L-arginine (L-NNA), or a mixture or combination thereof.

4. Antagonists of Thrombin

Antagonists of thrombin may be employed. The antagonists may be synthetic or natural, and they may antagonize directly or indirectly. Exemplary thrombin antagonists include at least the following: ivalirudin (Kleiman et al., 2002); hirudin (Hoffman et al., 2000); SSR182289 (Duplantier et al., 2004); antithrombin III; thrombomodulin; Lepirudin (Refludan, a recombinant therapeutic hirudin); P-PACK II (d-Phenylalanyl-L-Phenylalanylarginine-chloromethyl ketone 2 HCl); Thromstop (BNas-Gly-(pAM)Phe-Pip); Argatroban (Carr et al., 2003); and mixtures or combinations thereof.

5. Antagonist of Tumor Necrosis Factor-α (TNF α) and Nuclear Factor κB (NFκB)

Antagonists of tumor necrosis factor α (TNF α) reduce the expression of $NC_{Ca\text{-}ATP}$ channels, as do antagonists of nuclear factor κB (NFκB). In embodiments of the invention, organs, cells, and/or patients, are treated with compositions including one or more antagonists of TNF α and/or NFκB.

Such treatment may be before an expected or possible ischemic or ischemic/hypoxic incident; may be during an ischemic or ischemic/hypoxic incident; and/or may be following an ischemic or ischemic/hypoxic incident. For example, an organ removed from a patient for later placement in the patient's body (e.g., a blood vessel used in heart bypass surgery) may be treated before, during, and/or after removal from its place of origin, and may be treated before, during, and/or after its placement in its new location. For further example, an organ removed from an organ donor for later transplantation into a different patient's body (e.g., a liver, kidney, lung, or heart used in transplant surgery) may be treated before, during, and/or after removal from the organ donor, and may be treated before, during, and/or after its placement in its new location in the patient receiving the organ.

D. Others

Non-limiting examples of an additional pharmacological therapeutic agent that may be used in the present invention include an antihyperlipoproteinemic agent, an antiarteriosclerotic agent, an anticholesterol agent, an antiinflammatory agent, an antithrombotic/fibrinolytic agent, anticoagulant, antiplatelet, vasodilator, and/or diuretics. Thromboblytics that are used can include, but are not limited to prourokinase, streptokinase, and tissue plasminogen activator (tPA) Anticholesterol agents include but are not limited to HMG-CoA Reductase inhibitors, cholesterol absorption inhibitors, bile acid sequestrants, nicotinic acid and derivatives thereof, fibric acid and derivatives thereof. HMG-CoA Reductase inhibitors include statins, for example, but not limited to atorvastatin calcium (Lipitor®), cerivastatin sodium (Baycol®), fluvastatin sodium (Lescol®), lovastatin (Advicor®), pravastatin sodium (Pravachol®), and simvastatin (Zocor®). Agents known to reduce the absorption of ingested cholesterol include, for example, Zetia®. Bile acid sequestrants include, but are not limited to cholestryramine, cholestipol and colesevalam. Other anticholesterol agents include fibric acids and derivatives thereof (e.g., gemfibrozil, fenofibrate and clofibrate); nicotinic acids and derivatives thereof (e.g., nician, lovastatin) and agents that extend the release of nicotinic acid, for example niaspan. Antiinflammatory agents include, but are not limited to non-sterodial anti-inflammatory agents (e.g., naproxen, ibuprofen, celeoxib) and sterodial anti-inflammatory agents (e.g., glucocorticoids). Anticoagulants include, but are not limited to heparin, warfarin, and coumadin. Antiplatelets include, but are not limited to aspirin, and aspirin related-compounds, for example acetaminophen. Diuretics include, but are not limited to such as furosemide (Lasix), bumetanide (Bumex), torsemide (Demadex), thiazide & thiazide-like diuretics (e.g., chlorothiazide (Diuril) and hydrochlorothiazide (Esidrix), benzthiazide, cyclothiazide, indapamide, chlorthalidone, bendroflumethizide, metolazone), amiloride, triamterene, and spironolacton. Vasodilators include, but are not limited to nitroglycerin.

Thus, in certain embodiments, the present invention comprises co-administration of an antagonist of the $NC_{Ca\text{-}ATP}$ channel with a thrombolytic agent. Co-administration of these two compounds increases the therapeutic window of the thrombolytic agent. Examples of suitable thrombolytic agents that can be employed in the methods and pharmaceutical compositions of this invention are prourokinase, streptokinase, and tissue plasminogen activator (tPA).

In certain embodiments, the present invention comprises co-administration of an antagonist of the $NC_{Ca\text{-}ATP}$ channel with glucose or related carbohydrate to maintain appropriate levels of serum glucose. Appropriate levels of blood glucose are within the range of about 60 mmol/l to about 150 mmol/liter. Thus, glucose or a related carbohydrate is administered in combination to maintain the serum glucose within this range.

To inhibit hemorrhagic conversion, reduce cell swelling, etc., using the methods and compositions of the present invention, one would generally contact a cell with antagonist of $NC_{Ca\text{-}ATP}$ channel or related-compounds thereof in combination with an additional therapeutic agent, such as tPA, aspirin, statins, diuretics, warfarin, coumadin, mannitol, etc. These compositions would be provided in a combined amount effective to inhibit hemorrhagic conversion, cell swelling and edema. This process may involve contacting the cells with agonist of $NC_{Ca\text{-}ATP}$ channel or related-compounds thereof in combination with an additional therapeutic agent or factor(s) at the same time. This may be achieved by contacting the cell with a single composition or pharmacological formulation that includes both agents, or by contacting the cell with two distinct compositions or formulations, at the same time, wherein one composition includes an antagonist of the $NC_{Ca\text{-}ATP}$ channel or derivatives thereof and the other includes the additional agent.

Further embodiments include treatment with SUR1 antagonist, thrombolytic agent, and glucose. Glucose administration may be at the time of treatment with SUR1 antagonist, or may follow treatment with SUR1 antagonist (e.g., at 15 minutes after treatment with SUR1 antagonist, or at one half hour after treatment with SUR1 antagonist, or at one hour after treatment with SUR1 antagonist, or at two hours after treatment with SUR1 antagonist, or at three hours after treatment with SUR1 antagonist). Glucose administration may be by intravenous, or intraperitoneal, or other suitable route and means of delivery. Additional glucose allows administration of higher doses of SUR1 antagonist than might otherwise be possible. Treatment with glucose in conjunction with treatment with SUR1 antagonist (at the same time as treatment with SUR1 antagonist, or at a later time after treatment with SUR1 antagonist) may further enlarge the time window after stroke, trauma, or other brain injury when thrombolytic treatment may be initiated.

Yet further, the combination of the antagonist and tPA results in a decrease or prevention of hemorrhagic conversion following reperfusion. Hemorrhagic conversion is the transformation of a bland infarct into a hemorrhagic infarct after restoration of circulation. It is generally accepted that these complications of stroke and of reperfusion are attributable to capillary endothelial cell dysfunction that worsens as ischemia progresses. Thus, the present invention is protective of the endothelial cell dysfunction that occurs as a result of an ischemic event.

XIII. Exemplary Pharmaceutical Formulations and Methods of Use

A. Exemplary Compositions of the Present Invention

The present invention also contemplates therapeutic methods employing compositions comprising the active substances disclosed herein. Preferably, these compositions include pharmaceutical compositions comprising a therapeutically effective amount of one or more of the active compounds or substances along with a pharmaceutically acceptable carrier.

As used herein, the term "pharmaceutically acceptable" carrier means a non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations.

Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Examples of pharmaceutically acceptable antioxidants include, but are not limited to, water soluble antioxidants such as ascorbic acid, cysteine hydrochloride, sodium bisulfite, sodium metabisulfite, sodium sulfite, and the like; oil soluble antioxidants, such as ascorbyl palmitate, butylated hydroxyanisole (BHA), butylated hydroxytoluene (BHT), lecithin, propyl gallate, aloha-tocopherol and the like; and the metal chelating agents such as citric acid, ethylenediamine tetraacetic acid (EDTA), sorbitol, tartaric acid, phosphoric acid and the like.

B. Dose Determinations

By a "therapeutically effective amount" or simply "effective amount" of an active compound, such as glibenclamide or tolbutamide, is meant a sufficient amount of the compound to treat or alleviate the brain swelling at a reasonable benefit/risk ratio applicable to any medical treatment. It will be understood, however, that the total daily usage of the active compounds and compositions of the present invention will be decided by the attending physician within the scope of sound medical judgment. The specific therapeutically effective dose level for any particular patient will depend upon a variety of factors including the disorder being treated and the severity of the brain injury or ischemia; activity of the specific compound employed; the specific composition employed; the age, body weight, general health, sex and diet of the patient; the time of administration, route of administration, and rate of excretion of the specific compound employed; the duration of the treatment; drugs used in combination or coinciding with the specific compound employed; and like factors well known in the medical arts.

Toxicity and therapeutic efficacy of such compounds can be determined by standard pharmaceutical procedures in cell assays or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell based assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The total daily dose of the active compounds of the present invention administered to a subject in single or in divided doses can be in amounts, for example, from 0.01 to 25 mg/kg body weight or more usually from 0.1 to 15 mg/kg body weight. Single dose compositions may contain such amounts or submultiples thereof to make up the daily dose. In general, treatment regimens according to the present invention comprise administration to a human or other mammal in need of such treatment from about 1 mg to about 1000 mg of the active substance(s) of this invention per day in multiple doses or in a single dose of from 1 mg, 5 mg, 10 mg, 100 mg, 500 mg or 1000 mg.

In certain situations, it may be important to maintain a fairly high dose of the active agent in the blood stream of the patient, particularly early in the treatment. Such a fairly high dose may include a dose that is several times greater than its use in other indications. For example, the typical anti-diabetic dose of oral or IV glibenclamide is about 2.5 mg/kg to about 15 mg/kg per day; the typical anti-diabetic dose of oral or IV tolbutamide is about to 0.5 gm/kg to about 2.0 gm/kg per day; the typical anti-diabetic dose for oral gliclazide is about 30 mg/kg to about 120 mg/kg per day; however, much larger doses may be required to block neural cell swelling and brain swelling.

For example, in one embodiment of the present invention directed to a method of preventing neuronal cell swelling in the brain of a subject by administering to the subject a formulation containing an effective amount of a compound that blocks the $NC_{Ca-ATP}$ channel and a pharmaceutically acceptable carrier; such formulations may contain from about 0.1 to about 100 grams of tolbutamide or from about 0.5 to about 150 milligrams of glibenclamide. In another embodiment of the present invention directed to a method of alleviating the negative effects of traumatic brain injury or cerebral ischemia stemming from neural cell swelling in a subject by administering to the subject a formulation containing an effective amount of a compound that blocks the $NC_{Ca-ATP}$ channel and a pharmaceutically acceptable carrier.

In situations of traumatic brain injury or cerebral ischemia (such as stroke), or cerebral hypoxia, it may be important to maintain a fairly high dose of the active agent to ensure delivery to the brain of the patient, particularly early in the treatment. Hence, at least initially, it may be important to keep the dose relatively high and/or at a substantially constant level for a given period of time, preferably, at least about six or more hours, more preferably, at least about twelve or more hours and, most preferably, at least about twenty-four or more hours. In situations of traumatic brain injury or cerebral ischemia (such as stroke), it may be important to maintain a fairly high dose of the active agent to ensure delivery to the brain of the patient, particularly early in the treatment.

When the method of the present invention is employed to treat conditions involving bleeding in the brain, such as traumatic brain injury or cerebral ischemia (such as stroke), delivery via the vascular system is available and the compound is not necessarily required to readily cross the blood-brain barrier.

C. Formulations and Administration

The compounds of the present invention may be administered alone or in combination or in concurrent therapy with other agents which affect the central or peripheral nervous system, particularly selected areas of the brain.

Liquid dosage forms for oral administration may include pharmaceutically acceptable emulsions, microemulsions, solutions, suspensions, syrups and elixirs containing inert diluents commonly used in the art, such as water, isotonic solutions, or saline. Such compositions may also comprise adjuvants, such as wetting agents; emulsifying and suspending agents; sweetening, flavoring and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulation can be sterilized, for example, by filtration through a bacteria-retaining filter, or by incorporating sterilizing agents in the form of sterile solid compositions, which can be dissolved or dispersed in sterile water or other sterile injectable medium just prior to use.

In order to prolong the effect of a drug, it is often desirable to slow the absorption of a drug from subcutaneous or intramuscular injection. The most common way to accomplish this is to inject a suspension of crystalline or amorphous material with poor water solubility. The rate of absorption of the drug becomes dependent on the rate of dissolution of the drug, which is, in turn, dependent on the physical state of the drug, for example, the crystal size and the crystalline form. Another approach to delaying absorption of a drug is to administer the drug as a solution or suspension in oil. Injectable depot forms can also be made by forming microcapsule matrices of drugs and biodegradable polymers, such as polylactide-polyglycoside. Depending on the ratio of drug to polymer and the composition of the polymer, the rate of drug release can be controlled. Examples of other biodegradable polymers include polyorthoesters and polyanhydrides. The depot injectables can also be made by entrapping the drug in liposomes or microemulsions, which are compatible with body tissues.

Suppositories for rectal administration of the drug can be prepared by mixing the drug with a suitable non-irritating excipient, such as cocoa butter and polyethylene glycol which are solid at ordinary temperature but liquid at the rectal temperature and will, therefore, melt in the rectum and release the drug.

Solid dosage forms for oral administration may include capsules, tablets, pills, powders, gelcaps and granules. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents. Tablets and pills can additionally be prepared with enteric coatings and other release-controlling coatings.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferably, in a certain part of the intestinal tract, optionally in a delayed manner. Examples of embedding compositions which can be used include polymeric substances and waxes.

Dosage forms for topical or transdermal administration of a compound of this invention further include ointments, pastes, creams, lotions, gels, powders, solutions, sprays, inhalants or patches. Transdermal patches have the added advantage of providing controlled delivery of active compound to the body. Such dosage forms can be made by dissolving or dispersing the compound in the proper medium. Absorption enhancers can also be used to increase the flux of the compound across the skin. The rate can be controlled by either providing a rate controlling membrane or by dispersing the compound in a polymer matrix or gel. The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

The method of the present invention employs the compounds identified herein for both in vitro and in vivo applications. For in vivo applications, the invention compounds can be incorporated into a pharmaceutically acceptable formulation for administration. Those of skill in the art can readily determine suitable dosage levels when the invention compounds are so used.

As employed herein, the phrase "suitable dosage levels" refers to levels of compound sufficient to provide circulating concentrations high enough to effectively block the $NC_{Ca\text{-}ATP}$ channel and prevent or reduce neural cell swelling in vivo.

In accordance with a particular embodiment of the present invention, compositions comprising at least one SUR1 antagonist compound (as described above), and a pharmaceutically acceptable carrier are contemplated.

Exemplary pharmaceutically acceptable carriers include carriers suitable for oral, intravenous, subcutaneous, intramuscular, intracutaneous, and the like administration. Administration in the form of creams, lotions, tablets, dispersible powders, granules, syrups, elixirs, sterile aqueous or non-aqueous solutions, suspensions or emulsions, and the like, is contemplated.

For the preparation of oral liquids, suitable carriers include emulsions, solutions, suspensions, syrups, and the like, optionally containing additives such as wetting agents, emulsifying and suspending agents, sweetening, flavoring and perfuming agents, and the like.

For the preparation of fluids for parenteral administration, suitable carriers include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized, for example, by filtration through a bacteria-retaining filter, by incorporating sterilizing agents into the compositions, by irradiating the compositions, or by heating the compositions. They can also be manufactured in the form of sterile water, or some other sterile injectable medium immediately before use. The active compound is admixed under sterile conditions with a pharmaceutically acceptable carrier and any needed preservatives or buffers as may be required.

The treatments may include various "unit doses." Unit dose is defined as containing a predetermined quantity of the therapeutic composition (an antagonist of the $NC_{Ca\text{-}ATP}$ channel or its related-compounds thereof) calculated to produce the desired responses in association with its administration, e.g., the appropriate route and treatment regimen. The quantity to be administered, and the particular route and formulation, are within the skill of those in the clinical arts. Also of import is the subject to be treated, in particular, the state of the subject and the protection desired. A unit dose need not be administered as a single injection but may comprise continuous infusion over a set period of time.

D. Formulations and Routes for Administration of Compounds

Pharmaceutical compositions of the present invention comprise an effective amount of one or more modulators of $NC_{Ca\text{-}ATP}$ channel (antagonist and/or agonist) or related compounds or additional agent) dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one modulators of $NC_{Ca\text{-}ATP}$ channel (antagonist and/or agonist) or related compounds or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The modulators of $NC_{Ca\text{-}ATP}$ channel (antagonist and/or agonist) or related compounds may comprise different types of carriers depending on whether it is to be administered in solid, liquid or aerosol form, and whether it need to be sterile for such routes of administration as injection. The present invention can be administered intravenously, intradermally, transdermally, intrathecally, intraventricularly, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The modulators of $NC_{Ca\text{-}ATP}$ channel (antagonist and/or agonist) or related compounds may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semisolid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include the modulators of $NC_{Ca\text{-}ATP}$ channel (antagonist and/or agonist) or related compounds, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the modulators of $NC_{Ca\text{-}ATP}$ channel (antagonist and/or agonist) or related compounds may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic and/or prophylactic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

Pharmaceutical formulations may be administered by any suitable route or means, including alimentary, parenteral, topical, mucosal or other route or means of administration. Alimentary routes of administration include administration oral, buccal, rectal and sublingual routes. Parenteral routes of administration include administration include injection into the brain parenchyma, and intravenous, intradermal, intramuscular, intraarterial, intrathecal, subcutaneous, intraperitoneal, and intraventricular routes of administration. Topical routes of administration include transdermal administration.

E. Alimentary Compositions and Formulations

In preferred embodiments of the present invention, the modulators of $NC_{Ca-ATP}$ channel (antagonist and/or agonist) or related compounds are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792, 451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations that are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

F. Parenteral Compositions and Formulations

In further embodiments, the modulators of $NC_{Ca-ATP}$ channel (antagonist and/or agonist) or related compounds may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intraventricularly, intrathecally, subcutaneous, or intraperitoneally U.S. Pat. Nos. 6,7537,514; 6,613, 308; 5,466,468; 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, DMSO, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

G. Miscellaneous Pharmaceutical Compositions and Formulations

In other preferred embodiments of the invention, the active compound modulators of $NC_{Ca-ATP}$ channel (antagonist and/or agonist) or related compounds may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

XIV. Combination Treatments

In the context of the present invention, it is contemplated that an antagonist of the $NC_{Ca-ATP}$ channel or related-compounds thereof is used in combination with an additional therapeutic agent to more effectively treat any disease or medical condition in an individual in need thereof, such as a cerebral ischemic event, and/or decrease intracranial pressure, for example. In some embodiments, it is contemplated that a conventional therapy or agent, including but not limited to, a pharmacological therapeutic agent may be combined with the antagonist or related-compound of the present invention. The combined therapeutic agents may work synergistically, although in alternative embodiments they work additively.

Pharmacological therapeutic agents and methods of administration, dosages, etc. are well known to those of skill in the art (see for example, the "Physicians Desk Reference", Goodman & Gilman's "The Pharmacological Basis of Therapeutics", "Remington's Pharmaceutical Sciences", and "The Merck Index, Eleventh Edition", incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject, and such individual determinations are within the skill of those of ordinary skill in the art.

When an additional therapeutic agent is employed, as long as the dose of the additional therapeutic agent does not exceed previously quoted toxicity levels, the effective amounts of the additional therapeutic agent may simply be defined as that amount effective to improve at least one symptom in an animal when administered to an animal in combination with an antagonist of $NC_{Ca-ATP}$ channel or related-compounds thereof. This may be easily determined by monitoring the animal or patient and measuring those physical and biochemical parameters of health and disease that are indicative of the success of a given treatment. Such methods are routine in animal testing and clinical practice.

Treatment with an antagonist of $NC_{Ca\text{-}ATP}$ channel or related-compounds thereof may precede or follow the additional agent treatment by intervals ranging from minutes to hours to weeks to months. In some embodiments, the antagonist of the $NC_{Ca\text{-}ATP}$ channel is administered prior to the additional therapeutic compound, and in other embodiments, the antagonist of the $NC_{Ca\text{-}ATP}$ channel is administered subsequent to the additional therapeutic compound. The difference in time between onset of administration of either part of the combinatorial composition may be within seconds, such as about 60 or less, within minutes, such as about 60 or less, within hours, such as about 24 or less, within days, such as about 7 or less, or within weeks of each other.

In embodiments where the additional agent is applied separately to the cell, one would generally ensure that a significant period of time did not expire between the time of each delivery, such that the agent would still be able to exert an advantageously combined effect on the cell. In such instances, it is contemplated that one would contact the cell with both modalities within about 1-24 hr of each other and, more preferably, within about 6-12 hr of each other.

Typically, for maximum benefit of the additional agent, the therapy must be started within three hours of the onset of stroke symptoms, making rapid diagnosis and differentiation of stroke and stroke type critical. However, in the present invention, administration of the $NC_{Ca\text{-}ATP}$ channel with an additional agent increases this therapeutic window. The therapeutic window for thrombolytic agents, for example, may be increased by several (4-8) hours by co-administering antagonist of the $NC_{Ca\text{-}ATP}$ channel.

In other aspects of the invention, an individual is administered a therapy for organ transplantation, wherein the individual is the donor, the recipient, or both. The additional compound may be referred to as an organ transplant therapeutic compound (which may also be referred to as an agent). Any suitable compound or compounds may be included, although in specific embodiments the compound is one or more of an immunsuppressant; antiviral like acyclovir (Zovirax), or valganciclovir (Valcyte) to fight viruses; antifungal like fluconazole (Diflucan), nystatin (Mycostatin, Nilstat), or itraconazole (Sporanox) to fight fungal infection; antibiotic such as sulfamethoxazole/trimethoprim (Bactrim, Septra) to help fight bacterial infection; or a combination or mixture thereof. Exemplary immunosuppressants include tacrolimus (Prograf), mycophenolate mofetil (CellCept), sirolimus (Rapamune), prednisone, cyclosoporine (Neoral, Sandimmune, Gengraf) and azathioprine (Imuran), for example. The additional therapy may be delivered to an individual prior to delivery of the therapy of the invention, during delivery of the therapy of the invention, or both.

XV. Diagnostics

The antagonist or related compound can be used for diagnosing, monitoring, or prognosticating of an ischemic episode in an organ and/or tissue. In particular, an organ may be assayed for being suitable for transplantation by identifying whether or not the channel is present. If the channel is identified in one or more cells of the tissue or organ, then the respective tissue or organ may be subjected to a compound of the invention or may be considered unsuitable for transplantation.

A. Genetic Diagnosis

One embodiment of the instant invention comprises a method for detecting expression of any portion of a $Na_{Ca\text{-}ATP}$ channel in the organ or tissue. For example, expression of the regulatory unit, SUR1, and/or expression of the pore-forming subunit may be assayed. This may comprise determining the level of SUR1 expressed and/or the level of the pore-forming subunit expressed. It is understood by the present invention that the up-regulation or increased expression of the $Na_{Ca\text{-}ATP}$ channel relates to increased levels of SUR1, which correlates to ischemic episode, in specific embodiments.

First, a biological sample is obtained from a subject. The biological sample may be tissue or fluid, for example. In certain embodiments, the biological sample includes cells from an organ or tissue to be transplanted.

Nucleic acids used are isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA (cDNA). In one embodiment, the RNA is whole cell RNA; in another, it is poly-A RNA. Normally, the nucleic acid is amplified.

Depending on the format, the specific nucleic acid of interest is identified in the sample directly using amplification or with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994).

Following detection, one may compare the results seen in a given subject with a statistically significant reference group of normal subjects and subjects that have been diagnosed with an ischemic episode.

Yet further, it is contemplated that chip-based DNA technologies such as those described by Hacia et al., (1996) and Shoemaker et al., (1996) can be used for diagnosis. Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization. See also Pease et al., (1994); Fodor et al., (1991).

B. Other Types of Diagnosis

In specific embodiments, the presence of the $NC_{Ca\text{-}ATP}$ channel is identified in a tissue or organ by employing patch clamp analysis on at least one cell from the respective tissue or organ.

In other embodiments, in order to increase the efficacy of molecules, for example, compounds and/or proteins and/or antibodies, as diagnostic agents, it is conventional to link or covalently bind or complex at least one desired molecule or moiety.

Certain examples of conjugates are those conjugates in which the molecule (for example, protein, antibody, and/or compound) is linked to a detectable label. "Detectable labels" are compounds and/or elements that can be detected due to their specific functional properties, and/or chemical characteristics, the use of which allows the antibody to which they are attached to be detected, and/or further quantified if desired.

Conjugates are generally preferred for use as diagnostic agents. Diagnostics generally fall within two classes, those for use in in vitro diagnostics, such as in a variety of immunoassays, and/or those for use in vivo diagnostic protocols, generally known as "molecule-directed imaging".

Many appropriate imaging agents are known in the art, as are methods for their attachment to molecules, for example, antibodies (see, for e.g., U.S. Pat. Nos. 5,021,236; 4,938, 948; and 4,472,509, each incorporated herein by reference). The imaging moieties used can be paramagnetic ions; radioactive isotopes; fluorochromes; NMR-detectable substances; X-ray imaging.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention $^{211}$astatine, $^{11}$carbon, $^{14}$carbon, $^{51}$chromium, $^{36}$chlorine, $^{57}$cobalt, $^{58}$cobalt, $^{67}$copper, $^{152}$Eu, $^{67}$gallium, $^{3}$hydrogen, $^{123}$iodine, $^{125}$iodine, $^{13}$iodine, $^{111}$indium, $^{59}$iron, $^{32}$phosphorus, $^{186}$rhenium, $^{188}$rhenium, $^{75}$selenium, $^{35}$sulphur, $^{99m}$ technicium and/or $^{90}$yttrium. $^{125}$I is often being preferred for use in certain embodiments, and $^{99m}$ technicium and/or $^{111}$indium are also often preferred due to their low energy and suitability for long range detection.

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of conjugates contemplated in the present invention are those intended primarily for use in vitro, where the molecule is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and/or avidin and streptavidin compounds. The use of such labels is well known to those of skill in the art and are described, for example, in U.S. Pat. Nos. 3,817,837; 3,850,752; 3,939, 350; 3,996,345; 4,277,437; 4,275,149 and 4,366,241; each incorporated herein by reference.

The steps of various other useful immunodetection methods have been described in the scientific literature, such as, e.g., Nakamura et al., (1987). Immunoassays, in their most simple and direct sense, are binding assays. Certain preferred immunoassays are the various types of radioimmunoassays (RIA) and immunobead capture assay. Immunohistochemical detection using tissue sections also is particularly useful. However, it will be readily appreciated that detection is not limited to such techniques, and Western blotting, dot blotting, FACS analyses, and the like also may be used in connection with the present invention.

Immunologically-based detection methods for use in conjunction with Western blotting include enzymatically-, radiolabel-, or fluorescently-tagged secondary molecules/ antibodies against the SUR1 or regulatory subunit of the $NC_{Ca-ATP}$ channel are considered to be of particular use in this regard. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

In addition to the above imaging techniques, one of skill in the art is also aware that positron emission tomography, PET imaging or a PET scan, can also be used as a diagnostic examination. PET scans involve the acquisition of physiologic images based on the detection of radiation from the emission of positrons. Positrons are tiny particles emitted from a radioactive substance administered to the subject.

Thus, in certain embodiments of the present invention, the antagonist or related-compound thereof is enzymatically-, radiolabel-, or fluorescently-tagged, as described above and used to diagnose or monitor an ischemic episode in an organ.

XVI. Therapeutic and/or Diagnostic Kits of the Invention

Any of the compositions described herein may be comprised in a kit. In a specific embodiment, a combinatorial therapeutic composition is provided in a kit, and in some embodiments the two or more compounds that make up the composition are housed separately or as a mixture. Antagonists of the channel that may be provided include but are not limited to antibodies (monoclonal or polyclonal), SUR1 oligonucleotides, SUR1 polypeptides, small molecules or combinations thereof, antagonist, agonist, etc.

In a non-limiting example, the kit comprises an inhibitor of $NC_{Ca-ATP}$ channel that is regulated by SUR1. The inhibitors may be sulfonylurea compounds, such as glibenclamide, tolbutamide, glyburide (1[p-2[5-chloro-O-anisamido)ethyl] phenyl] sulfonyl]-3-cyclohexyl-3-urea); chlopropamide (1-[[(p-chlorophenyl)sulfonyl]-3-propylurea; glipizide (1-cyclohexyl-3[[p-[2(5-methylpyrazine carboxamido)ethyl] phenyl] sulfonyl] urea); or tolazamide(benzenesulfonamide-N-[[(hexahydro-1H-azepin-1yl)amino] carbonyl]-4-methyl). In additional embodiments, non-sulfonyl urea compounds, such as 2, 3-butanedione and 5-hydroxydecanoic acid, quinine, and therapeutically equivalent salts and derivatives thereof, may be employed in the invention.

In other embodiments, an additional compound that is useful for organ removal and/or transplantation is in the kit, and the additional compound may be referred to as an organ transplant therapeutic compound. Any suitable compound or compounds may be included, although in specific embodiments the compound is one or more of an immunsuppressant; antiviral like acyclovir (Zovirax), or valganciclovir (Valcyte) to fight virus; antifungal like fluconazole (Diflucan), nystatin (Mycostatin, Nilstat), or itraconazole (Sporanox) to fight fungal infection; antibiotic such as sulfamethoxazole/trimethoprim (Bactrim, Septra) to help fight bacterial infection; or a combination or mixture thereof. Exemplary immunosuppressants include tacrolimus (Prograf), mycophenolate mofetil (CellCept), sirolimus (Rapamune), prednisone, cyclosoporine (Neoral, Sandimmune, Gengraf) and azathioprine (Imuran), for example.

In additional embodiments, an apparatus useful for transplantation of an organ may be provided in the kit. One of skill in the art recognizes that an apparatus useful for transplantation of the organ includes an apparatus for extraction of the organ from a donor, implantation of the organ in a recipient, or both. Such an apparatus may include one or more of a scalpel, needle, thread, suture, staple, and so forth, for example.

In other embodiments of the invention, the kit comprises one or more apparatuses to obtain a sample from an individual, such as a sample from an organ. The sample may be of any suitable kind, but in particular embodiments the sample is a biopsy from an organ, wherein the biopsy comprise one or more cells. Such an apparatus in the kit may be one or more of a swab, such as a cotton swab, needle toothpick, scalpel, spatula, syringe, and so forth, for example.

In some embodiments, sulfonylurea compounds may be packaged either in aqueous media or in lyophilized form. The container means of the kits will generally include at least one vial, test tube, flask, bottle, syringe or other container means, into which a component may be placed, and preferably, suitably aliquoted. Where there are more than one components in the kit, the kit also may generally contain a second, third, or other additional container into which additional components may be separately placed. The kit may comprise an SUR1 agonist or related compound thereof to open the $NC_{Ca\text{-}ATP}$ channel. Such kits will generally contain, in suitable container means, a pharmaceutically acceptable formulation of SUR1 antagonist, agonist or related compound thereof.

Any of the compositions described herein may be comprised in a kit. In a non-limiting example, it is envisioned that a compound that selectively binds to or identifies SUR1 may be comprised in a diagnostic kit. Such compounds can be referred to as an "SUR1 marker", which may include, but are not limited to antibodies (monoclonal or polyclonal), SUR1 oligonucleotides, SUR1 polypeptides, small molecule or combinations thereof, antagonist, agonist, etc. It is envisioned that any of these SUR1 markers may be linked to a radioactive substance and/or a fluorescent marker and/or a enzymatic tag for quick determination. The kits may also comprise, in suitable container means a lipid, and/or an additional agent, for example a radioactive or enzymatic or florescent marker.

The kits may comprise a suitably aliquoted SUR1 marker, lipid and/or additional agent compositions of the present invention, whether labeled or unlabeled, as may be used to prepare a standard curve for a detection assay. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the SUR1 marker, lipid, additional agent, and any other reagent containers in close confinement for commercial sale. Such containers may include injection or blow molded plastic containers into which the desired vials are retained.

Therapeutic kits of the present invention are kits comprising an antagonist, agonist or an related-compound thereof. Depending upon the condition and/or disease that is being treated, the kit may comprise an SUR1 antagonist or related-compound thereof to block and/or inhibit the $NC_{Ca\text{-}ATP}$ channel. Such kits will generally contain, in suitable container means, a pharmaceutically acceptable formulation of SUR1 antagonist or related compound thereof. The kit may have a single container means, and/or it may have distinct container means for each compound. For example, the therapeutic compound and solution may be contained within the same container; alternatively, the therapeutic compound and solution may each be contained within different containers. A kit may include a container with the therapeutic compound that is contained within a container of solution.

When the components of the kit are provided in one and/or more liquid solutions, the liquid solution is an aqueous solution, with a sterile aqueous solution being particularly preferred. The SUR1 antagonist, agonist or related-compounds thereof may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

Examples of aqueous solutions include, but are not limited to ethanol, DMSO and/or Ringer's solution. In certain embodiments, the concentration of DMSO or ethanol that is used is no greater than 0.1% or (1 ml/1000 mL).

However, the components of the kit may be provided as dried powder(s). When reagents and/or components are provided as a dry powder, the powder can be reconstituted by the addition of a suitable solvent. It is envisioned that the solvent may also be provided in another container means.

The container means will generally include at least one vial, test tube, flask, bottle, syringe and/or other container means, into which the SUR1 antagonist, agonist or related-compounds thereof is suitably allocated. The kits may also comprise a second container means for containing a sterile, pharmaceutically acceptable buffer and/or other diluent.

The kits of the present invention will also typically include a means for containing the vials in close confinement for commercial sale, such as, e.g., injection and/or blow-molded plastic containers into which the desired vials are retained.

Irrespective of the number and/or type of containers, the kits of the invention may also comprise, and/or be packaged with, an instrument for assisting with the injection/administration and/or placement of the SUR1 antagonist, agonist or related-compounds thereof within the body of an animal. Such an instrument may be a syringe, pipette, forceps, and/or any such medically approved delivery vehicle.

In addition to the SUR1 antagonist or related compounds thereof, the kits may also include a second active ingredient. Examples of the second active ingredient include substances to prevent hypoglycemia (e.g., glucose, D5W, glucagon, etc.), thrombolytic agents, anticoagulants, antiplatelets, statins, diuretics, vasodilators, etc. These second active ingredients may be combined in the same vial as the SUR1 antagonist, agonist or related-compounds thereof or they may be contained in a separate vial.

Still further, the kits of the present invention can also include glucose testing kits. Thus, the blood glucose of the patient is measured using the glucose testing kit, then the SUR1 antagonist, agonist or related-compounds thereof can be administered to the subject followed by measuring the blood glucose of the patient.

In addition to the above kits, the therapeutic kits of the present invention can be assembled such that an IV bag comprises a septum or chamber that can be opened or broken to release the compound into the IV bag. Another type of kit may include a bolus kit in which the bolus kit comprises a pre-loaded syringe or similar easy to use, rapidly administrable device. An infusion kit may comprise the vials or ampoules and an IV solution (e.g., Ringer's solution) for the vials or ampoules to be added prior to infusion. The infusion kit may also comprise a bolus kit for a bolus/loading dose to be administered to the subject prior, during or after the infusion.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

$NC_{Ca\text{-}ATP}$ Channel—its Identification and Role in Cytotoxic and Ionic Edema The original discovery of the $NC_{Ca\text{-}ATP}$ channel involved reactive astrocytes from the hypoxic inner zone of the gliotic capsule in brain (Chen and Simard, 2001; Chen et al., 2003). Since then, this channel was also identified in neurons from the ischemic core following middle cerebral artery occlusion (FIGS. 1A-1D) (Simard et al., 2006). This channel is permeable to all inorganic and some organic monovalent cations, it requires intracellular $Ca^{2+}$ for activation, and opening is triggered by depletion of intracellular ATP (Chen and Simard, 2001). A critical feature of the $NC_{Ca\text{-}ATP}$ channel is that it is regulated by sulfonylurea receptor type 1 (SUR1) (Chen et al., 2003), just like the $K_{ATP}$ channel in pancreatic β cells. Thus, it is blocked by sulfonylurea compounds (glibenclamide), non-sulfonylurea compounds (repaglinide), and is opened by SUR1-activators (a.k.a., $K^+$-channel openers-diazoxide). Although the $NC_{Ca\text{-}ATP}$ channel has regulatory features in common with the $K_{ATP}$ channel, the fact that it allows passage of all inorganic monovalent cations indicates that its pore-forming subunit(s) are very different from Kir6.x, the pore-forming subunits of $K_{ATP}$ channels.

The $NC_{Ca\text{-}ATP}$ channel is blocked by nanomolar concentrations of glibenclamide. Notably, because glibenclamide is a weak acid (pKa, 6.3), the potency of block is increased at the low pH typical of ischemic or injured tissues (FIGS. 1A-1D).

Figure 2B:
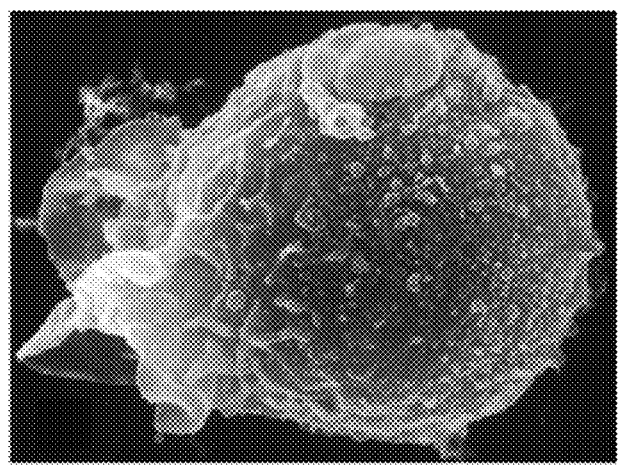
Figure 2A:
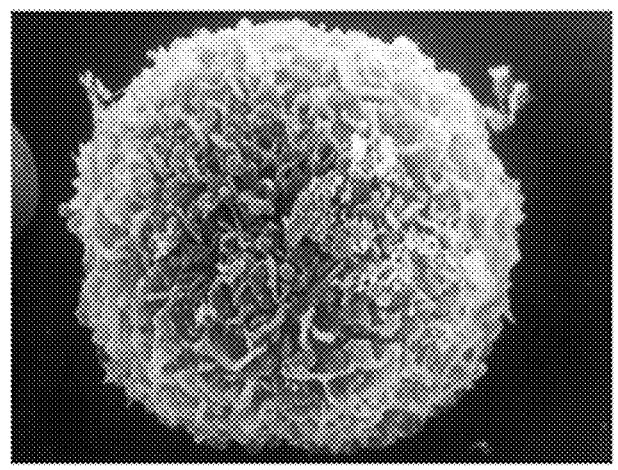
Figure 3:
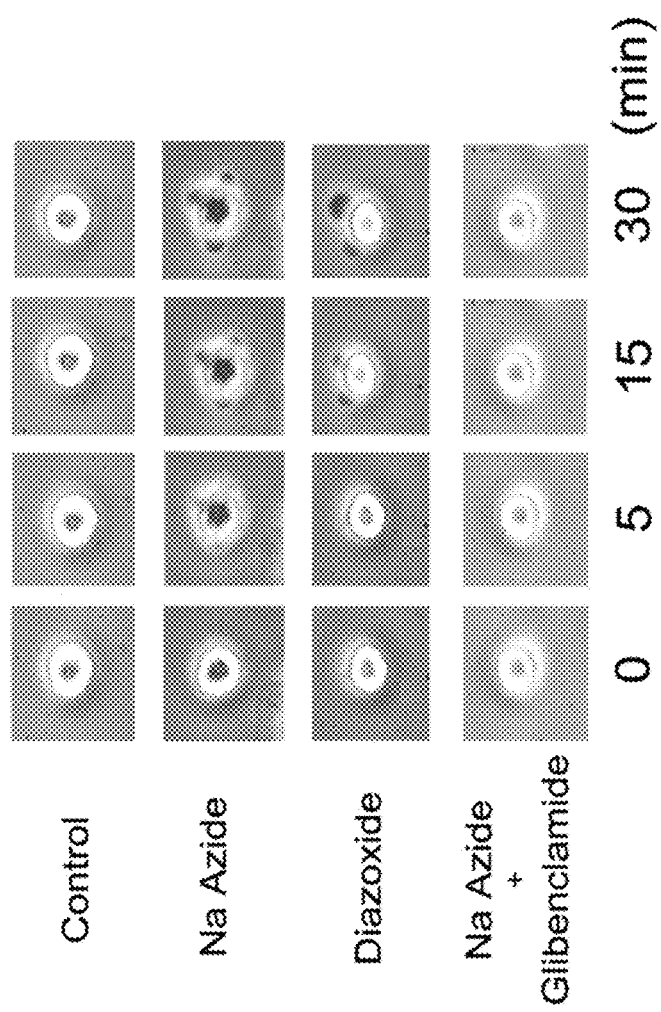
FIG. 3 shows phase contrast micrographs showing appearance of freshly isolated reactive astrocytes under control conditions, and cell blebbing after exposure to 1 mM Na azide. Blebbing was reproduced by diazoxide alone, which opens the $NC_{Ca-ATP}$ channel, whereas Na-azide induced blebbing was blocked by glibenclamide (also referred to as glyburide), which inhibits channel opening; separate labeling showed that cells were GFAP-positive astrocytes. (PMID 13679426)

The $NC_{Ca\text{-}ATP}$ channel is opened by depleting intracellular ATP, which can be simulated in vitro by exposure to Na azide (FIGS. 2A-2C). Opening the channel causes influx of $Na^+$, which rapidly depolarizes the cell, creating an osmotic gradient that draws in water and results in cell blebbing and swelling (cytotoxic edema) (FIGS. 2A-2C) (Chen and Simard, 2001). Notably, blebbing is reproduced in the absence of ATP depletion by opening the channel with diazoxide (FIG. 3). Conversely, cell blebbing observed with Na azide-induced ATP depletion is completely prevented by glibenclamide (FIG. 3).

Blebbing and cytotoxic edema foreshadow necrotic cell death. Freshly isolated reactive astrocytes were labeled with propidium iodide (PI), a marker of necrotic death, and for annexin V, a marker of apoptotic death. Cells exposed to Na azide showed a marked increase in necrotic but not apoptotic death (FIGS. 4A-4C). However, when glibenclamide was present, Na azide-induced necrotic cell death was significantly reduced (FIGS. 4A-4C). These in vitro data show the important role of the $NC_{Ca\text{-}ATP}$ channel in necrotic cell death, and suggest that glibenclamide may be useful in preventing cytotoxic edema and necrotic death in vivo.

The effect of block of $NC_{Ca\text{-}ATP}$ channels by glibenclamide was studied in rodent models of stroke (Simard et al., 2006). In control rats, 7-day mortality after large MCA stroke associated with malignant cerebral edema was 68%, whereas in glibenclamide-treated rats, 7-day mortality was reduced to 28% (n=29 in each group; p<0.001, by +2). In separate groups of rats, ionic edema (excess water) was found as well as stroke size were reduced by half with glibenclamide treatment, confirming an important role of the $NC_{Ca\text{-}ATP}$ channel in the pathophysiology of stroke (Simard et al., 2006).

Example 2

Rodent Model of Cervical SCI

The cervical contusion SCI model that is used is that of Soblosky et al. (2001). Adult female Long-Evans rats are anesthetized (Ketamine and Xylazine) and a hemilaminectomy is made at C4-5 to expose the dura. A hemi-cervical spinal cord contusion is created using a blunt force impactor (see details below "The model of contusion SCI"). This model of SCI is appealing because it yields a gradable lesion, it spares part of the opposite hemi-cord, favoring retention of key neurological functions such as micturition, and it disrupts ipsilateral fine forepaw neurological function, which is more sensitive to injury/recovery than cruder hindpaw/hindlimb function. Most importantly, the cervical location of the injury is ideal for modeling the typical human injury.

To generate the injury for the data shown here, the impactor was activated using a 10-gm weight dropped from 2.5 cm. This insult is sufficient to produce a severe albeit incomplete SCI with profound neurological dysfunction that animals never fully recover from.

Using this model, it was determined that the magnitude of the hemorrhage into the cord increased over the first 24 hr after injury. Animals were sacrificed at ¾ hr and 24 hr after contusion SCI (n=5 rats per group), they were perfused with heparinized saline to remove intravascular blood, and 5-mm segments of cord encompassing the lesion were homogenized and processed using Drabkin's reagent to convert hemoglobin to cyanomethemoglobin for spectrophotometric measurements (Choudhri et al., 1997). Converting values into equivalent microliters of blood showed that values at 24 hr were significantly increased compared to those ¾ hr after contusion, 1.1±0.2 vs. 1.9±0.02 µl, respectively (P<0.05), confirming that this model of SCI is suitable for study of lesion evolution and secondary injury.

Other animals injured in the same way were studied for SUR1 expression in the region of SCI. Low power images of spinal cord sections immunolabeled 24 hr after SCI showed large increases in SUR1 expression in the region of contusion injury, compared to controls (FIGS. 5A-5D and 6A-6B). Co-immunolabeled sections showed that newly expressed SUR1 was co-localized with GFAP (FIGS.

5A-5D) as well as with von Willebrand factor or vimentin (FIGS. 7A-7F), confirming involvement of reactive astrocytes as well as of capillaries.

The specificity of the anti-SUR1 antibody used for immunolabeling was assessed using Western blots. Western blots showed labeling of only a single band (180 kDa) in the range between 116-290 kDa (Simard et al., 2006), indicating that the immunolabeling observed in SCI was specific for SUR1. In specific embodiments, additional studies are performed to characterize the temporal profile of SUR1 up-regulation after SCI, to validate the antibody-based methods using mRNA-based methods, and to confirm that SUR1 up-regulation is associated with up-regulation of $NC_{Ca-ATP}$ channels and not of $K_{ATP}$ channels.

The increase in SUR1 expression following SCI prompted us to perform preliminary experiments to assess the effect of glibenclamide, a potent inhibitor of SUR1 that has long been used as an oral anti-diabetic because it inhibits SUR1-regulated $K_{ATP}$ channels. Animals underwent the same SCI as above, and immediately after, were implanted with mini-osmotic pumps (Alzet 2002, 14 day pump, 0.5 ml/hr; Durect Corporation, Cupertino, Calif.) that delivered either saline or drug s.q. Glibenclamide (Sigma, St. Louis, Mo.) was prepared as a 10 mM stock solution in DMSO, with 15 ml stock solution diluted into 500 ml PBS to give a final concentration of 148 mg/ml. The effective dose of glibenclamide delivered was 75 ng/hr and the effective dose of DMSO delivered was 15 nl/hr. At 3 hr, this dose of glibenclamide resulted in a non-significant decrease in serum glucose, from 236±15 to 201±20 (5-6 rats per group; p=0.19). The amount of DMSO delivered (0.36 µl/day) is 300-1000× less than that required for neuroprotection.

Figure 8:
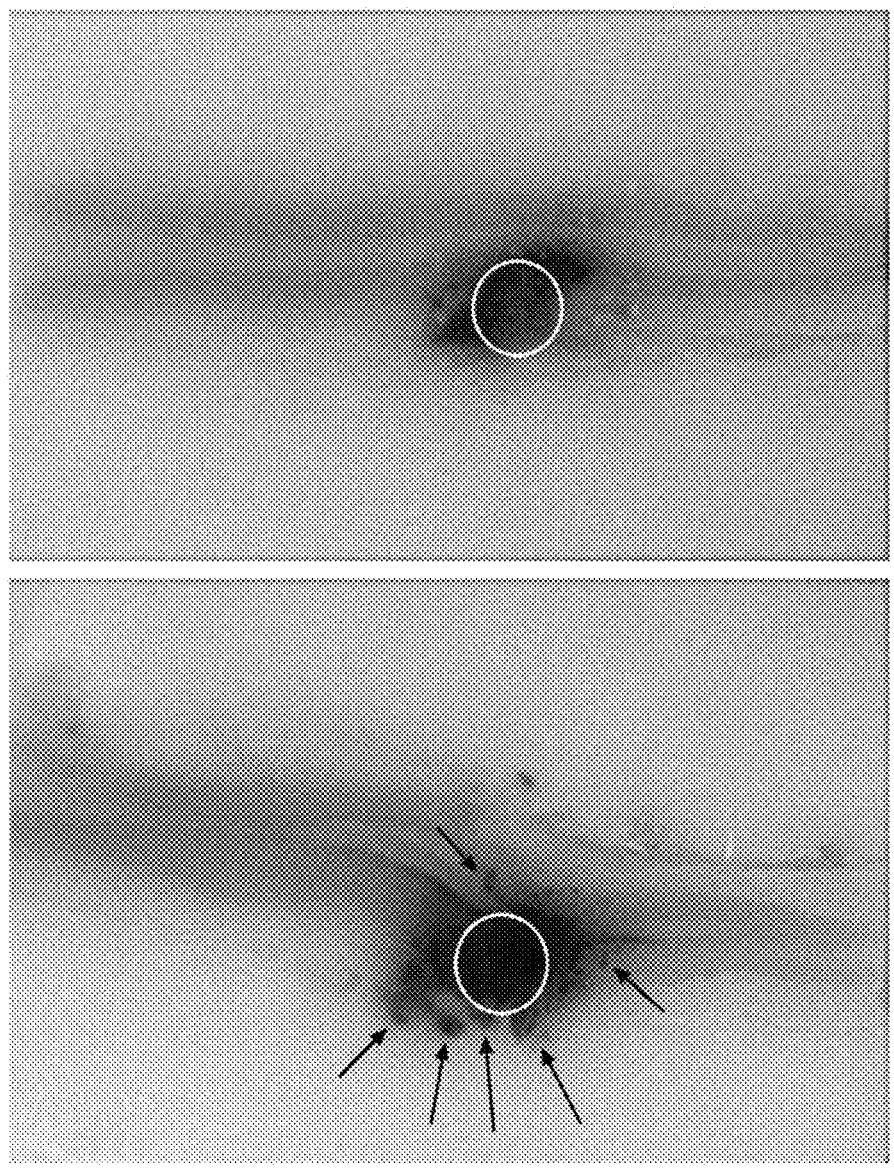
FIG. 8 provides photographs of longitudinal cryosections of cords 24 hr after modest cervical hemi-cord contusion injury, with brown parallel bands being the highly vascularized grey matter of dorsal horns and larger dark masses being intraparenchymal hemorrhages; spinal cords from animals with contusion injury to the left cervical hemi-cord 24 hr before sacrifice, and treated with saline (left) or glibenclamide (right). Primary impact site (white circle) and petechial hemorrhages (arrows) are shown. Note preservation of contralateral gray matter band with glibenclamide (right) but not saline (left); contusion injury obtained using the same weight drop method as described in this proposal.
Figure 9:
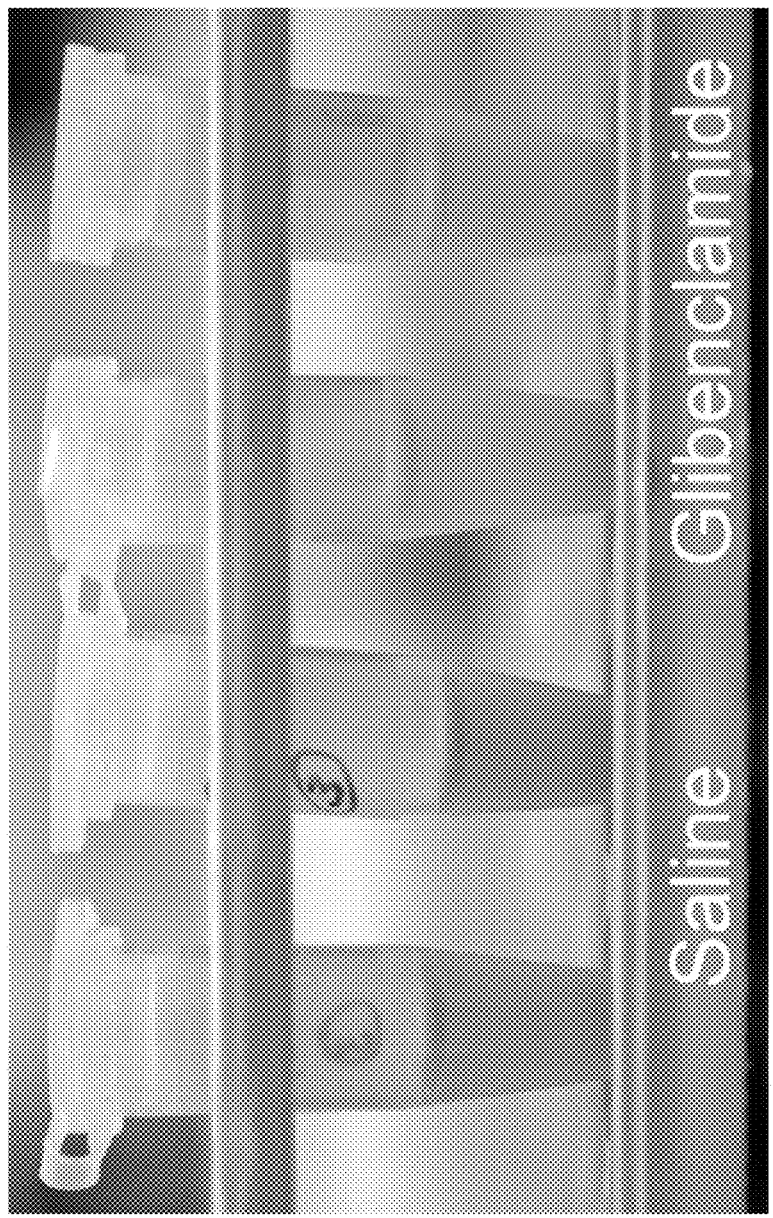
FIG. 9 shows tissue content of blood in the region of contusion SCI is reduced by glibenclamide. Photograph of homogenates of 6-mm segments of cervical spinal cord encompassing the contusion from animals treated with saline or glibenclamide, as indicated; each tube is from a different animal; contusion injury obtained using the same weight drop method as described in this proposal.

Spinal cords were examined 24 hr after SCI. On the dorsal surface at the site of contusion, it was apparent that surface hemorrhages were less prominent in glibenclamide-treated rats than in vehicle-treated rats. Photographs of the tissue blocks used for cryosections demonstrated smaller regions of hemorrhage and better preservation of contralateral grey and white matter with glibenclamide treatment (FIG. 8). In other rats, 6-mm sections of cord were harvested that encompassed the contusion site and we quantified the amount of blood present in tissues after removal of intravascular blood by perfusion at time of euthanasia (n=5-6 rats per group). Tissue homogenates from glibenclamide-treated animals were visibly less bloody that those from vehicle-treated animals (FIG. 9). Quantification for blood showed values at 24 hr of 0.0, 1.9±0.02 and 0.9±0.2 µl, for uninjured, vehicle-treated, and glibenclamide-treated animals, respectively (P<0.05), indicating a significant benefit from glibenclamide treatment.

Example 3

Hemorrhagic Conversion

Figure 10:
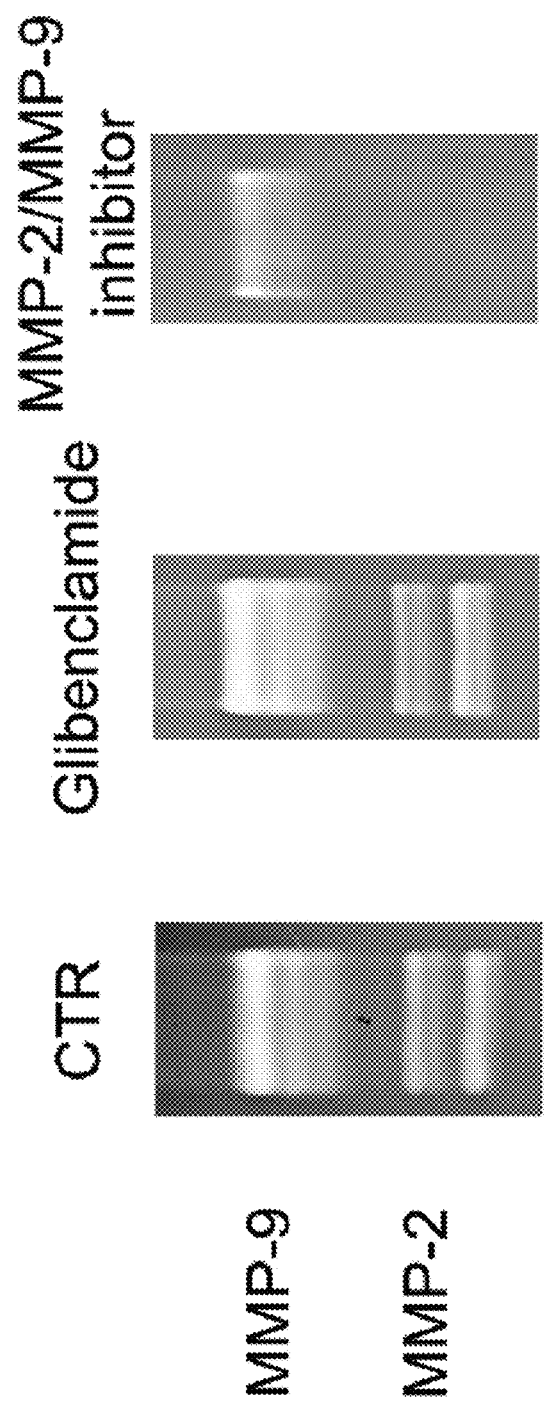
FIG. 10 demonstrates that glibenclamide does not inhibit matrix metalloproteinase (MMP) activity directly. Zymography was performed to show gelatinase activity of recombinant MMP (Chemicon); gelatinase activity was the same under control conditions (CTR) and in the presence of glibenclamide (10 µM), but was significantly reduced by MMP-inhibitor 11 (300 nM; Calbiochem).

In stroke, hemorrhagic conversion has been attributed to activation of matrix metalloproteinases (MMP) (Gidday et al., 2005; Justicia et al., 2003; Lorenzl et al., 2003; Romanic et al., 1998). In specific embodiments, in a SCI model glibenclamide was tested to determine whether it would inhibit MMPs and thereby prevents hemorrhagic conversion. This was studied directly using zymography of recombinant MMPs. Zymography showed that gelatinase activity assayed in the presence of glibenclamide was the same as that assayed without it, although gelatinase activity was strongly inhibited by commercially available MMP inhibitor II (FIG. 10). This finding made it unlikely that glibenclamide was acting directly via MMP inhibition to decrease the hemorrhage in SCI, and indicated instead that a mechanism involving SUR1-regulated $NC_{Ca-ATP}$ channels in capillary endothelium was involved.

Figure 11:
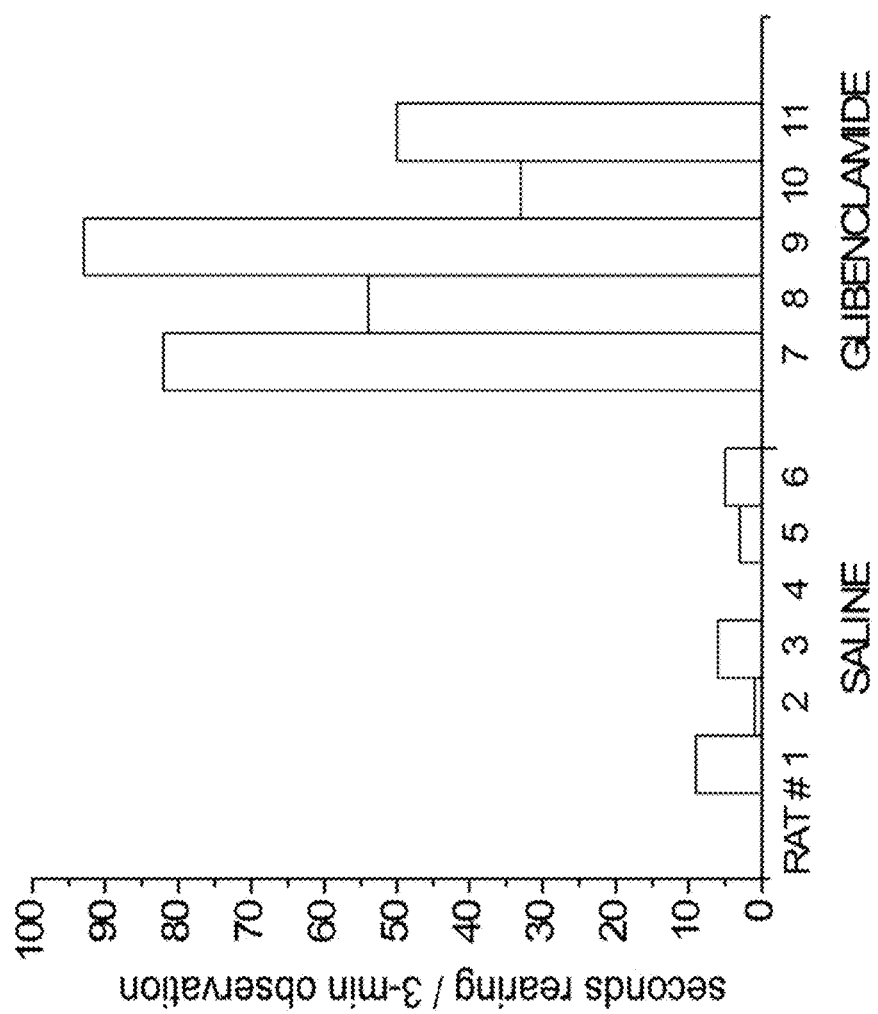
FIG. 11 shows that glibenclamide improves neurological function after cervical hemi-cord contusion injury. 24 hr after injury, rearing behavior (number of seconds with simultaneous elevation of both front paws above the level of the shoulders during a 3-min period of observation) was measured in rats treated with saline or glibenclamide; each bar is from a different animal; contusion injury obtained using the same weight drop method as described in this proposal.

Given the significant reduction in hemorrhage with glibenclamide, we sought to determine whether glibenclamide treatment would also be associated with a more favorable neurological outcome. "Rearing behavior" was quantified 24 hr after injury in the same animals reported on above, treated with either vehicle or glibenclamide, that were assessed for tissue blood. As previously described (Gensel et al., 2006), rats were placed in a glass cylinder to which they had not been previously exposed. A peanut butter treat was placed 8 inches above the floor, and the number of seconds spent with both front paws elevated above shoulder-height was counted during a 3-min period of observation. Data for individual rats are shown in FIG. 11. As is evident, glibenclamide treatment was associated with significantly better truncal and lower extremity function, providing strong evidence that reducing secondary hemorrhage is important for optimizing functional recovery after injury.

Example 4

Isolation of Spinal Cord Microvascular Complexes and Patch Clamp of Capillaries

Figure 12:
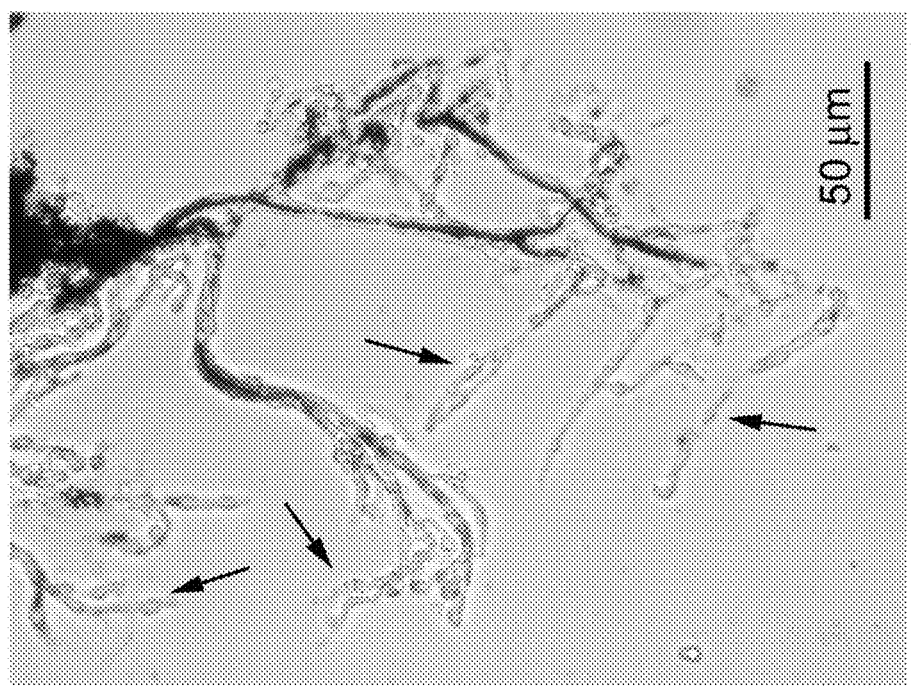
FIG. 12 demonstrates a microvascular complex freshly isolated from normal (uninjured) rat spinal cord. Phase-contrast micrograph showing magnetic particles inside of precapillary arteriole (black tissue near top) along with attached capillaries more distally. Arrows point to clear (unfilled) capillaries that are targeted for patch clamp. Note minimal cellular debris.

Microvascular complexes were isolated from normal (uninjured) rat spinal cord using a method based on perfusion with magnetic particles (details of method given below). Magnetic separation yielded microvascular complexes that typically included a precapillary arteriole plus attached capillaries (FIG. 12). As is evident from the image, unambiguous identification of capillaries for patch clamping attached capillary endothelial cells (FIG. 12, arrows) should be readily achieved.

Figure 13A:
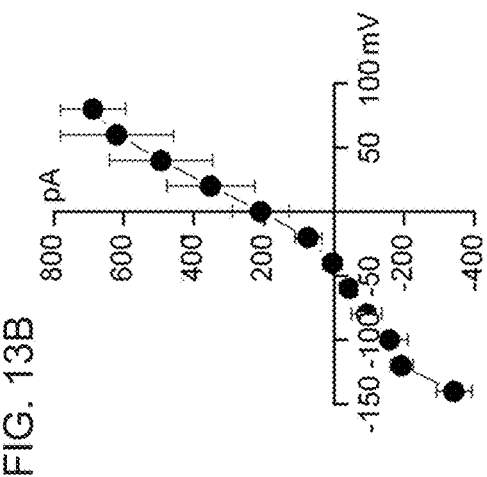
FIGS. 13A-13D demonstrate that whole-cell currents during step pulses (−140 to +80 mV, 20 mV intervals) in capillary endothelial cells are still attached to freshly isolated spinal cord microvascular complexes, as in FIG. 12. Standard physiological solutions inside and out, except that ATP (2 mM) was either included (FIG. 13A, FIG. 13B) or excluded (FIG. 13C, FIG. 13D) in the pipette. Current-voltage curves show means±S.E. for 4 and 5 cells, respectively.
Figure 13B:
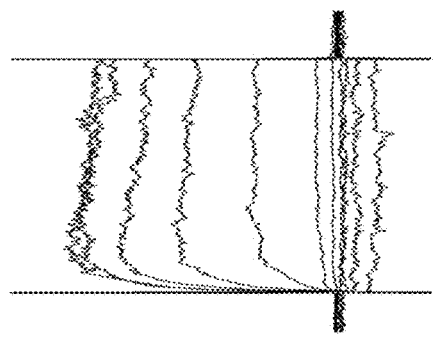
Figure 13C:
Figure 13D:
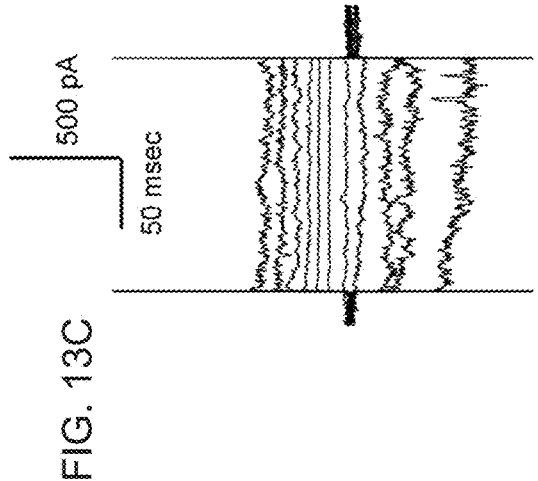

Capillary endothelial cells were patch clamped while still attached to intact microvascular complexes using a conventional whole cell method. Cells were studied with standard physiological solutions in the bath and in the pipette, either with or without 2 mM ATP in the pipette solution (FIGS. 13A-13D). With ATP in the pipette, membrane currents showed time-dependent activation (FIG. 13A) with a complex, weakly rectifying current-voltage relationship that reversed near −50 mV (FIG. 13B). When ATP was excluded from the pipette solution, outward currents were smaller, currents no longer activated in a time-dependent fashion (FIG. 13C), the current-voltage relationship was more linear and it reversed at a more positive potential, near −20 mV (FIG. 13D). These recordings demonstrate the feasibility of patch clamping freshly isolated capillary endothelial cells that are still attached to intact microvascular complexes from spinal cord and the identification of ATP-sensitive currents in cells of these intact microvascular complexes.

Example 5

Patch Clamp of Cultured Endothelial Cells

Figure 14C:
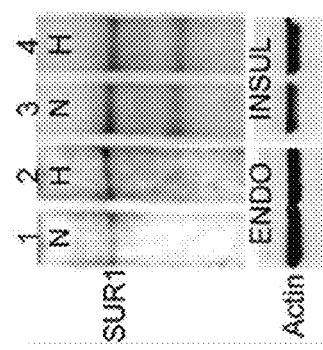
FIGS. 14A-14C show immunofluorescence images of human aortic endothelial cells (HAEC) labeled for SUR1 (antibody from Santa Cruz), 48 hr after exposure to normoxic (FIG. 14A; room air) or hypoxic (FIG. 14B; 1% $O_2$) culture conditions; 1% serum. Width of photographs, 100 µm.
Figure 14A:
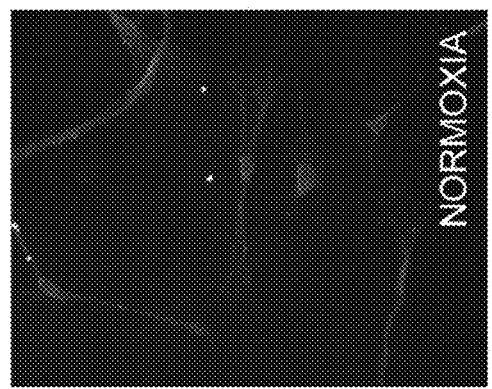
Figure 14B:
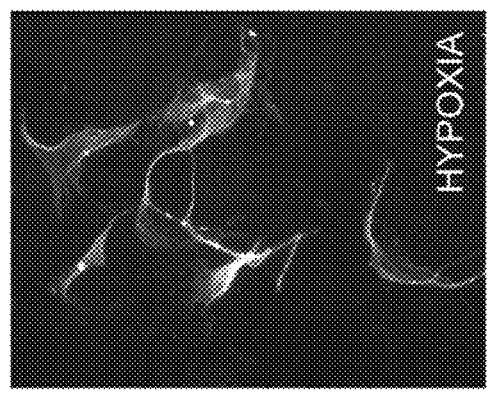

In addition to studying freshly isolated capillary endothelial cells from rat spinal cord, cultured endothelial cells from human aorta (ScienCell, SanDiego Calif.) were also studied. The purpose with these studies was to investigate whether hypoxia/ischemia can lead to up-regulation of the SUR1-regulated $NC_{Ca-ATP}$ channels in endothelial cells, a finding that was previously reported for astrocytes and neurons (Chen et al., 2003; Simard et al., 2006), but not endothelial cells. Endothelial cells were cultured under normoxic (room air) and hypoxic (1% $O_2$) conditions. Cells cultured under both conditions were immunolabeled for SUR1, the regulatory subunit of both $K_{ATP}$ and $NC_{Ca-ATP}$ channels. Only very faint labeling for SUR1 was observed in cells maintained under normoxic conditions (FIG. 14A). By contrast, cells subjected to prolonged hypoxia invariably showed very prominent labeling for SUR1 (FIG. 14B).

Figure 15A:
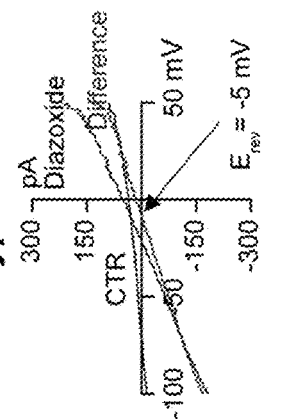
FIGS. 15A-15E demonstrate whole-cell currents during ramp pulses (4/min; HP, −70 mV) in HAEC after exposure to normoxic (FIG. 15A) or hypoxic (FIG. 15B-FIG. 15E) culture conditions, as in FIGS. 14A-14C. Difference current obtained by subtracting control current from that after diazoxide. Diazoxide also induced an inward current at the holding potential, −50 mV (FIG. 15C). Single channel recordings of inside-out patches with $Cs^+$ as the principal cation, with channel openings inhibited by ATP on the cytoplasmic side (FIG. 15D). Channel amplitude at various potentials gave a slope conductance of 37 pS (data from 7 patches) (FIG. 15E).
Figure 15B:
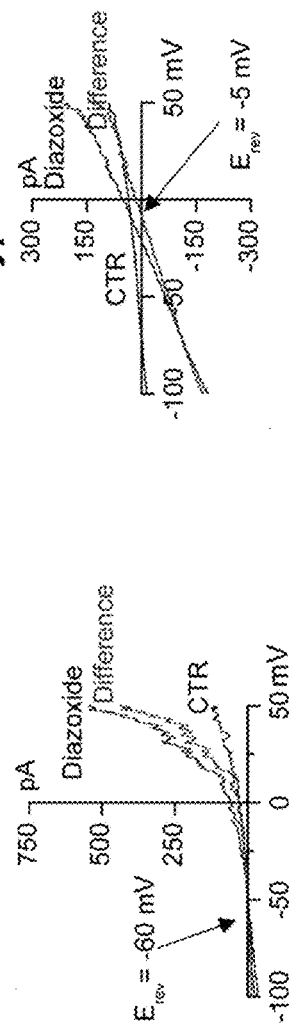
Figure 15C:
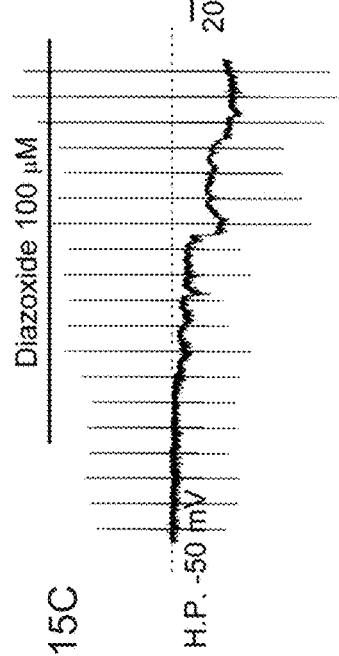

Patch clamp of cells maintained under normoxic conditions showed a voltage-dependent current that was significantly increased by application of the SUR1-specific channel opener, diazoxide (FIG. 15A). The diazoxide-induced current (difference current in FIG. 15A) reversed at E(K) consistent with an SUR1-regulated $K_{ATP}$ channel current. By contrast, patch clamp of cells maintained under hypoxic conditions showed an ohmic current that was also significantly increased by application of diazoxide, but that reversed near 0 mV (FIG. 15B), consistent with an SUR1-regulated non-selective cationic current. In cells from hypoxia, but not normoxia, diazoxide also induced an inward current at the holding potential of −50 mV (FIG. 15C), again consistent with an SUR1-regulated non-selective cationic current but not a $K_{ATP}$ channel current.

Figure 15D:
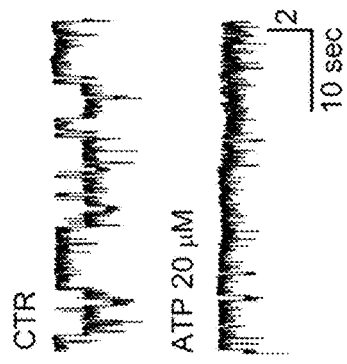
Figure 15E:
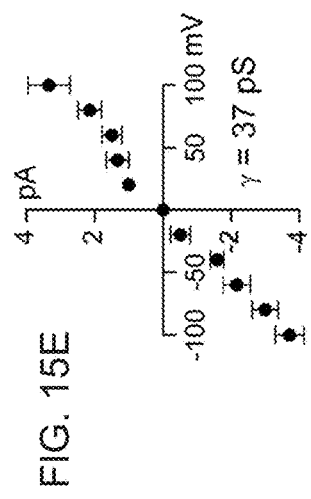

Inside-out patches from cells maintained under hypoxic conditions were also studied. For these experiments, there was 1 µM $Ca^{2+}$ in the bath solution, and it was replaced with $Na^+$ in the bath and $K^+$ in the pipette solutions with $Cs^+$ to completely block all $K^+$ channels. Excision of patches revealed channels with frequent spontaneous openings (FIG. 15D, CTR) that were inhibited by addition of 20 µM ATP to the bath (FIG. 15D, ATP; same patch as CTR). Measurements of single channel amplitudes at various potentials revealed a slope conductance of 37 pS (FIG. 15E). Notably, a current that: (i) is induced by prolonged hypoxia, (ii) is activated by diazoxide, (iii) reverses near 0 mV, (iv) exhibits a single channel conductance of 37 pS, and (v) is blocked by ATP on the cytoplasmic side, is completely consistent with previous reports on the $NC_{Ca-ATP}$ channel in astrocytes and neurons (Chen and Simard, 2001; Chen et al., 2003; Simard et al., 2006). This very exciting finding with endothelial cells extends previous observations on neurons and astrocytes, and demonstrates for the first time that a channel consistent with the $NC_{Ca-ATP}$ channel may also be expressed outside of the CNS. The discovery of these channels in human aorta indicates that blockade of these channels, inhibition of the activity of these channels, and/or inhibition of the expression of these channels in human aorta, and in other non-CNS vessels, organs, and tissues could treat, ameliorate, or prevent damage and/or disease in these vessels, organs, and tissues. This discovery also shows that blockade of these channels, inhibition of the activity of these channels, and/or inhibition of the expression of these channels in human aorta, and in other non-CNS vessels, organs, and tissues, could aid in the protection and/or preservation of such vessels, organs, and tissues when they are removed for treatment, transport, and/or transplantation.

Example 6

SUR1 Regulation of $NC_{Ca-ATP}$ Channel and Secondary Injury in SCI

In certain aspects of the invention, SUR1, which regulates the novel $NC_{Ca-ATP}$ channel, is directly responsible for certain pathological manifestations in secondary injury in SCI, and blocking this channel with glibenclamide results in significant improvement in outcome following SCI. The ability to selectively and specifically reduce edema and hemorrhagic conversion after SCI presents unique translational opportunities.

In specific embodiments, the time course of pathophysiological events during the first several hours after SCI is established, when initial causes and manifestations of secondary injury become evident. Determination of the temporal course for up-regulation of the SUR1-regulated $NC_{Ca-ATP}$ channel is achieved. In other aspects of the invention, the temporal course for evolution of the principal manifestations of secondary injury, i.e., edema and hemorrhage, is achieved. It seems curious to note that, despite years of research on secondary injury, there are as yet no systematic descriptions of the time courses of these processes as they evolve during the first several hours after SCI. Such information is critical, however, for rationally designing interventions and therapies to reduce secondary injury. In another specific aspect of the invention, the effect of inhibition of SUR1-regulated $NC_{Ca-ATP}$ channels using various doses of glibenclamide is characterized, with the specific goals of determining the time-window during which treatment can be usefully given and the optimal dose required. Finally, in another embodiment of the invention, the previous work is studied to demonstrate that optimal treatment with glibenclamide leads to significant improvements on in neurological function following SCI.

The Model of Contusion SCI.

The contusion SCI model used is based on the description of Soblosky et al. (2001). Adult female Long-Evans rats are anesthetized (Ketamine and Zylazine) and a hemilaminectomy is made at C4-5 to expose the dura, in preparation for creating a cervical hemi-cord contusion on the left. Prior to injury, the spinous process of C6 is rigidly fixed to a frame to minimize displacement of the spine at the time of impact. Physiological parameters including temperature and blood gases are monitored and maintained within appropriate physiological ranges.

For previous data, cervical hemi-cord contusions were generated using a weight-drop device, consisting of an impactor (a thin light rod, 1.5 mm diameter, rounded at the tip and guided within a glass cylinder by a 5-mm polypropylene ball at the top) that was gently placed on the exposed dura and that was activated by weight drop (10-gm weight dropped from 2.5 cm). Controls underwent sham surgery that included laminectomy but no weight drop. However, a pneumatic impact device (Pittsburgh Precision Instruments, Inc) may be employed with which specific injury parameters (depth, force, velocity) are programmable, and with which "bounce back" that may be experienced with the simple weight-drop device is eliminated, making the physical impact more uniform.

Drug Treatment Following SCI.

Within 2-3 min of spinal cord injury, mini-osmotic pumps (Alzet 2002, 14 day pump, 0.5 ml/hr; Durect Corporation, Cupertino, Calif.) are implanted that deliver either vehicle or drug subcutaneously. The principal advantage of drug delivery by constant infusion, as opposed to a single i.v. or i.p. bolus injection, is that it assures constant occupancy of high affinity receptors, in this case, SUR1.

For certain experiments, glibenclamide was delivered at 75 ng/hr (no loading dose). For some of the studies described herein, the effects of various doses of glibenclamide are studied, including use of a loading dose, when start of treatment is delayed after injury. In this embodiment, treatment is mimicked that could be implemented in humans following injury, including use of a loading dose and constant infusion, coupled with a delay in start of treatment (i.p.

Example 7

Determination of the Time-Course for Up-Regulation of the Glibenclamide-Sensitive, SUR1-Regulated $NC_{Ca-ATP}$ Channel Following Spinal Cord Contusion The present invention concerns a time-course for SUR1 protein and mRNA, using Westerns and qPCR; cellular localization, using immunohistochemistry and in situ hybridization for SUR1; and channel function using patch clamp electrophysiology on isolated cells. In one embodiment of the invention, SUR1 expression is transcriptionally up-regulated over several hours after SCI. In another embodiment of the invention, SUR1 expression is up-regulated in neurons, astrocytes and capillary endothelial cells. In an additional embodiment of the invention, SUR1 up-regulation is associated with $NC_{Ca-ATP}$ channels, not $K_{ATP}$ channels Data on contusion SCI indicate that SUR1 is up-regulated 24 hr after injury in capillaries and astrocytes, and in stroke it indicated that SUR1-regulated $NC_{Ca-ATP}$ channels are up-regulated in neurons as early as 2-3 hr after onset of ischemia (Simard et al., 2006). Channel up-regulation in neurons and astrocytes is thought to be critical for cytotoxic edema, whereas channel up-regulation in capillary endothelial cells is thought to be critical for ionic edema, vasogenic edema and hemorrhagic conversion. Understanding the time course for channel expression is useful for determining the treatment window.

SUR1 forms the regulatory subunit for both $K_{ATP}$ and $NC_{Ca-ATP}$ channels. Whereas $K_{ATP}$ channels are considered protective, by virtue of the fact that they help polarize cells and thereby reduce $Ca^{2+}$ influx (Heurteaux et al., 1995; Cohen et al., 2000), $NC_{Ca-ATP}$ channels are destructive, in that opening leads to cell death (Chen and Simard, 2001; Chen et al., 2003; Simard et al., 2006). It is thus important to determine whether SUR1 up-regulation in SCI is associated with $K_{ATP}$ or $NC_{Ca-ATP}$ channels.

In one embodiment of the invention, the time course for up-regulation of $NC_{Ca-ATP}$ channels following contusion SCI is determined. In certain embodiments, this is accomplished with three exemplary series of studies. First, Western blots are utilized to measure the increase in SUR1 protein and qPCR experiments are utilized to measure the increase in mRNA for SUR1. Because a transcriptional mechanism is believed to be involved, in certain aspects, the qPCR experiments provide not only direct confirmation of involvement of transcription, but also serve to indirectly validate that the protein measured by Western blotting is in fact SUR1. As regards specificity of antibody, it was previously shown that the anti-SUR1 antibody to be used for Westerns (and immunochemistry, see below) exhibits a high degree of specificity for SUR1, and labels only a single band (180 kDa) in the range between 116-290 kDa (Simard et al., 2006). Secondly, apart from addressing quantitative changes in SUR1 protein and mRNA, it is determined which cells are up-regulating transcriptional expression of SUR1. This is done using double immunolabeling experiments, with validation again provided at the mRNA level using in situ hybridization. Third, it is determined whether newly up-regulated SUR1 is associated with either $K_{ATP}$ or $NC_{Ca-ATP}$ channels. Although the pore-forming subunits of the $NC_{Ca-ATP}$ channel is the TRPM4 channel, or a related or very similar channel, distinguishing between the two may be done using patch clamp experiments, and relying on the clear differences in biophysical properties of the two channels to distinguish between the $K_{ATP}$ channels and the $NC_{Ca-ATP}$ channels.

Time-Course for SUR1 Protein and mRNA, Using Westerns and qPCR

In these studies, there is focus on SUR1 as the measurement target, as a surrogate for the "complete" target, the SUR1-regulated $NC_{Ca-ATP}$ channel. This strategy is utilized because of the ease and feasibility of measuring SUR1 versus the difficulty of measuring the pore-forming subunit of the channel, which has not yet been cloned and for which no antibody exists. Notably, it is known from in vivo knock-down experiments that knock-down of SUR1 alone is sufficient to prevent expression of a functional channel (Simard et al., 2006), and thus measuring SUR1 can be viewed as a reliable strategy for measuring channel expression.

SUR1 protein is measured in 7 groups of animals: in controls (sham surgery) and in animals with contusion SCI at 6 times after injury, at ¾, 1.5, 3, 6 12, 24 hr. As a control, blots are stripped and re-blotted for Kir6.1 and Kir6.2, the pore-forming subunits of $K_{ATP}$ channels. Each of the seven groups require 5 rats per group.

SUR1 mRNA is measured in 7 groups of animals: in controls (sham surgery) and in animals with contusion SCI at 6 times after injury, at ¾, 1.5, 3, 6 12, 24 hr. Each of the seven groups require 5 rats per group.

Preparation of tissues. After death, animals are perfused with heparinized saline to remove blood from the intravascular compartment. For the qPCR experiments, the perfusion solution includes RNAlater (Ambion, Austin Tex.), to prevent RNA degradation. The cervical spinal cord is harvested, sectioned to include 5 mm rostral and 5 mm caudal to the impact site. Tissues are homogenized in lysis buffer.

Western blots. Lysates of whole tissues are prepared and gels (NuPAGE® 3-8% Tris-Acetate gels; Novex, Invitrogen, Carlsbad, Calif.) are processed as described (Perillan et al., 2002). Whole tissue lysates are analyzed for SUR1 (SC-5789; Santa Cruz Biotechnology), Kir6.1 (Santa Cruz) or Kir6.2 (Santa Cruz). Membranes are stripped and re-blotted for β-actin (1:5000; Sigma, St. Louis, Mo.), which is used to normalize the primary data. Detection is carried out using the ECL system (Amersham Biosciences, Inc.) with routine imaging (Fuji LAS-3000) and quantification (Scion Image, Scion Corp, Frederick, Md.).

The specificity of the SUR1 antibody has been documented (Simard et al., 2006). The specificity of the Kir6.x antibodies is confirmed by performing Western blots on insulinoma RIN-m5f cells (Kir6.2) and rat heart (Kir6.1).

qPCR. Areas of contusion are sampled for total mRNA. Reverse transcription of 1 µg of total RNA (normalized conditions) with random hexonucleotides according to the manufacturer's protocol (Applied Biosystems) is done, and real-time PCR reactions are performed with an ABI PRISM 7300 Sequence Detector System (Applied Biosystems) using a TaqMan based protocol in a 96-well plate format. Taq Man probes and primers are selected with Primer Express 2.0 (Applied Biosystems) software and synthesized by Applied Biosystems. Primer sequences: H1 histone family member (housekeeping gene): CGGACCACCCCAAG-TATTCA (forward) (SEQ ID NO:1); GCCGGCACGGT-TCTTCT (reverse) (SEQ ID NO:2); CATGATCGTGGCTGCTATCCAGGCA (TaqMan Probe) (SEQ ID NO:3). SUR1: GAGTCGGACTTCTCGCCCT (forward) (SEQ ID NO:4); CCTTGACAGTGGAC-CGAACC (reverse) (SEQ ID NO:5); TTCCACATCCTG- GTCACACCGCTGT (TaqMan Probe) (SEQ ID NO:6). Amplification reactions are performed using a TaqMan amplification kit (Applied Biosystems) according to the manufacturer's protocol, in 25 µl of reaction volume with 2 µl of cDNA. The amplification program consists of a 5-min holding period at 95° C., followed by 40 cycles of 95° C. for 30 seconds, 60° C. for 30 seconds and 72° C. for 30 seconds. Relative quantification is performed using a standard curve method (User Bulletin #2, PE Applied Biosystems). All samples are run in triplicate.

Cellular Localization, Using Immunohistochemistry and In Situ Hybridization for SUR1

In these studies, SUR1 is focused on for determining the cell types responsible for SUR1 up-regulation. For this, double immunolabeling studies are performed, with specific attention to labeling neurons with NeuN, astrocytes with GFAP and vimentin, and capillary endothelial cells with vonWillebrand factor and vimentin (Schnittler et al., 1998) Also, in situ hybridization experiments are performed to help validate the SUR1 immunohistochemistry.

Immunolabeling studies are performed for SUR1 plus double labeling for a second marker (NeuN, GFAP, vimentin, vWf) in 7 groups of animals: in controls (sham surgery) and in animals with contusion SCI at 6 time after injury, at ¾, 1.5, 3, 6 12, 24 hr. Each of the seven groups require 5 animals/group.

In situ hybridization studies are performed for SUR1 mRNA in 4 groups of animals: in controls (sham surgery) and in animals with contusion SCI at 3 time after injury, at 1.5, 6 and 24 hr. Each of the four groups require 5 animals/group.

Preparation of tissues. After death, animals are perfused with heparinized saline to remove blood from the intravascular compartment followed by 4% paraformaldehyde. For the in situ hybridization studies, perfusion includes RNAlater (Ambion, Austin Tex.), to prevent RNA degradation. The cervical spinal cord is harvested, cut to include 7-8 mm rostral and 7-8 mm caudal to the impact site. The cervical cord is cryoprotected using 30% w/v sucrose.

Immunohistochemistry. Three cryosections are used for double labeling (SUR1+ NeuN, SUR1+ GFAP; SUR1+ vWf). Cryosections are immunolabeled using standard techniques. After permeabilizing (0.3% Triton X-100 for 10 min), sections are blocked (2% donkey serum for 1 hr; Sigma D-9663), then incubated with primary antibody directed against SUR1 (1:200; 1 hr at room temperature then 48 h at 4° C.; SC-5789; Santa Cruz Biotechnology). After washing, sections are incubated with fluorescent secondary antibody (1:400; donkey anti-goat Alexa Fluor 555; Molecular Probes, Oreg.). For co-labeling, primary antibodies were used that were directed against NeuN (1:100; MAB377; Chemicon, Calif.); GFAP (1:500; CY3 conjugated; C-9205; Sigma, St. Louis, Mo.); vonWillebrand factor (1:200; F3520, Sigma) vimentin (1:200; CY3 conjugated; C-9060, Sigma) and, as needed, species-appropriate fluorescent secondary antibodies. Fluorescent signals are visualized using epifluorescence microscopy (Nikon Eclipse E1000).

In situ hybridization. Non-radioactive digoxigenin-labeled probes are made according to the manufacturer's protocol (Roche) using SP6 or T7 RNA polymerase. RNA dig-labeled probes (sense and anti-sense) are generated from pGEM-T easy plasmids (Promega) with the SUR1 insert (613 bp) flanked by the primers: 5' AAGCACGTCAACGC-CCT 3' (forward) (SEQ ID NO:7); 5' GAAGCTTTTCCG-GCTTGTC 3' (reverse) (SEQ ID NO:8). Fresh-frozen (10 µm) or paraffin-embedded (4 µm) sections of rat brain (3, 6, 8 hours after SCI) are used for in situ hybridization (Anisimov et al., 2002).

Channel Function Using Patch Clamp Electrophysiology on Isolated Cells

In these studies, it is determined electrophysiologically that SUR1 up-regulation is linked to expression of functional $NC_{Ca-ATP}$ and not $K_{ATP}$ channels.

$K_{ATP}$ channels are heteromultimers formed by 2 types of subunits, a regulatory subunit (SURx) and a pore-forming subunit (Kir6.x) (Bryan and Aguilar-Bryan, 1999; Ashcroft and Gribble, 2000; Liss and Roeper, 2001; Seino, 2003). The work on R1 astrocytes shows that $NC_{Ca-ATP}$ channels are also formed by 2 types of subunits, a regulatory subunit unambiguously identified as SUR1, and a pore-forming subunit that is very different from Kir6.x, based on its different conductivity and regulation by internal $Ca^{2+}$ (Chen and Simard, 2001; Chen et al., 2003); the pore-forming subunit is TRPM4. In previous data, it is shown that one of the two components of the $NC_{Ca-ATP}$ channel, the SUR1 regulatory subunit, is expressed in capillaries and neurons. However, this does not distinguish $NC_{Ca-ATP}$ channels from $K_{ATP}$ channels, for at least the reason that each may associate with a SUR1 subunit. The studies in this embodiment are useful to identify the channel electrophysiologically based on its biophysical properties.

The data on SCI indicate that glibenclamide is extraordinarily effective in reducing hemorrhagic conversion even when given at a low dose that reduces serum glucose only marginally. In certain aspects, this high potency reflects not only the high affinity of the drug at the receptor ($EC_{50}$=48 nM at neutral pH) (Chen et al., 2003), but also the fact that ischemic tissues are at lower pH (~6.5) (Nedergaard et al., 1991), coupled with the relatively acidic $pK_a$ of glibenclamide (6.3), resulting in greater lipid solubility and thus greater tissue concentration of the compound in ischemic regions compared to normal regions at neutral pH.

Patch clamp electrophysiology. Numerous papers from the lab of the inventor present detailed accounts of the patch clamp methodologies that are used, including whole-cell, inside-out, outside-out and perforated patch methods (Chen and Simard, 2001; Chen et al., 2003; Perillan et al., 2002; Perillan et al., 1999; Perillan et al., 2000).

The overall design of the studies follows the strategy previously used with R1 astrocytes and neurons for characterizing the $NC_{Ca-ATP}$ channel (Chen and Simard, 2001; Chen et al., 2003; Simard et al., 2006). Initial experiments are carried out using a whole-cell perforated patch configuration to characterize macroscopic currents, and to test the overall response to ATP depletion induced by exposure to the mitochondrial poisons, Na azide or Na cyanide/2-deoxyglucose, as used in a previous paper (Chen and Simard, 2001). This configuration is also useful for characterizing the response to the SUR1 activators (a.k.a. "$K^+$ channel openers"): if the cell expresses $NC_{Ca-ATP}$ channels, diazoxide will activate an inward current that reverses near zero millivolts, whereas if the cell expresses $K_{ATP}$ channels, diazoxide will activate an outward current that reverses near −70 mV.

The channels may additionally be characterized using inside-out patches for single channel recordings. This method makes it simpler to study endothelial cell patches, which can thus be obtained from either intact isolated capillaries or from single isolated endothelial cells. In addition, this method allows precise control of $Ca^{2+}$, $H^+$ and ATP concentrations on the cytoplasmic side, and for this reason is preferable to whole-cell recordings. Also, as previously shown (Chen et al., 2003), in this configuration anti-SUR1 antibody binds to the channel and inhibits glibenclamide action, making positive, antibody-based identification of the channel readily feasible during the patch clamp experiment.

The single channel slope conductance is obtained by measuring single channel currents at various membrane potentials using $Na^+$, $K^+$ and $Cs^+$ as the charge carrier, at different pH's including pH 7.9, 7.4, 6.9 and 6.4. The slope conductance with $Cs^+$ assures that a $K^+$ channel is not involved. Study of conductance at different values of pH is important for determining channel properties in ischemia, which is associated with acidic pH.

The probability of channel opening (nPo) is measured at different concentrations of intracellular calcium ($[Ca^{2+}]_i$), at different pH's including pH 7.9, 7.4, 6.9 and 6.4. The $NC_{Ca-ATP}$ channel in R1 astrocytes is regulated by $[Ca^{2+}]_i$, a unique feature that distinguishes the $NC_{Ca-ATP}$ channel from $K_{ATP}$ channel.

The concentration-response relationship was measured for channel inhibition by AMP, ADP, ATP at pH 7.9, 7.4, 6.9 and 6.4. The $NC_{Ca-ATP}$ channel in R1 astrocytes is inhibited by ATP, but not by ADP or AM P, a feature that is unique for SUR1-regulated channels (Chen and Simard, 2001). There is a potentially important interaction between hydrogen ion and nucleotide binding that may also be very important in the context of ischemia, and thus these measurements are performed at various values of pH.

The concentration-response for channel inhibition by glibenclamide is also studied. The effect of glibenclamide is studied at different pH's including pH 7.9, 7.4, 6.9 and 6.4. The importance of these experiments is several fold. Pharmacological data at neutral pH are critical to characterizing the channel and for comparison with the channel in R1 astrocytes. Values for half-maximum inhibition by sulfonylureas provide critical information on involvement of SUR1 vs. other SUR isoforms and other potential targets. As discussed above, because glibenclamide and other sulfonylureas are weak acids, they are more lipid soluble at low pH and thus can be expected to access the membrane more readily at low pH. In specific embodiments, this phenomenon of increased membrane permeability at low pH may account for the exceptional potency of glibenclamide in ameliorating pathological manifestations of cerebral ischemia and spinal cord injury.

Isolation of spinal cord microvessels with attached capillaries. The method we are using is adapted in part from Harder and colleagues (1994), with modifications as previously reported (Seidel et al., 1991). Briefly, a rat undergoes transcardiac perfusion of 50 ml of heparinized PBS containing a 1% suspension of iron oxide particles (particle size, 10 μm; Aldrich Chemical Co.). The contused spinal cord is removed, the pia and pial vessels are stripped away, the cord is split longitudinally and white matter bundles are stripped away to leave mostly gray matter tissue, which is minced into pieces 1-2 mm3 with razor blades. Tissue pieces are incubated with dispase II (2.4 U/ml; Roche) for 30 min with agitation in the incubator. Tissues are dispersed by trituration with a fire-polished Pasteur pipette. Microvessels are adhered to the sides of 1.5 ml Eppendorf tubes by rocking 20 min adjacent to a magnet (Dynal MPC-S magnetic particle concentrator; Dynal Biotech, Oslo, Norway). Isolated microvessels are washed in PBS×2 to remove cellular debris and are stored at 4° C. in physiological solution (Seidel et al., 1991). For patch clamp study of capillary cells, an aliquote of microvessels is transferred to the recording chamber, and using phase contrast microscopy, capillaries near the end of the visualized microvascular tree are targeted for patch clamping.

Isolation of neurons. Neurons are isolated from vibratome sections as recently described for brain (Simard et al., 2006). Tissues are prepared at 2-3 hr after contusion SCI. The spinal cord is removed and vibratome sections (300 μm) are processed as described (Hainsworth et al., 2001; Kay and Wong, 1986; Moyer and Brown, 1998) to obtain single neurons for patch clamping. Selected portions of slices are incubated at 35° C. in HBSS bubbled with air. After at least 30 min, the pieces are transferred to HBSS containing 1.5 mg/ml protease XIV (Sigma). After 30-40 min of protease treatment, the pieces are rinsed in enzyme-free HBSS and mechanically triturated. For controls, cells from sham operated animals are utilized, where there are very different current recordings, in specific embodiments, including possibly $K_{ATP}$ channel currents, but not $NC_{Ca-ATP}$ channel currents.

Cells are allowed to settle in HBSS for 10-12 min in a plastic Petri dish mounted on the stage of an inverted microscope. Large and medium-sized pyramidal-shaped neurons are selected for recordings. At this early time of 2-3 hr, only neurons and capillaries, not astrocytes, show up-regulation of SUR1. Therefore, large isolated cells with SUR1 responses in our patch clamp experiments are most likely to be neurons. This is verified in a subset of cells by single cell RT-PCR for neuron-specific enolase (Liss, 2002; Sucher et al., 2000; Suslov et al., 2000; Volgin et al., 2004).

In certain aspects of the invention, SUR1 is progressively up-regulated at both the protein and mRNA levels in the region of contusion, that up-regulation is prominent in neurons and capillary endothelial cells, and that up-regulation requires several hour s to reach a maximum. Moreover, in other embodiments, SUR1 up-regulation is associated with up-regulation of functional $NC_{Ca-ATP}$ channels, not of $K_{ATP}$ channels, and that Kir6.x pore forming subunits are not involved.

In alternative embodiments, $K_{ATP}$ instead of or in addition to $NC_{Ca-ATP}$ channels are found.

Example 8

Determination of the Time-Course for Evolution of Secondary Injury (Edema and Hemorrhagic Conversion) and Progression of Lesion Size In one embodiment, a time course of edema is determined, measured as excess water in the cord at 0, ¾, 1.5, 3, 6, 12, 24 hr after injury. In another embodiment, time course of hemorrhagic conversion is determined, measured as excess hemoglobin in the cord at 0, 1.5, 3, 6, 12, 24 hr after injury. In a further embodiment, progression of lesion volume is determined, assessed with myelin stain (Eriochrome cyanine-R) and RBC stain at 0, 1.5, 3, 24 hr after injury.

In a specific embodiment of the invention, edema fluid (excess water) increases with time after contusion SCI, commensurate with the time course for SUR1 expression. In another specific embodiment, hemorrhagic conversion (tissue content of Hgb) increases with time after contusion SCI, commensurate with the time course for SUR1 expression. In a further specific embodiment, lesion size increases with time after contusion SCI, commensurate with the time course for SUR1 expression The literature gives several examples showing that the lesion in contusion SCI changes with time, as penumbral tissues succumb to secondary damage and add their volume of secondarily damaged tissues to the volume of primarily injured tissues. In general, this is a well-accepted concept. However, clear delineation of the magnitude and time course of these changes is missing from the available literature. Clearly, if the magnitude of the change is small, implying that initially the penumbra is only a small fraction of the final lesion, or if the time course of change is very rapid, then hope for successful treatment to prevent penumbral loss would be small. Conversely, if the magnitude of the change is large, and if the time course of progression is sufficiently slow, this would argue that prompt treatment aimed at reducing secondary injury would be worthy of pursuit.

The rationale for establishing the time course of pathological changes following initial injury is clear: this information is of utmost importance for determining the treatment window within which secondary injury could be beneficially attacked. That this is true becomes evident by considering the series of 3 NASCIS trials on SCI in humans, in which progressively shorter treatment windows, culminating in a 3-8 hr window depending on treatment duration, were used to assess potential beneficial effects of methylprednisolone (Kwon et al., 2004).

Historically, edema has been the principal target of treatment in attempts to limit secondary injury (Kwon et al., 2004). However, given the severe neurotoxic nature of blood, a more fruitful target for intervention may be the evolution of hemorrhage (hemorrhagic conversion) that occurs within the first several hours of contusion. This aspect of the pathophysiology of SCI was first studied by Khan et al. (1985) and Kawata et al. (1993), in which conflicting findings on lesion progression were reported. The data showing a large difference in blood content between Ø and 24 hr after contusion SCI, are in excellent agreement with the data of Kawata et al. (1993), and indicate progression of hemorrhage is a genuine phenomenon that merits more attention.

Because blood is so toxic to neural tissues, in specific embodiments, edema and hemorrhage are the best, most reliable and most readily quantifiable indicators of lesion severity. Ultimately, the intent is to map the time courses of several events (SUR1 up-regulation, edema, hemorrhage, overall lesion size), to gain a better understanding of their interdependencies. The underlying theme is that a transcriptional program is initiated in penumbral tissues that leads to up-regulation of SUR1-regulated $NC_{Ca-ATP}$ channels in penumbral capillaries. Loss of capillary integrity then ensues, resulting in edema and hemorrhage, which in turn puts further pressure on adjacent tissues, leading to an expansion of the damage.

In one aspect, the time course of lesion evolution after SCI is determined, with specific focus on the time course for edema, hemorrhage, and overall lesion size. The same model is used here as described elsewhere herein. By the very nature of the measurements, different series of animals are studied for each of these 3 endpoints. Thus, tissues are harvested at various times after SCI to determine tissue wet and dry weights, to obtain measures of excess water, the primary constituent of edema. Tissues are harvested at various times after SCI to determine tissue Hgb content, which can be converted into values of excess blood in tissues outside of the intravascular compartment. Tissues are harvested at various times after SCI to determine lesion size and extent, using (immuno-) histochemical staining with H&E, GFAP, myelin stain (Eriochrome cyanine-R) and RBC's.

Time Course of Edema, Measured as Excess Water in the Cord at 0, ¾, 1.5, 3, 6, 12, 24 hr After Injury Cord edema results from altered function of capillaries in the area of injury. This altered function can lead to formation of ionic and/or vasogenic edema, with the most important constituent of both being water. Water, of course, is normally present in healthy tissues, but excess water is the cardinal sign of edema—without excess water, there is no edema to cause mass effect on healthy tissues, whereas with excess water, tissue edema and swelling are present (by definition) that can compromise function of otherwise intact tissues.

Edema (excess water) is measured using the standard method of wet weight/dry weight, as used by other groups studying edema in rat SCI (Kwo et al., 1989; Demediuk et al., 1990; Sharma and Olsson, 1990; Sribnick et al., 2005). Edema is measured in 7 groups of animals with contusion SCI, sacrificed at 7 different time points after injury, with 5 rats per group.

Preparation of Tissues.

After death, animals are perfused with heparinized PBS to remove intravascular blood. Then, the spinal cord is exposed and a 6-mm segment encompassing the contusion is isolated.

Tissue Water.

The excised cord is carefully blotted to remove droplets of fluid and is carefully weighed on a precision scale to obtain the wet weight ($W_W$). The tissues are then dried to constant weight at 80° C. and reweighed to obtain the dry weight ($W_D$). Tissue water, expressed as percent of $W_W$, is computed as $(W_W-W_D)/W_W \times 100$.

Statistical Analysis.

Means for different times are compared using ANOVA.

Time Course of Hemorrhagic Conversion, Measured as Excess Hemoglobin in the Cord at 0, ¾, 1.5, 3, 6, 12, 24 hr after Injury Blood in tissue results from the ultimate failure of capillaries, representing the end-stage of loss of capillary integrity. Part of the burden of excess blood in the contusion site arises from the initial impact that shears and disrupts tissues directly. In specific embodiments, a second component arises from hemorrhagic conversion, wherein penumbral tissues including capillaries succumb to secondary injury mechanisms, resulting in extravasation of blood and expansion of hemorrhagic tissues.

Blood is measured using a spectrophotometric assay for Hgb (Pfefferkorn and Rosenberg, 2002). Blood is measured in 7 groups of animals with contusion SCI, which are sacrificed at 7 different time points after injury, with 5 rats per group.

Preparation of Tissues.

After death, animals are perfused with heparinized PBS to remove intravascular blood. Then, the spinal cord is exposed and a 6-mm segment encompassing the contusion is isolated.

Hgb Measurements.

Hemoglobin (Hgb) in spinal cord tissue is quantified spectrophotometrically after conversion to cyanomethemoglobin using Drabkin's reagent. This method allows determination of hemoglobin concentrations as low as 5 mg/dL (Choudhri et al., 1997; Pfefferkorn and Rosenberg, 2003), and has been validated for brain tissue for use in assessing hemorrhagic conversion in stroke (Pfefferkorn and Rosenberg, 2003). A 5-mm segment of spinal cord tissue encompassing the injury is placed in a volume of water (molecular grade) that is 9× its weight, followed by homogenization for 30 sec, sonication on ice with a pulse ultrasonicator for 1 min, and centrifugation at 13,000 rpm for 45 min. After the Hgb-containing supernatant is collected, 80 μL of Drabkin's reagent (Sigma; $K_3Fe(CN)_6$ 200 mg/L, KCN 50 mg/L, $NaHCO_3$ 1 μg/L, pH 8.6) is added to a 20-μL aliquot and allowed to stand for 15 min. This reaction converts hemoglobin to cyanomethemoglobin, which has an absorbance peak at 540 nm, and whose concentration can then be assessed by the OD of the solution at 540 nm using a microplate reader. Values of Hgb are converted into equivalent microliters of blood using a standardized curve made from measurements on normal spinal cord "doped" with known volumes of blood, and adjusted as necessary for the measured hematocrit of the animal.

Statistical Analysis.

Means for different times are compared using ANOVA. Progression of Lesion Volume, Assessed Myelin Stain (Eriochrome Cyanine-R) and RBC Stain at 0, 1.5, 3, 24 hr after Injury Histological examination of lesions are performed in 3 groups of animals with contusion SCI, which are sacrificed at 3 different time points after injury, with 5 rats per group. The specific times are chosen for the following reasons: (i) time 0 hr—immediately after injury, to obtain a baseline measurement; (ii) time 3 hr, which corresponds to the time that Kawata et al. 18 noted maximum progression of hemorrhage; (iii) time 24 hr, which should represent a steady-state, i.e., the mature lesion with secondary injury largely complete.

Preparation of Tissues.

After death, animals are perfused with heparinized PBS followed by 4% paraformaldehyde. The spinal cord is exposed and a 15-mm segment encompassing the contusion is isolated. After appropriate marking for orientation, the 15-mm segment is divided into 3 segments: (i) the 5-mm segment through the region of maximal injury at the site of impact, (ii) the 5-mm segment rostral to the impact site; (iii) the 5-mm segment caudal to the impact site. Cord segments are cryoprotected and processed for cryosectioning.

Serial, Axial Cryosections (10 μm) are Prepared from Each of the 3 Segments.

From each segment, one section every 500 μm is labeled for RBC's and for myelin (Eriochrome cyanine-R staining) and is used to reconstruct the lesion volume. In addition, representative sections from each segment are immunolabeled for SUR1 and GFAP, and stained with H&E.

Histochemistry.

Staining and immunolabeling are carried out using protocols, as described elsewhere herein.

Peroxidase Staining for RBCs.

Peroxidase staining is used to identify RBCs in situ that have not been removed by postmortem perfusion. To visualize RBCs, sections are processed for routine HRP detection, but with a low concentration of $H_2O_2$(0.1%), to preserve intrinsic erythrocyte peroxidase activity (Michelson, 1998; Neve, 1995). Microscopic examination is used to determine whether remaining RBCs are inside of capillaries, reflecting "no reflow phenomenon" (Ito et al., 1980; Li et al., 1998; Liu et al., 20020), or intraparenchymal, reflecting hemorrhagic conversion.

Lesion Volume.

The volume of the lesion is automatically calculated after 3-D reconstruction using IP Lab software.

Statistical Analysis.

Means for different times will be compared using ANOVA.

Although in specific embodiments, hemorrhagic conversion is complete by 3 hr (Kawata et al., 1993), in other embodiments a longer window is determined. Based on data for hemorrhagic conversion, in specific embodiments there is a positive relationship between SUR1 expression on the one hand, and edema, hemorrhage and lesion volume on the other hand. Such findings indicates there is strong support for the treatment window for SCI is sufficiently long to justify early aggressive intervention to inhibit SUR1.

Example 9

Determination of the Optimal Time-Window and Dose for Treatment with Glibenclamide In one embodiment, using edema as the treatment endpoint, the effect of treatment with glibenclamide is measured, starting at various times after injury (1-4 hr) and with various doses (4 different doses) of glibenclamide. In other embodiments, using hemorrhagic conversion as the treatment endpoint, the effect of treatment with glibenclamide is measured, starting at various times after injury (1-4 hr) and with various doses (4 different doses) of glibenclamide.

In one embodiment, early treatment with the proper dose of the SUR1 antagonist, glibenclamide, minimizes formation of edema. In another embodiment, early treatment with the proper dose of the SUR1 antagonist, glibenclamide, minimizes hemorrhagic conversion.

There is data showing a salutary effect of glibenclamide when treatment is begun by constant infusion immediately after contusion SCI. These findings indicate that this drug is useful if a proper treatment is utilized, but further characterization of the optimal dose and timing of treatment is important. The endpoints chosen to study here reflect the embodiment that edema and hemorrhage are reliable, quantifiable indicators of lesion severity.

In one embodiment, the effect of glibenclamide on edema and hemorrhage is determined when dosing and timing are varied. Four different time delays (1-4 hr) before administration of one dose of drug are studied, and four different doses of drug are studied when drug is administered with a 2-hr delay. Using this scheme, two series of animals are studied, one in which edema is measured and one in which hemorrhage is measured.

Using Edema as the Treatment Endpoint, Measure the Effect of Treatment with Glibenclamide, Starting at Various Times after Injury (1-4 hr) and with Various Doses (4 Different Doses) of Glibenclamide Eleven groups of animals with contusion SCI, with 5 rats/group, are studied as follows:

| | |
|---|---|
| 1. | 1-hr delay/vehicle control |
| 2. | 1-hr delay/dose2 |
| 3. | 2-hr delay/vehicle control |
| 4. | 2-hr delay/dose2 |
| 5. | 3-hr delay/vehicle control |
| 6. | 3-hr delay/dose2 |
| 7. | 4-hr delay/vehicle control |
| 8. | 4-hr delay/dose2 |
| 9. | 2-hr delay/dose1 |
| 10. | 2-hr delay/dose3 |
| 11. | 2-hr delay/dose4 | where:

dose1=loading dose, 5 μg/kg, i.p., plus glucose 0.1 gm/kg; infusion rate, 75 ng/hr, s.q.

dose2=loading dose, 10 μg/kg, i.p., plus glucose 0.2 gm/kg; infusion rate, 150 ng/hr, s.q.

dose3=loading dose, 20 μg/kg, i.p., plus glucose 0.4 gm/kg; infusion rate, 300 ng/hr, s.q.

dose4=loading dose, 40 μg/kg, i.p., plus glucose 0.8 gm/kg; infusion rate, 600 ng/hr, s.q.

vehicle control=DMSO (same amount as in dose2) in PBS

These doses are calculated based on the following:

1. for glibenclamide (M.W., 494), the volume of distribution (in humans) is 0.2 L/kg (Gedeon and Koren, 2005).

2. for the loading doses, the serum concentrations sought are 50, 100, 200, and 400 nM. These concentrations are based on the $EC_{50}$ value for channel inhibition (48 nM at neutral pH (Chen and Simard, 2003)) coupled with the concepts that: (i) the target for glibenclamide (SUR1) resides within the lipid membrane; (ii) glibenclamide is a weak acid ($pK_a$6.3), so its lipid solubility increase at the low pH of injured or ischemic tissues; (iii) channel inhibition by glibenclamide is stronger at low pH4 (see FIGS. 1A-1D). Together, these observations indicate that lesser amounts than those predicted from the $EC_{50}$ value, i.e., less than 10× the $EC_{50}$, may be sufficient for high levels of inhibition.

3. lacking adequate pharmacokinetic data for the rat, infusion doses are based on previous experience with stroke (Simard et al., 2006) and initial studies with SCI (see above), which indicate that an infusion rate of 75 ng/hr is effective, but not completely effective, and is associated with only minimal effect on serum glucose. Together, this indicates that 75 ng/hr should be the lowest dose used.

4. as to the supplemental dose of glucose, there is preliminary data with the following: (i) a loading dose of 3.3 μg/kg of glibenclamide, showing that no supplemental glucose was needed; (ii) a loading dose of 33 μg/kg of glibenclamide, combined with a supplemental dose of 1 gm/kg of glucose, which gave high levels of serum glucose (~200 mg/dL), indicating that lesser amounts of supplemental glucose are sufficient for loading doses of 5-40 μg/kg. Serum glucose is checked during studies, and the dose of glucose may be changed if needed.

Specific methods may be employed:

Delay of treatment: Mini-osmotic pumps are implanted within 2-3 min of SCI. The pumps are fitted with catheters at the outflow that provide a dead space that requires the designated amount of time to fill. At the designated time, animals are also given a loading dose of glibenclamide and the supplemental dose of glucose.

Monitoring serum glucose: serum glucose is monitored every 6-12 hr during the first 24 hr after injury using a tail puncture to obtain a droplet of blood, and a standard glucometer for glucose measurements, to assure that levels are near euglycemic (80-160 mg/dL).

Preparation of tissues and measurement of excess water: see methods described above. At the time of sacrifice, measurements of serum glucose are also obtained.

Data analysis: vehicle-treated animals from these studies are compared with untreated "controls" from above, and vehicle-treated animals are compared with glibenclamide-treated animals. Statistical significance is assessed using ANOVA.

In a specific embodiment, using hemorrhagic conversion as the treatment endpoint, the effect of treatment with glibenclamide is measured, starting at various times after injury (1-4 hr) and with various doses (4 different doses) of glibenclamide Eleven groups of animals are studied with contusion SCI, with 5 rats/group, as detailed above.

Specific methods may be employed:

Delay of treatment: Drug treatment is performed as detailed above.

Monitoring serum glucose: serum glucose will be monitored every 6-12 hr during the first 24 hr after injury using a tail puncture to obtain a droplet of blood, and a standard glucometer for glucose measurements, to assure that levels are near euglycemic (80-160 mg/dL).

Preparation of tissues and measurement of hemoglobin: see methods as described above. At the time of sacrifice, measurements of serum glucose is also obtained.

Data analysis: vehicle-treated animals from these experiments are compared with untreated "controls" from above and vehicle-treated animals are compared with glibenclamide-treated animals. Statistical significance is assessed using ANOVA.

In specific embodiments, glibenclamide is beneficial in reducing edema and hemorrhage at the contusion site. Based on initial studies, this is true for the earliest times of treatment, in specific embodiments, but the duration of this window and the best dose is determined.

Glibenclamide can Reduce Serum Glucose Levels.

The dose used for initial studies (infusion of 75 ng/hr with no loading dose) resulted in only a small decrease in serum glucose. However, at higher doses, especially with a loading dose, this could potentially result in symptomatic hypoglycemia. Thus, throughout the studies, serum glucose levels are carefully monitored to assure that they do not drop too low (<80 mg/dL). Should this be found, the protocols are amended to correct for hypoglycemia, with the aim of not overcorrecting, but of maintaining levels between 80-160 mg/dL.

Hyperglycemia can Exacerbate Neurological Injury.

The loading dose of glibenclamide is supplemented with a single supplemental administration of glucose. As noted, above, serum glucose is carefully mounted to assure that hyperglycemia is not a problem, and if it is, the supplemental glucose may be reduced.

Example 10

Confirmation of the Therapeutic Efficacy of Glibenclamide in Neurobehavioral Studies In certain aspects, the effect of the best dose of glibenclamide on hindlimb and forelimb functional performance is assessed at 1, 3, 7 and 14 days after injury. In specific embodiments, in a rodent model of cervical spinal cord contusion, early treatment with the proper dose of the sulfonylurea receptor antagonist, glibenclamide, optimizes functional recovery The foregoing studies described above are all to be conducted with terminal endpoints (animals sacrificed to measure edema and blood in injured cord tissue). In the present embodiment, neurological/functional endpoints are measured. This facilitates in evaluating the above described studies by evaluating the effect of treatment intended to reduce secondary injury on actual functional outcome.

These studies are straightforward. The animals suffer the cervical SCI, with some delay, begin treatment and are later assessed using neurological functional tests. At present, for these experiments, the "dose2" treatment regimen as detailed above is used, with treatment starting with a 2-hr delay after SCI. It is determined if this specific treatment regimen of a 2-hr delay is tolerable. Alternative embodiments may be employed, such as to delay start of treatment as long as possible after injury, to most usefully simulate the human situation.

In one embodiment, the effect of the best dose of glibenclamide on hindlimb and forelimb functional performance is assessed at 1, 3, 7 and 14 days after injury. Two treatment groups are studied, each with 15 rats, to be treated either with vehicle or "best dose" glibenclamide (plus supplemental glucose), with 1-3 hr delay in onset of treatment (see discussion above on dose and delay). As noted above, the specific treatment regimen, including dose and delay, is determined from the results described above.

Specific methods may be employed:
Behavioral Training and Neurological Testing
Rearing Behavior.

This is a simple test that assesses truncal strength and lower extremity function. This is carried out as detailed in initial studies.

Horizontal Ladder Beam.

(Soblosky et al., 2001; Soblosky et al., 1996; Soblosky et al., 1997). The wooden horizontal ladder beam is 129.39 cm long and 16.51 cm wide, consisting of 37 rungs (0.79 cm diameter) spaced 2.54 cm apart (Soblosky et al., 1997). While crossing the beam, each rat is videotaped by a moving camera focused on the rat's right forepaw.

Rats are pre-trained to traverse the horizontal ladder beam by using white noise (60 dB) as an aversive stimulus that is terminated when the rat enters a goal box on the opposite end of the ladder beam. Training consists of 3 trials/day for 2 days, then 1 trial/day until criterion is achieved, then one trial every other day until injury. Criterion is set at ability to cross the beam with no more than one forepaw misplacement for five consecutive trials. The time to reach criterion varies from 7 to 12 days.

Using slow motion video playback, the number of forelimb slips, forepaw misplacements, and hindlimb slips are counted by a blinded evaluator. A forepaw misplacement is recorded if the rats fail to place the palm of their paw directly onto the rung. Although after injury many rats fail to place their fifth digit on the backside of the rung as before injury, this is not counted as misplacement.

Forelimb preference test (forelimb asymmetry) (Soblosky et al., 2001; Soblosky et al., 1996; Soblosky et al., 1997). Rats are placed in a clear box (inner dimensions: 10.3 cm wide×30.5 cm long×38.5 cm high) and their activity is videotaped for 5 min. Asymmetrical forelimb usage is counted from videotape playback. This consists of recording: (1) the limb (left or right) used to push off the floor prior to rearing; (2) the limb used for single forelimb support on the floor of the box; and (3) the limb used for single forelimb support against the walls of the box (Schallert et al., 2000). Usage of both forelimbs simultaneously is not counted. Data are expressed as percentage of right (unaffected by injury) forelimb use, i.e. (right forelimb use/right+left forelimb use)×100. Each rat is given only one trial weekly beginning 1 week after injury on the same day that it is tested on the ladder beam.

Example 11

Upregulation of the Regulatory and Pore-Forming Subunits of the Channel and Organ Effects In certain embodiments of the invention, expression of the channel in organs and tissues outside of the central nervous system is relevant, because the regulatory subunit of the channel, SUR1, is upregulated in heart, kidneys and liver by 4 hr ischemia, and the pore-forming subunit, TRPM4 is also upregulated by 4 hr ischemia. Furthermore, SUR1 and the SUR1-regulated $NC_{Ca-ATP}$ channel are upregulated in aortic endothelial cells by hypoxia, for example.

Figure 16:
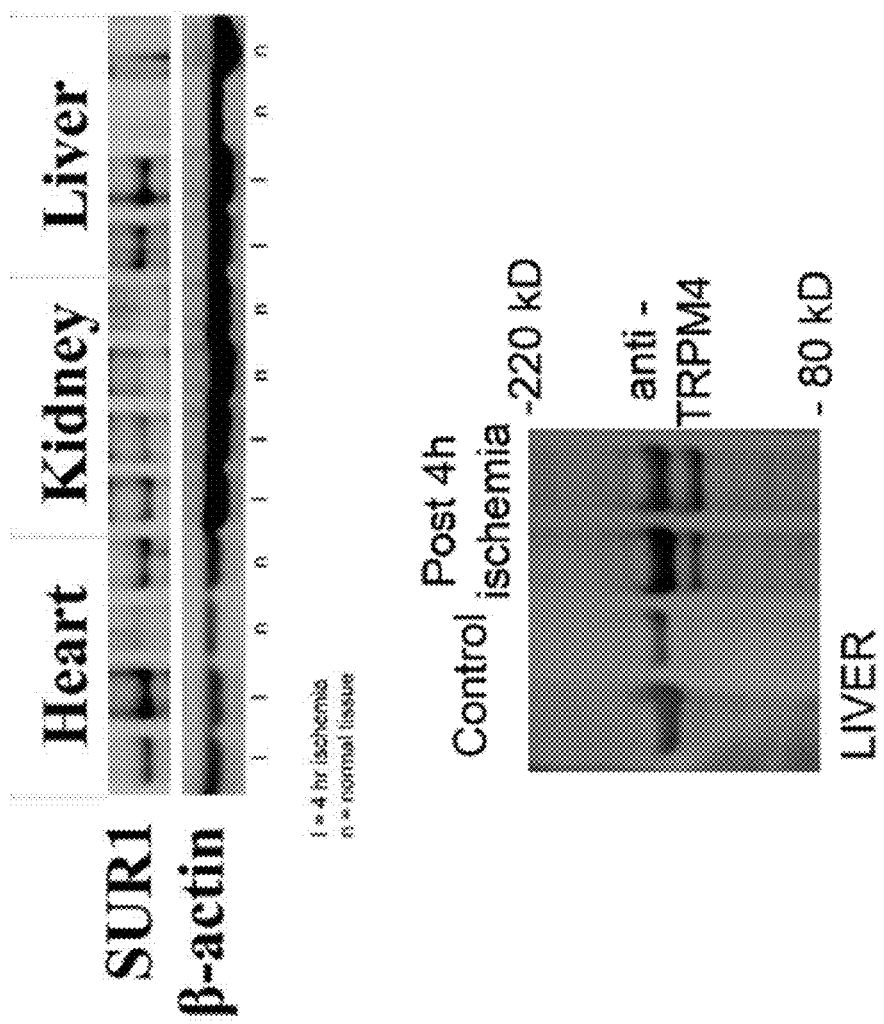
FIG. 16 shows expression of SUR1 and TRPM4 in particular organs following ischemia.
Figure 17:
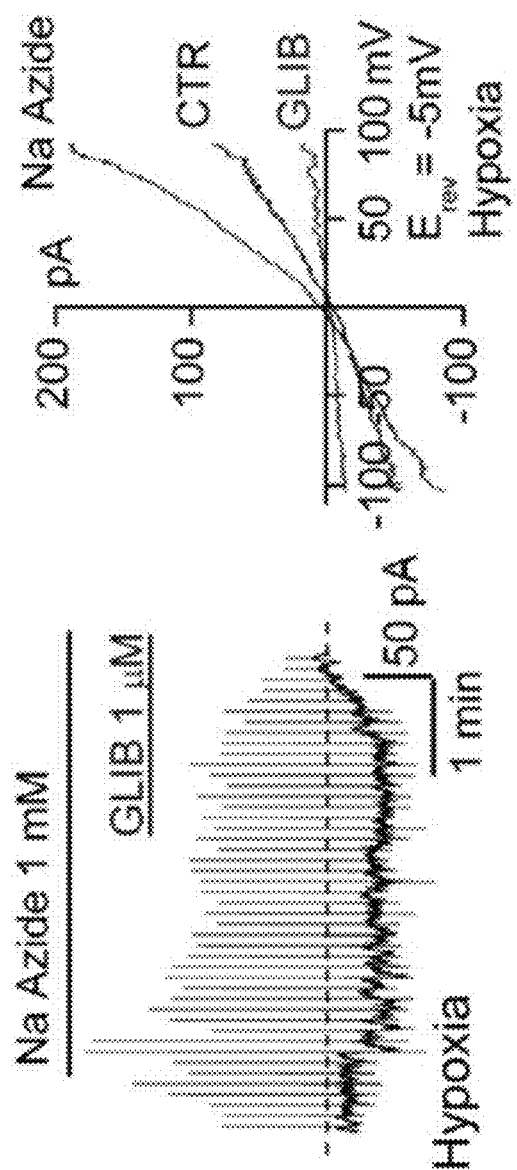
FIG. 17 shows whole-cell currents during ramp pulses (4/min; HP, −50 mV) or at the holding potential of −50 mV, before and after application of Na azide in endothelial cells exposed to normoxic or hypoxic conditions; the difference currents are also shown; data are representative of 7-15 recordings from human bEnd.3 cells for each condition.

The Regulatory Subunit of the Channel, SUR1, is Upregulated in Heart, Kidneys and Liver by 4 hr Ischemia; the Pore-Forming Subunit, TRPM4, is Also Upregulated by 4 hr Ischemia A 4-hr period of ischemia was produced in rat organs, including heart, kidney and liver, for example. These organs, as well as those of control rats that did not undergo ischemia, were harvested and assayed for SUR1 and TRPM4 expression using Western blot. As is evident from FIG. 16, visibly more SUR1 protein expression was associated with ischemia compared to control, non-ischemic organs. Re-blotting showed that the pore forming subunit, TRPM4, was also upregulated by 4 hr ischemia.

SUR1 and the SUR1-Regulated $NC_{Ca-ATP}$ Channel are Upregulated in Aortic Endothelial Cells by Hypoxia The study that follows pertains to the results shown in FIGS. 14A-14C, 15A-15E and 17. All of the studies in FIGS. 14A-14C and 15A-15E of the paper were obtained using human aortic endothelial cells.

Endothelial cell cultures from 3 sources, human brain microvascular, human aorta, and murine brain microvascular, were used to assess SUR1 expression and characterize channel properties following exposure to hypoxia, with the same results observed with all 3. Control cultures showed little expression of SUR1, but exposure to hypoxia for 24 h resulted in significant up-regulation of SUR1 (FIGS. 14A-14C). Insulinoma cells, which constitutively express SUR1-regulated $K_{ATP}$ channels, showed no up-regulation of SUR1 when exposed to the same hypoxic conditions (FIG. 14A-14C).

Patch clamp of endothelial cells was performed using a nystatin-perforated patch technique, to maintain the metabolic integrity of the cells. The identity of the activated channel can be assessed by measurement of the "reversal potential", the potential at which an ion channel current reverses from inward to outward. With physiologically relevant concentrations of ions intracellularly and extracellularly (high potassium inside, high sodium outside), the reversal potential can unambiguously distinguish between a $K^+$ channel current such as $K_{ATP}$, which reverses negative to −50 mV and a non-selective cation channel current such as $NC_{Ca-ATP}$, which reverses near 0 mV.

Channel activation was characterized by diazoxide, which opens SUR-regulated channels without ATP depletion and, of SUR activators, is the most selective for SUR1 over SUR2 (Chen et al., 2003). Patch clamp of endothelial cells cultured under normoxic conditions showed that diazoxide either had no effect or, in half of the cells, activated an outwardly rectifying current that reversed at potentials more negative than −50 mV, consistent with a $K_{ATP}$ channel (FIGS. 14A-14C) (Seino, 1999). By contrast, in most endothelial cells cultured under hypoxic conditions, diazoxide activated an ohmic current that reversed near 0 mV and that was inward at −50 mV (FIGS. 14A-14C), which is incompatible with $K_{ATP}$, but consistent with $NC_{Ca-ATP}$ channels (Chen et al., 2003; Chen and Simard, 2001; Simard et al., 2006).

Channel activation was also studied upon induction by Na azide, a mitochondrial uncoupler that depletes cellular ATP (Chen and Simard, 2001). In most endothelial cells exposed to hypoxic conditions, Na azide-induced ATP depletion activated an ohmic current that was inward at −50 mV, that reversed near 0 mV, and that was blocked by 1 μM glibenclamide (FIG. 17), again consistent with $NC_{Ca-ATP}$ channels.

Single channel recordings were performed using inside-out patches, with $Cs^+$ as the only permeant cation. This confirmed the presence of a channel that was sensitive to block by ATP on the cytoplasmic side and that had a single channel conductance of 37 pS (FIG. 15D). These findings are incompatible with $K_{ATP}$ channels, which is not permeable to $Cs^+$ and which has a slope conductance of ~75 pS, but are consistent with $NC_{Ca-ATP}$ channels.

The characteristics of the channel identified in endothelial cells from both aorta and brain capillaries from 2 species, including expression only after exposure to hypoxia, activation by depletion of cellular ATP or diazoxide, a reversal potential near 0 mV, conductance of $Cs^+$, and single channel conductance of 37 pS, reproduce exactly previous findings with $NC_{Ca-ATP}$ channels in astrocytes and neurons (Chen et al., 2003; Chen and simard, 2001; Simard et al, 2006), and reaffirm that the $NC_{Ca-ATP}$ channel is not constitutively expressed, is up-regulated only with an appropriate insult, and when expressed, is inactive until intracellular ATP is depleted.

Because of the following specific embodiments, solid organ protection and preservation, either in life in the context of tachycardia, atherosclerosis, hypotension (e.g. in septic shock, heart failure), thromboembolism, outside compression of a blood vessel (e.g. by a tumor), foreign bodies in the circulation (e.g. amniotic fluid in amniotic fluid embolism), sickle cell disease and similar conditions, for example, or post-mortem with the intention of organ transplantation, would be achieved by infusion of sulfonylureas and related compounds to block expression or function of the SUR1-regulated $NC_{Ca-ATP}$ channel: 1) solid organs outside of the CNS upregulate the regulatory as well as the pore-forming subunit of the channel in the context of ischemia; 2) upregulation of the regulatory subunit, SUR1, is associated with expression of functional SUR1-regulated $NC_{Ca-ATP}$ channels in cells outside of the CNS; and 3) ATP depletion in cells that express the channel is associated with cell death (Simard et al., 2006).

Example 12

Treating Non-CNS Organ Ischemia

An individual having non-central nervous system organ ischemia, suspected of having non-central nervous system organ ischemia, or at risk for having non-central nervous system organ ischemia is delivered an inhibitor of $NC_{Ca-ATP}$ channel. Although the inhibitor may be of any suitable kind, in particular cases the inhibitor is SUR1 antagonist, a TRPM4 antagonist, or both. In specific cases, the inhibitor is a sulfonylurea compound, a benzamido compound, or a meglitinide compound. In specific aspects, the inhibitor is glibenclamide (glyburide), tolbutamide, acetohexamide, chlorpropamide, tolazimide, glipizide, gliquidone, repaglinide, nateglinide, meglitinide, gliclazide, glimepiride, repaglinide, nateglinide, or mitiglinide or any of their active metabolites. In certain cases, the inhibitor is a blocker of TRPM4 channel, and in some embodiments the inhibitor is flufenamic acid, mefanimic acid, niflumic acid, or antagonists of VEGF, MMP, NOS, TNFα, NFκB, and/or thrombin.

The $NC_{Ca-ATP}$ inhibitor of the invention is provided in a pharmaceutically acceptable carrier, in certain cases, and the carrier renders the formulation suitable for administration. Administration may occur by any suitable method, although in particular cases the administration includes intravenous, subcutaneous, intramuscular, intracutaneous, intragastric or oral administration, for example.

The $NC_{Ca-ATP}$ inhibitor can be administered at any time to the individual, although in certain cases the agent is administered prior to, concurrent with, and/or following an ischemic episode.

The organ or tissue that suffers the ischemia may be of any kind, although in certain cases it includes the brain, spinal cord, heart, kidney, lung, liver, eye, pancreas, spleen, intestine, cornea, skin, bone marrow, heart valve, peripheral or central nerve, or connective tissue.

The $NC_{Ca-ATP}$ inhibitor is administered as a loading dose (also called a bolus) followed by a constant infusion, in certain embodiments. Furthermore, the $NC_{Ca-ATP}$ inhibitor may be delivered in a dosage of less than 3.5 mg per day, and in specific embodiments the individual is delivered the inhibitor at a dosage of less than 0.8 mg/kg body weight within a 24 hour period, for example.

In particular embodiments, the inhibitor is delivered directly to the organ or tissue, for example prior to extraction of the organ or tissue, during extraction of the organ or tissue, or following extraction of the organ or tissue. The delivering may be further defined as delivering the inhibitor to the organ or tissue prior to extraction of the respective organ or tissue from the individual, delivering the inhibitor to the organ or tissue during extraction of the respective organ or tissue from the individual, delivering the inhibitor to the organ or tissue subsequent to extraction of the respective organ or tissue from the individual, or a combination thereof, in specific cases. In some cases, the delivering is further defined as delivering the inhibitor to a recipient of the organ or tissue prior to transplantation of the respective organ or tissue into the recipient, during transplantation of the respective organ or tissue into the recipient, and/or after transplantation of the respective organ or tissue into the recipient.

REFERENCES

All patents and publications mentioned in the specification are indicative of the level of those skilled in the art to which the invention pertains. All patents and publications are herein incorporated by reference in their entirety to the same extent as if each individual publication was specifically and individually indicated to be incorporated by reference.

PATENTS

U.S. Pat. No. 5,399,363
U.S. Pat. No. 5,466,468
U.S. Pat. No. 5,543,158
U.S. Pat. No. 5,580,579
U.S. Pat. No. 5,629,001
U.S. Pat. No. 5,641,515
U.S. Pat. No. 5,725,871
U.S. Pat. No. 5,756,353
U.S. Pat. No. 5,792,451
U.S. Pat. No. 5,804,212
U.S. Pat. No. 6,613,308

PUBLICATIONS

Anisimov, S. V., Tarasov, K. V., Riordon, D., Wobus, A. M. & Boheler, K. R. SAGE identification of differentiation responsive genes in P19 embryonic cells induced to form cardiomyocytes in vitro. Mech. Dev. 117, 25-74 (2002).

Ashcroft, F. M. & Gribble, F. M. Tissue-specific effects of sulfonylureas: lessons from studies of cloned K(ATP) channels. J. Diabetes Complications 14, 192-196 (2000).

Bilgen, M., Abbe, R., Liu, S. J. & Narayana, P. A. Spatial and temporal evolution of hemorrhage in the hyperacute phase of experimental spinal cord injury: in vivo magnetic resonance imaging. Magn Reson. Med. 43, 594-600 (2000).

Bracken, M. B. et al. Administration of methylprednisolone for 24 or 48 hours or tirilazad mesylate for 48 hours in the treatment of acute spinal cord injury. Results of the Third National Acute Spinal Cord Injury Randomized Controlled Trial. National Acute Spinal Cord Injury Study. JAMA 277, 1597-1604 (1997).

Bracken, M. B. et al. Methylprednisolone or tirilazad mesylate administration after acute spinal cord injury: 1-year follow up. Results of the third National Acute Spinal Cord Injury randomized controlled trial. J. Neurosurg. 89, 699-706 (1998).

Bracken, M. B. Steroids for acute spinal cord injury. Cochrane. Database. Syst. Rev. CD001046 (2002).

Bryan, J. & Aguilar-Bryan, L. Sulfonylurea receptors: ABC transporters that regulate ATP-sensitive K(+) channels. Biochim. Biophys. Acta 1461, 285-303 (1999).

Chen, M. & Simard, J. M. Cell swelling and a nonselective cation channel regulated by internal $Ca^{2+}$ and ATP in native reactive astrocytes from adult rat brain. J. Neurosci. 21, 6512-6521 (2001).

Chen, M., Dong, Y. & Simard, J. M. Functional coupling between sulfonylurea receptor type 1 and a nonselective cation channel in reactive astrocytes from adult rat brain. J. Neurosci. 23, 8568-8577 (2003).

Choudhri, T. F., Hoh, B. L., Solomon, R. A., Connolly, E. S., Jr. & Pinsky, D. J. Use of a spectrophotometric hemoglobin assay to objectively quantify intracerebral hemorrhage in mice. Stroke 28, 2296-2302 (1997).

Cohen, M. V., Baines, C. P. & Downey, J. M. Ischemic preconditioning: from adenosine receptor to $K_{ATP}$ channel. Annu. Rev. Physiol 62, 79-109 (2000).

de, C. R., Jr., Burns, C. L., McAdoo, D. J. & Romanic, A. M. Metalloproteinase increases in the injured rat spinal cord. Neuroreport 11, 3551-3554 (2000).

Demediuk, P., Lemke, M. & Faden, A. I. Spinal cord edema and changes in tissue content of $Na^+$, $K^+$, and $Mg^{2+}$ after impact trauma in rats. Adv. Neurol. 52, 225-232 (1990).

Duchossoy, Y., Arnaud, S. & Feldblum, S. Matrix metalloproteinases: potential therapeutic target in spinal cord injury. Clin. Chem. Lab Med. 39, 362-367 (2001).

Duchossoy, Y., Horvat, J. C. & Stettler, O. MMP-related gelatinase activity is strongly induced in scar tissue of injured adult spinal cord and forms pathways for ingrowing neurites. Mol. Cell Neurosci. 17, 945-956 (2001).

Fehlings, M. G. & Baptiste, D. C. Current status of clinical trials for acute spinal cord injury. Injury 36 Suppl 2, B113-B122 (2005).

Gedeon, C. & Koren, G. Designing Pregnancy Centered Medications: Drugs Which Do Not Cross the Human Placenta. Placenta (2005).

Gensel, J. C. et al. Behavioral and histological characterization of unilateral cervical spinal cord contusion injury in rats. J. Neurotrauma 23, 36-54 (2006).

Gidday, J. M. et al. Leukocyte-derived matrix metalloproteinase-9 mediates blood-brain barrier breakdown and is proinflammatory after transient focal cerebral ischemia. Am. J. Physiol Heart Circ. Physiol 289, H558-H568 (2005).

Goussev, S. et al. Differential temporal expression of matrix metalloproteinases after spinal cord injury: relationship to revascularization and wound healing. J. Neurosurg. 99, 188-197 (2003).

Hainsworth, A. H., Spadoni, F., Lavaroni, F., Bernardi, G. & Stefani, A. Effects of extracellular pH on the interaction of sipatrigine and lamotrigine with high-voltage-activated (HVA) calcium channels in dissociated neurones of rat cortex. Neuropharmacology 40, 784-791 (2001).

Harder, D. R. et al. Formation and action of a P-450 4A metabolite of arachidonic acid in cat cerebral microvessels. Am. J. Physiol 266, H2098-H2107 (1994).

Hayes, K. C. & Kakulas, B. A. Neuropathology of human spinal cord injury sustained in sports-related activities. J. Neurotrauma 14, 235-248 (1997).

Heurteaux, C., Lauritzen, I., Widmann, C. & Lazdunski, M. Essential role of adenosine, adenosine A1 receptors, and ATP-sensitive $K^+$ channels in cerebral ischemic preconditioning. Proc. Natl. Acad. Sci. U. S. A 92, 4666-4670 (1995).

Ito, U. et al. Transient appearance of "no-reflow" phenomenon in Mongolian gerbils. Stroke 11, 517-521 (1980).

Justicia, C. et al. Neutrophil infiltration increases matrix metalloproteinase-9 in the ischemic brain after occlusion/reperfusion of the middle cerebral artery in rats. J. Cereb. Blood Flow Metab 23, 1430-1440 (2003).

Kawata, K. et al. [Experimental study of acute spinal cord injury: a histopathological study]. No Shinkei Geka 21, 45-51 (1993).

Kay, A. R. & Wong, R. K. Isolation of neurons suitable for patch-clamping from adult mammalian central nervous systems. J. Neurosci. Methods 16, 227-238 (1986).

Khan M, G. R. R. B. a. P. M. Hemorrhagic changes in experimental spinal cord injury models. Canadian Journal of Neuroscience 12, 259-262 (1985).

Kraus, K. H. The pathophysiology of spinal cord injury and its clinical implications. Semin. Vet. Med. Surg. (Small Anim) 11, 201-207 (1996).

Kwo, S., Young, W. & Decrescito, V. Spinal cord sodium, potassium, calcium, and water concentration changes in rats after graded contusion injury. J. Neurotrauma 6, 13-24 (1989).

Kwon, B. K., Tetzlaff, W., Grauer, J. N., Beiner, J. & Vaccaro, A. R. Pathophysiology and pharmacologic treatment of acute spinal cord injury. Spine J. 4, 451-464 (2004).

Li, P. A. et al. Capillary patency after transient middle cerebral artery occlusion of 2 h duration. Neurosci. Lett. 253, 191-194 (1998).

Liss, B. & Roeper, J. Molecular physiology of neuronal K-ATP channels (review). Mol. Membr. Biol. 18, 117-127 (2001).

Liss, B. Improved quantitative real-time RT-PCR for expression profiling of individual cells. Nucleic Acids Res. 30, e89 (2002).

Liu, S., Connor, J., Peterson, S., Shuttleworth, C. W. & Liu, K. J. Direct visualization of trapped erythrocytes in rat brain after focal ischemia and reperfusion. J. Cereb. Blood Flow Metab 22, 1222-1230 (2002).

Lo, E. H., Broderick, J. P. & Moskowitz, M. A. tPA and proteolysis in the neurovascular unit. Stroke 35, 354-356 (2004).

Lorenzl, S., De, P. G., Segal, A. Z. & Beal, M. F. Dysregulation of the levels of matrix metalloproteinases and tissue inhibitors of matrix metalloproteinases in the early phase of cerebral ischemia. Stroke 34, e37-e38 (2003).

Michelson, A. M. Selenium glutathione peroxidase: some aspects in man. J. Environ. Pathol. Toxicol. Oncol. 17, 233-239 (1998).

Montaner, J. et al. Matrix metalloproteinase-9 pretreatment level predicts intracranial hemorrhagic complications after thrombolysis in human stroke. Circulation 107, 598-603 (2003).

Moyer, J. R., Jr. & Brown, T. H. Methods for whole-cell recording from visually preselected neurons of perirhinal cortex in brain slices from young and aging rats. J. Neurosci. Methods 86, 35-54 (1998).

Nedergaard, M., Kraig, R. P., Tanabe, J. & Pulsinelli, W. A. Dynamics of interstitial and intracellular pH in evolving brain infarct. Am. J. Physiol 260, R581-R588 (1991).

Neve, J. Human selenium supplementation as assessed by changes in blood selenium concentration and glutathione peroxidase activity. J. Trace Elem. Med. Biol. 9, 65-73 (1995).

Noble, L. J., Donovan, F., Igarashi, T., Goussev, S. & Werb, Z. Matrix metalloproteinases limit functional recovery after spinal cord injury by modulation of early vascular events. J. Neurosci. 22, 7526-7535 (2002).

Ohta, K., Fujimura, Y., Nakamura, M., Watanabe, M. & Yato, Y. Experimental study on MRI evaluation of the course of cervical spinal cord injury. Spinal Cord. 37, 580-584 (1999).

Perillan, P. R. et al. Inward rectifier K(+) channel Kir2.3 (IRK3) in reactive astrocytes from adult rat brain. Glia 31, 181-192 (2000).

Perillan, P. R., Chen, M., Potts, E. A. & Simard, J. M. Transforming growth factor-beta 1 regulates Kir2.3 inward rectifier $K^+$ channels via phospholipase C and protein kinase C-delta in reactive astrocytes from adult rat brain. J. Biol. Chem. 277, 1974-1980 (2002).

Perillan, P. R., Li, X. & Simard, J. M. K(+) inward rectifier currents in reactive astrocytes from adult rat brain. Glia 27, 213-225 (1999).

Pfefferkorn, T. & Rosenberg, G. A. Closure of the blood-brain barrier by matrix metalloproteinase inhibition reduces rtPA-mediated mortality in cerebral ischemia with delayed reperfusion. Stroke 34, 2025-2030 (2003).

Romanic, A. M., White, R. F., Arleth, A. J., Ohlstein, E. H. & Barone, F. C. Matrix metalloproteinase expression increases after cerebral focal ischemia in rats: inhibition of matrix metalloproteinase-9 reduces infarct size. Stroke 29, 1020-1030 (1998).

Sasaki, S., Schneider, H. & Renz, S. Microcirculatory disturbances during the early phase following experimental spinal cord trauma in the rat. Adv. Neurol. 20, 423-431 (1978).

Schallert, T., Fleming, S. M., Leasure, J. L., Tillerson, J. L. & Bland, S. T. CNS plasticity and assessment of forelimb sensorimotor outcome in unilateral rat models of stroke, cortical ablation, parkinsonism and spinal cord injury. Neuropharmacology 39, 777-787 (2000).

Schnittler, H. J., Schmandra, T. & Drenckhahn, D. Correlation of endothelial vimentin content with hemodynamic parameters. Histochem. Cell Biol. 110, 161-167 (1998).

Seidel, M. F., Simard, J. M., Hunter, S. F. & Campbell, G. A. Isolation of arteriolar microvessels and culture of smooth muscle cells from cerebral cortex of guinea pig. Cell Tissue Res. 265, 579-587 (1991).

Seino, S. Physiology and pathophysiology of K(ATP) channels in the pancreas and cardiovascular system: a review. J. Diabetes Complications 17, 2-5 (2003).

Seino, S. 1999. ATP-sensitive potassium channels: a model of heteromultimeric potassium channel/receptor assemblies. Annu. Rev. Physiol 61:337-362.

Sharma, H. S. & Olsson, Y. Edema formation and cellular alterations following spinal cord injury in the rat and their modification with p-chlorophenylalanine. Acta Neuropathol. (Berl) 79, 604-610 (1990).

Simard, J. M., Tsymbalyuk, O., Ivanov, A., Ivanova, S., Bhatta, S., Geng, Z., Woo, S. K., and Gerzanich, V. 2007. Endothelial sulfonylurea receptor 1-regulated $NC_{Ca\text{-}ATP}$ channels mediate progressive hemorrhagic necrosis following spinal cord injury. J. Clin. Invest 117:2105-2113.

Simard, J. M. et al. Newly expressed SUR1-regulated $NC_{(Ca\text{-}ATP)}$ channel mediates cerebral edema after ischemic stroke. Nat. Med. 12, 433-440 (2006).

Soblosky, J. S., Colgin, L. L., Chorney-Lane, D., Davidson, J. F. & Carey, M. E. Ladder beam and camera video recording system for evaluating forelimb and hindlimb deficits after sensorimotor cortex injury in rats. J. Neurosci. Methods 78, 75-83 (1997).

Soblosky, J. S., Matthews, M. A., Davidson, J. F., Tabor, S. L. & Carey, M. E. Traumatic brain injury of the forelimb and hindlimb sensorimotor areas in the rat: physiological, histological and behavioral correlates. Behav. Brain Res. 79, 79-92 (1996).

Soblosky, J. S., Song, J. H. & Dinh, D. H. Graded unilateral cervical spinal cord injury in the rat: evaluation of forelimb recovery and histological effects. Behav. Brain Res. 119, 1-13 (2001).

Sribnick, E. A. et al. Estrogen attenuated markers of inflammation and decreased lesion volume in acute spinal cord injury in rats. J. Neurosci. Res. 82, 283-293 (2005).

Sucher, N. J., Deitcher, D. L., Baro, D. J., Warrick, R. M. & Guenther, E. Genes and channels: patch/voltage-clamp analysis and single-cell RT-PCR. Cell Tissue Res. 302, 295-307 (2000).

Suslov, O. N., Kukekov, V. G., Laywell, E. D., Scheffler, B. & Steindler, D. A. RT-PCR amplification of mRNA from single brain neurospheres. J. Neurosci. Methods 96, 57-61 (2000).

Tator, C. H. & Fehlings, M. G. Review of the secondary injury theory of acute spinal cord trauma with emphasis on vascular mechanisms. J. Neurosurg. 75, 15-26 (1991).

Tator, C. H. & Koyanagi, I. Vascular mechanisms in the pathophysiology of human spinal cord injury. J. Neurosurg. 86, 483-492 (1997).

Velardo, M. J. et al. Patterns of gene expression reveal a temporally orchestrated wound healing response in the injured spinal cord. J. Neurosci. 24, 8562-8576 (2004).

Volgin, D. V., Swan, J. & Kubin, L. Single-cell RT-PCR gene expression profiling of acutely dissociated and immunocytochemically identified central neurons. J. Neurosci. Methods 136, 229-236 (2004).

Wang, X. et al. Mechanisms of hemorrhagic transformation after tissue plasminogen activator reperfusion therapy for ischemic stroke. Stroke 35, 2726-2730 (2004).

Weirich, S. D. et al. Histopathologic correlation of magnetic resonance imaging signal patterns in a spinal cord injury model. Spine 15, 630-638 (1990).

Wells, J. E. et al. An adverse role for matrix metalloproteinase 12 after spinal cord injury in mice. J. Neurosci. 23, 10107-10115 (2003).

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

I claim:

1. A method of treating or reducing ischemic damage in a subject comprising administering an inhibitor of an $NC_{Ca\text{-}ATP}$ channel that is a SUR1 antagonist and/or a TRPM4 antagonist as a loading bolus dose followed by a constant infusion of a maintenance dose, wherein the bolus dose is 30-90 times the amount of the maintenance dose.

2. The method of claim 1, wherein the SUR1 antagonist is glibenclamide (glyburide), tolbutamide, acetohexamide, chlorpropamide, tolazimide, glipizide, gliquidone, repaglinide, nateglinide, meglitinide, gliclazide, glimepiride, repaglinide, nateglinide, mitiglinide, a pharmaceutically salt thereof, or an active metabolite thereof.

3. The method of claim 1, wherein the TRPM4 antagonist is selected from the group consisting of flufenamic acid, mefanimic acid, niflumic acid, and antagonists of VEGF, MMP, NOS, TNFα, NFkB, and/or thrombin.

4. The method of claim 1, wherein said inhibitor is delivered by intravenous, subcutaneous, intramuscular, intracutaneous, intragastric or oral administration.

5. The method of claim 1, wherein the inhibitor is administered prior to an ischemic episode, concurrent with an ischemic episode, or both.

6. The method of claim 1, wherein the inhibitor is administered following an ischemic episode.

7. The method of claim 1, wherein the method further comprises delivering the inhibitor directly to the organ or tissue.

8. The method of claim 1, wherein the method further comprises delivering the inhibitor to the subject prior to extraction of an organ or tissue, during extraction of the organ or tissue, or both.

9. The method of claim 1, wherein the method further comprises delivering the inhibitor to an organ or tissue prior to extraction of the respective organ or tissue from the subject, delivering the inhibitor to the organ or tissue during extraction of the respective organ or tissue from the subject, delivering the inhibitor to the organ or tissue subsequent to extraction of the respective organ or tissue from the subject, or a combination thereof.

10. The method of claim 1, wherein the method further comprises delivering the inhibitor to a recipient of an organ or tissue prior to transplantation of the respective organ or tissue into the recipient, during transplantation of the respective organ or tissue into the recipient, and/or after transplantation of the respective organ or tissue into the recipient.

11. The method of claim 1, wherein the ischemic damage is related to organ preservation for transplantation, angina pectoris, or kidney reperfusion injury.

12. The method of claim 1, wherein the method further comprises delivery of an additional therapeutic agent.

13. The method of claim 12, wherein the additional therapeutic agent comprises an antacid, an immunosuppressant, an antiviral compound, an antibacterial compound, an antifungal compound, or a combination or mixture thereof.

14. The method of claim 12, wherein the additional therapeutic agent comprises anti-thymocyte globulin, basiliximab, methylprednisolone, tacrolimus, mycophenolate mofetil, prednisone, sirolimus, rapamycin, azathioprine, or a mixture thereof.

15. The method of claim 1, wherein SUR1 antagonist is administered to the subject in a dosage of less than 3.5 mg per day.

16. The method of claim 1, wherein the SUR1 antagonist is administered to the subject at a dosage of less than 0.8 mg/kg body weight within a 24 hour period.

17. The method of claim 1, wherein the maintenance dose is administered as a constant infusion.

18. The method of claim 1, wherein the maintenance dose is administered for six or more hours.

19. The method of claim 1, wherein the maintenance dose is administered for twenty-four or more hours.

* * * * *